US008531291B2

(12) United States Patent
Tran

(10) Patent No.: US 8,531,291 B2
(45) Date of Patent: Sep. 10, 2013

(54) PERSONAL EMERGENCY RESPONSE (PER) SYSTEM

(76) Inventor: Bao Tran, Saratoga, CA (US)

(*) Notice: Subject to any disclaimer, the term of this patent is extended or adjusted under 35 U.S.C. 154(b) by 50 days.

(21) Appl. No.: 13/338,269

(22) Filed: Dec. 28, 2011

(65) Prior Publication Data

US 2012/0092157 A1 Apr. 19, 2012

Related U.S. Application Data

(63) Continuation of application No. 13/052,386, filed on Mar. 21, 2011, and a continuation of application No. 12/770,553, filed on Apr. 29, 2010, and a continuation of application No. 11/480,231, filed on Jun. 30, 2006, now Pat. No. 7,733,224, and a continuation of application No. 11/252,279, filed on Oct. 16, 2005, now Pat. No. 7,420,472.

(51) Int. Cl.
*G08B 21/00* (2006.01)

(52) U.S. Cl.
USPC ......... 340/540; 340/506; 340/3.1; 340/573.1; 340/539.1; 340/539.11; 340/539.13

(58) Field of Classification Search
USPC .................... 340/506, 540, 3.1, 573.1, 539.1, 340/539.11, 539.13
See application file for complete search history.

(56) References Cited

U.S. PATENT DOCUMENTS

| 4,234,926 A | 11/1980 | Wallace et al. |
| 4,275,742 A | 6/1981 | Faisandier |
| 4,320,767 A | 3/1982 | Villa-Real |
| 4,412,545 A | 11/1983 | Okino et al. |
| 4,420,000 A | 12/1983 | Bailey |
| 4,537,202 A | 8/1985 | Mancini et al. |
| 4,557,270 A | 12/1985 | John |
| 4,595,018 A | 6/1986 | Rantala |
| 4,656,319 A | 4/1987 | Bially |
| 4,679,144 A | 7/1987 | Cox et al. |
| 4,778,449 A | 10/1988 | Weber et al. |
| 4,807,642 A | 2/1989 | Brown |
| 4,819,648 A | 4/1989 | Ko |
| 4,862,359 A | 8/1989 | Trivedi et al. |
| 4,869,261 A | 9/1989 | Penaz |
| 4,880,013 A | 11/1989 | Chio |
| 4,907,597 A | 3/1990 | Chamoun |
| 4,922,229 A | 5/1990 | Guenst |
| 4,964,411 A | 10/1990 | Johnson et al. |
| 5,090,418 A | 2/1992 | Squires et al. |
| RE34,015 E | 8/1992 | Duffy |
| 5,140,990 A | 8/1992 | Jones et al. |
| 5,161,529 A | 11/1992 | Stotts et al. |
| 5,162,991 A | 11/1992 | Chio |
| 5,271,411 A | 12/1993 | Ripley et al. |
| 5,285,793 A | 2/1994 | Slovut et al. |
| 5,287,859 A | 2/1994 | John |
| 5,309,916 A | 5/1994 | Hatschek |

(Continued)

OTHER PUBLICATIONS

U.S. Appl. No. 10/938,783, Wen.

*Primary Examiner* — Daryl Pope
(74) *Attorney, Agent, or Firm* — Tran & Associates

(57) ABSTRACT

A system includes one or more sensors mounted on a mobile patient; a wireless transceiver to communicate with a remote station; and a processor coupled to the sensor and the wireless transceiver to request assistance if the processor detects a fall by the mobile patient.

23 Claims, 23 Drawing Sheets

(56) References Cited

U.S. PATENT DOCUMENTS

| | | |
|---|---|---|
| 5,331,969 A | 7/1994 | Silberstein |
| 5,361,775 A | 11/1994 | Remes et al. |
| 5,365,426 A | 11/1994 | Siegel et al. |
| 5,368,039 A | 11/1994 | Moses |
| 5,370,126 A | 12/1994 | Clifford, Jr. |
| 5,375,610 A | 12/1994 | LaCourse et al. |
| 5,434,419 A | 7/1995 | Decupper |
| 5,435,316 A | 7/1995 | Kruse |
| 5,438,607 A | 8/1995 | Przygoda, Jr. et al. |
| 5,441,047 A | 8/1995 | David et al. |
| 5,458,620 A | 10/1995 | Adams et al. |
| 5,462,065 A | 10/1995 | Cusimano |
| 5,497,781 A | 3/1996 | Chen et al. |
| 5,505,208 A | 4/1996 | Toomim et al. |
| 5,513,651 A | 5/1996 | Cusimano et al. |
| 5,544,649 A | 8/1996 | David et al. |
| 5,544,661 A | 8/1996 | Davis et al. |
| 5,546,953 A | 8/1996 | Garfield |
| 5,551,435 A | 9/1996 | Sramek |
| 5,551,438 A | 9/1996 | Moses |
| 5,579,001 A | 11/1996 | Dempsey et al. |
| 5,579,775 A | 12/1996 | Dempsey et al. |
| 5,584,298 A | 12/1996 | Kabal |
| 5,623,939 A | 4/1997 | Garfield |
| 5,633,910 A | 5/1997 | Cohen |
| 5,652,570 A | 7/1997 | Lepkofker |
| 5,662,118 A | 9/1997 | Skubick |
| 5,671,741 A | 9/1997 | Lang et al. |
| 5,683,425 A | 11/1997 | Hauptmann |
| 5,692,215 A | 11/1997 | Kutzik et al. |
| 5,694,940 A | 12/1997 | Unger et al. |
| 5,708,417 A | 1/1998 | Tallman et al. |
| 5,709,215 A | 1/1998 | Perttu et al. |
| 5,710,551 A | 1/1998 | Ridgeway |
| 5,720,771 A | 2/1998 | Snell |
| 5,722,420 A | 3/1998 | Lee |
| 5,733,230 A | 3/1998 | Sawchuck et al. |
| 5,738,104 A | 4/1998 | Lo et al. |
| 5,738,105 A | 4/1998 | Kroll |
| 5,743,268 A | 4/1998 | Kabal |
| 5,772,603 A | 6/1998 | Ohlsson et al. |
| 5,775,330 A | 7/1998 | Kangas et al. |
| 5,776,073 A | 7/1998 | Garfield et al. |
| 5,785,960 A | 7/1998 | Rigg et al. |
| 5,788,643 A | 8/1998 | Feldman |
| 5,857,975 A | 1/1999 | Golub |
| 5,865,755 A | 2/1999 | Golub |
| 5,876,350 A | 3/1999 | Lo et al. |
| 5,935,077 A | 8/1999 | Ogle |
| 5,945,112 A | 8/1999 | Flynn et al. |
| 5,964,719 A | 10/1999 | Costello et al. |
| 5,967,975 A | 10/1999 | Ridgeway |
| 5,987,519 A | 11/1999 | Peifer et al. |
| 5,996,889 A | 12/1999 | Fuchs et al. |
| 6,002,957 A | 12/1999 | Finneran |
| 6,004,312 A | 12/1999 | Finneran et al. |
| 6,010,454 A | 1/2000 | Arieff et al. |
| 6,014,626 A | 1/2000 | Cohen |
| 6,032,035 A | 2/2000 | Webster et al. |
| 6,038,469 A | 3/2000 | Karlsson et al. |
| 6,047,202 A | 4/2000 | Finneran et al. |
| 6,050,940 A | 4/2000 | Braun et al. |
| 6,052,619 A | 4/2000 | John |
| 6,056,671 A | 5/2000 | Marmer |
| 6,063,051 A | 5/2000 | Stern |
| 6,070,140 A | 5/2000 | Tran |
| 6,076,011 A | 6/2000 | Hoover |
| 6,108,685 A | 8/2000 | Kutzik et al. |
| 6,160,478 A * | 12/2000 | Jacobsen et al. ......... 340/539.12 |
| 6,171,237 B1 | 1/2001 | Avitall et al. |
| 6,175,308 B1 | 1/2001 | Tallman et al. |
| 6,176,831 B1 | 1/2001 | Voss et al. |
| 6,184,797 B1 | 2/2001 | Stark et al. |
| 6,228,034 B1 | 5/2001 | Voss et al. |
| 6,230,056 B1 | 5/2001 | Kroll |
| 6,246,894 B1 | 6/2001 | Steur et al. |
| 6,280,393 B1 | 8/2001 | Granger et al. |
| 6,287,252 B1 | 9/2001 | Lugo |
| 6,299,583 B1 | 10/2001 | Eggers et al. |
| 6,336,900 B1 | 1/2002 | Alleckson et al. |
| 6,364,834 B1 | 4/2002 | Reuss et al. |
| 6,364,842 B1 | 4/2002 | Amano et al. |
| 6,368,283 B1 | 4/2002 | Xu et al. |
| 6,374,614 B2 | 4/2002 | Prueitt |
| 6,375,614 B1 | 4/2002 | Braun et al. |
| 6,398,727 B1 | 6/2002 | Bui et al. |
| 6,406,426 B1 | 6/2002 | Reuss et al. |
| 6,413,223 B1 | 7/2002 | Yang et al. |
| 6,416,480 B1 | 7/2002 | Nenov |
| 6,433,690 B2 | 8/2002 | Petelenz et al. |
| 6,440,067 B1 | 8/2002 | DeLuca et al. |
| 6,443,906 B1 | 9/2002 | Ting et al. |
| 6,445,299 B1 | 9/2002 | Rojas, Jr. |
| 6,466,816 B2 | 10/2002 | Granger et al. |
| 6,473,640 B1 | 10/2002 | Erlebacher |
| 6,475,146 B1 | 11/2002 | Frelburger et al. |
| 6,475,153 B1 | 11/2002 | Khair et al. |
| 6,487,442 B1 | 11/2002 | Wood |
| 6,514,211 B1 | 2/2003 | Baura |
| 6,515,593 B1 | 2/2003 | Stark et al. |
| 6,533,729 B1 | 3/2003 | Khair et al. |
| 6,544,173 B2 | 4/2003 | West et al. |
| 6,544,174 B2 | 4/2003 | West et al. |
| 6,546,269 B1 | 4/2003 | Kurnik |
| 6,554,774 B1 | 4/2003 | Miele |
| 6,556,860 B1 | 4/2003 | Groenewegen |
| 6,595,316 B2 | 7/2003 | Cybulski et al. |
| 6,597,944 B1 | 7/2003 | Hadas |
| 6,605,038 B1 | 8/2003 | Teller et al. |
| 6,609,023 B1 | 8/2003 | Fischell et al. |
| 6,612,984 B1 | 9/2003 | Kerr, II |
| 6,615,074 B2 | 9/2003 | Mickle et al. |
| 6,615,075 B2 | 9/2003 | Mlynash et al. |
| 6,616,613 B1 | 9/2003 | Goodman |
| 6,660,042 B1 | 12/2003 | Curcie et al. |
| 6,661,161 B1 | 12/2003 | Lanzo et al. |
| 6,676,600 B1 | 1/2004 | Conero et al. |
| 6,678,549 B2 | 1/2004 | Cusimano |
| 6,678,551 B2 | 1/2004 | Maalouf et al. |
| 6,687,519 B2 | 2/2004 | Steur et al. |
| 6,705,990 B1 | 3/2004 | Gallant et al. |
| 6,720,984 B1 | 4/2004 | Jorgensen et al. |
| 6,730,038 B2 | 5/2004 | Gallant et al. |
| 6,740,045 B2 | 5/2004 | Amano |
| 6,747,561 B1 | 6/2004 | Reeves |
| 6,760,620 B2 | 7/2004 | Sippens Groenewegen |
| 6,783,492 B2 | 8/2004 | Dominguez et al. |
| 6,804,656 B1 | 10/2004 | Rosenfeld et al. |
| 6,816,266 B2 | 11/2004 | Varshaneya et al. |
| 6,829,501 B2 * | 12/2004 | Nielsen et al. ............ 600/513 |
| 6,832,251 B1 | 12/2004 | Gelvin et al. |
| 6,834,436 B2 | 12/2004 | Townsend et al. |
| 6,843,771 B2 | 1/2005 | Lo et al. |
| 6,856,291 B2 | 2/2005 | Mickle et al. |
| 6,865,409 B2 | 3/2005 | Getsla et al. |
| 6,871,211 B2 | 3/2005 | Labounty et al. |
| 6,882,128 B1 | 4/2005 | Rahmel et al. |
| 6,887,202 B2 | 5/2005 | Currie et al. |
| 6,898,460 B2 | 5/2005 | Hoctor et al. |
| 6,907,288 B2 | 6/2005 | Daum |
| 6,912,420 B2 | 6/2005 | Scheiner et al. |
| 6,944,496 B2 | 9/2005 | Jeong et al. |
| 6,961,285 B2 | 11/2005 | Niemiec et al. |
| 6,965,794 B2 | 11/2005 | Brody |
| 6,973,344 B2 | 12/2005 | Finneran et al. |
| 6,974,419 B1 | 12/2005 | Voss et al. |
| 6,975,206 B2 | 12/2005 | Reining |
| 6,980,852 B2 | 12/2005 | Jersey-Willuhn et al. |
| 6,989,751 B2 | 1/2006 | Richards |
| 7,004,907 B2 | 2/2006 | Banet et al. |
| 7,011,629 B2 | 3/2006 | Bulat |
| 7,035,679 B2 | 4/2006 | Addison et al. |
| 7,043,293 B1 | 5/2006 | Baura |
| 7,285,090 B2 * | 10/2007 | Stivoric et al. ............ 600/300 |

| | | |
|---|---|---|
| 7,340,240 B2 | 3/2008 | McDonald |
| 2002/0013518 A1* | 1/2002 | West et al. .................. 600/300 |
| 2002/0120184 A1 | 8/2002 | Beck et al. |
| 2003/0004421 A1 | 1/2003 | Ting et al. |
| 2003/0125635 A1 | 7/2003 | Maalouf et al. |
| 2003/0135127 A1 | 7/2003 | Sackner et al. |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |
| 2003/0231115 A1 | 12/2003 | Stanners et al. |
| 2004/0044273 A1 | 3/2004 | Keith et al. |
| 2004/0102683 A1 | 5/2004 | Khanuja et al. |
| 2004/0122487 A1 | 6/2004 | Hatlestad et al. |
| 2004/0138568 A1 | 7/2004 | Lo et al. |
| 2004/0167409 A1 | 8/2004 | Lo et al. |
| 2004/0167417 A1 | 8/2004 | Schulhauser et al. |
| 2004/0199056 A1* | 10/2004 | Husemann et al. .......... 600/300 |
| 2004/0220490 A1 | 11/2004 | Appel et al. |
| 2004/0254493 A1 | 12/2004 | Chervin et al. |
| 2004/0260188 A1 | 12/2004 | Syed et al. |
| 2004/0267148 A1 | 12/2004 | Arand et al. |
| 2005/0038345 A1 | 2/2005 | Gorgenburg et al. |
| 2005/0061568 A1 | 3/2005 | Schondorf et al. |
| 2005/0079871 A1* | 4/2005 | Kirk et al. .................. 455/446 |
| 2005/0099387 A1 | 5/2005 | Matsumoto et al. |
| 2005/0113630 A1 | 5/2005 | Fox et al. |
| 2005/0113710 A1 | 5/2005 | Stahmann et al. |
| 2005/0115561 A1 | 6/2005 | Stahmann et al. |
| 2005/0143667 A1 | 6/2005 | Park et al. |
| 2005/0148882 A1* | 7/2005 | Banet et al. .................. 600/485 |
| 2005/0194926 A1 | 9/2005 | Di Stefano |
| 2005/0201585 A1 | 9/2005 | Jannard et al. |
| 2005/0209521 A1 | 9/2005 | Kettunen et al. |
| 2005/0222515 A1 | 10/2005 | Polyshchuk et al. |
| 2005/0228244 A1 | 10/2005 | Banet et al. |
| 2005/0228299 A1 | 10/2005 | Banet et al. |
| 2005/0228316 A1 | 10/2005 | Morgenstern et al. |
| 2005/0240086 A1 | 10/2005 | Akay et al. |
| 2005/0240523 A1 | 10/2005 | Richardson et al. |
| 2005/0245831 A1 | 11/2005 | Banet et al. |
| 2005/0261594 A1 | 11/2005 | Banet et al. |
| 2005/0261598 A1 | 11/2005 | Banet et al. |
| 2005/0278409 A1 | 12/2005 | Kutzik et al. |
| 2006/0009697 A1 | 1/2006 | Banet et al. |
| 2006/0009698 A1 | 1/2006 | Banet et al. |
| 2006/0047215 A1 | 3/2006 | Newman et al. |
| 2006/0079801 A1 | 4/2006 | DeLuca et al. |
| 2006/0082727 A1 | 4/2006 | Bolger et al. |
| 2006/0084878 A1 | 4/2006 | Banet et al. |
| 2006/0094975 A1 | 5/2006 | Manto |
| 2006/0105357 A1 | 5/2006 | Benesch et al. |
| 2007/0054777 A1* | 3/2007 | Kawai et al. .................. 482/1 |
| 2009/0245577 A1* | 10/2009 | Liu et al. .................. 382/103 |
| 2012/0190949 A1* | 7/2012 | McCombie et al. .......... 600/324 |

* cited by examiner

Build pattern of daily activities
Do
    Detect if the user's daily activities are within a predetermined threshold of normal activities
    Check that medication cabinet has been accessed on daily basis
    Check door/window is closed in the evening unless specified in advance
    Check that bathroom is not flooded
    Check that patient is not in bathroom for excessive amounts of time
    Check patient toilet for potential disease
    Check for normal usage of exercise equipment in accordance with doctor recommendations
    Check kitchen appliances to minimize risks of fire or flooding hazard
    Check cloth washer/dryer for usage activity
    Check refrigerator activity
    Check backyard motion sensor for intrusion and/or assistance that may be required if the user is injured in the backyard
    Check thermostat and heater/AC for temperature setting
    Check sleeping activities
    Check eating activities
    Check weight
    Check TV viewing or radio listening or computer usage habit
    Check traversing speed on stair
    If abnormality is detected, request assistance from authorized third party
    Update daily activity data structure
    Generate periodic summary/report/recommendations to person and authorized third parties
Loop

FIG. 3

Capture and transmit the person's daily activities over a wireless mesh network

Determine a pattern associated with the person's daily activities

Attach a housing having one or more bioelectric contacts coupleable to the person, the housing selected from one of: a patch, a wristwatch, a band, a wristband, a chest band, a leg band, a sock, a glove, a foot pad, a head-band, an ear-clip, an ear phone, a shower-cap, an armband, an ear-ring, eye-glasses, sun-glasses, a belt, a sock, a shirt, a garment, a jewelry, a bed spread, a pillow cover, a pillow, a mattress, a blanket, each having one or more sensors in communication with the wireless mesh network Detect a weakness in left half and right half of the person's body; a walking pattern for loss of balance or coordination; requesting hands/feet movement in a predetermined pattern and reading accelerometer output in accordance with the predetermined pattern; checking whether the person experienced dizziness or headache; displaying a text image and asking the person to read back the text image one eye at a time; using a speech recognizer to detect confusion, trouble speaking or understanding; and asking the person if numbness is felt in the body;

Request assistance if the person's current activity varies from the pattern or if a dangerous condition is detected

FIG. 4

| |
|---|
| Set up mesh network appliances (1000) |
| Determine patient position using in-door positioning system (1002) |
| Determine patient movement using accelerometer output (1004) |
| Determine vital parameter including patient heart rate (1006) |
| Determine if patient needs assistance based on in-door position, fall detection and vital parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

FIG. 5

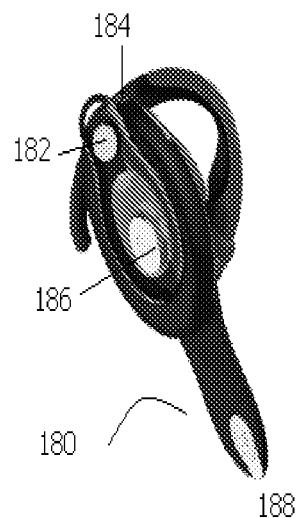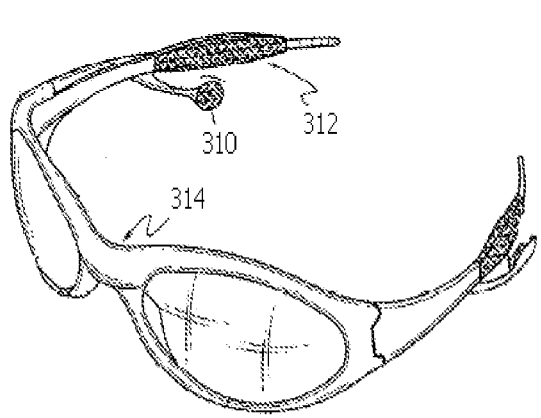
FIG. 13
FIG. 14B
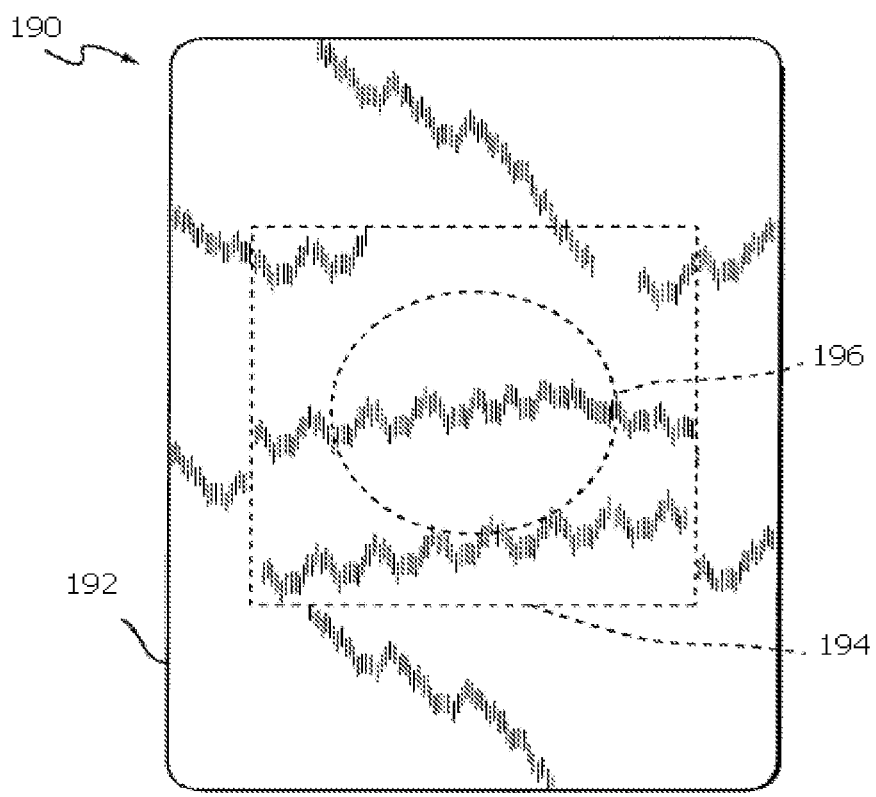
FIG. 14A

| |
|---|
| Detect weakness in left half and right half of patient body - arms, legs, face (3000) |
| Detect walking pattern for loss of balance or coordination (3002) |
| Ask user to move hands/feet in a predetermined pattern (3004) |
| Read accelerometer output in accordance with predetermined pattern movement (3006) |
| Provide accelerometer output to a pattern classifier (3008) |
| Check whether patient is experiencing dizziness or sudden, severe headache with no known cause (3010) |
| Display a text image and ask the patient to read back the text image, one eye at a time (3012) |
| Use speech recognizer to detect confusion, trouble speaking or understanding (3014) |
| Ask patient if they feel numbness in the body- arms, legs, face (3016) |
| Ask patient to squeeze gauge/force sensor to determine force applied during squeeze (3018) |

FIG. 16C

| |
|---|
| Compare historical left shoulder (LS) strength against current LS strength (3200) |
| Compare historical right shoulder (RS) strength against current RS strength (3202) |
| Compare historical left hip (LH) strength against current LH strength (3204) |
| Compare historical right hip (RH) strength against current RH strength (3206) |
| If variance between historical and current strength exceeds threshold, generate warning (3208) |

FIG. 16E

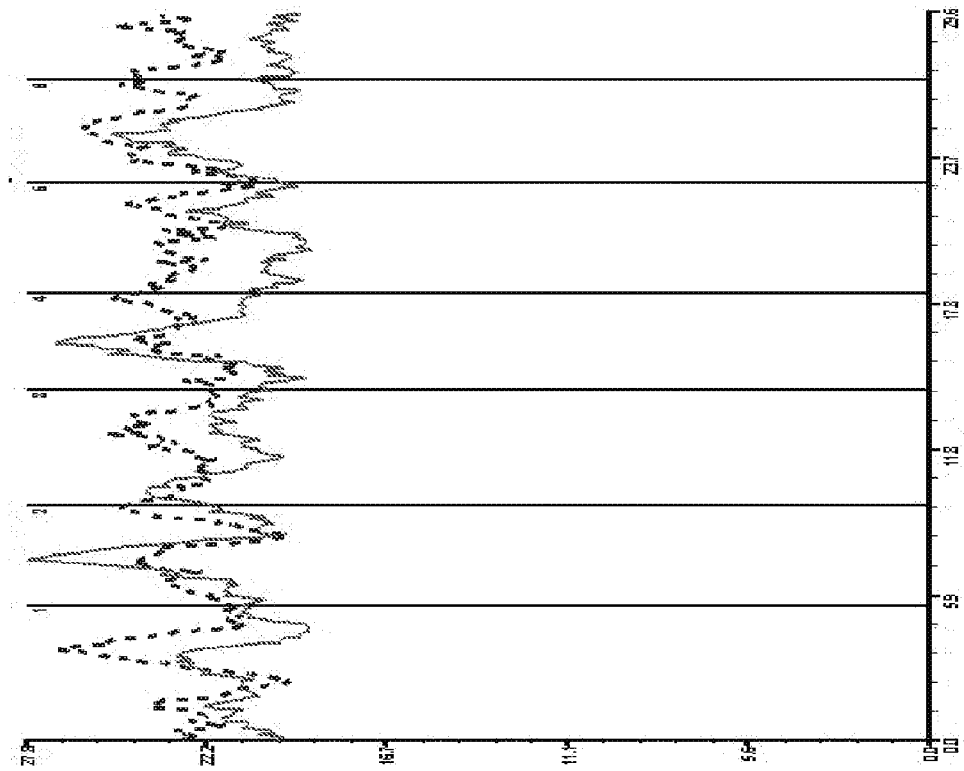
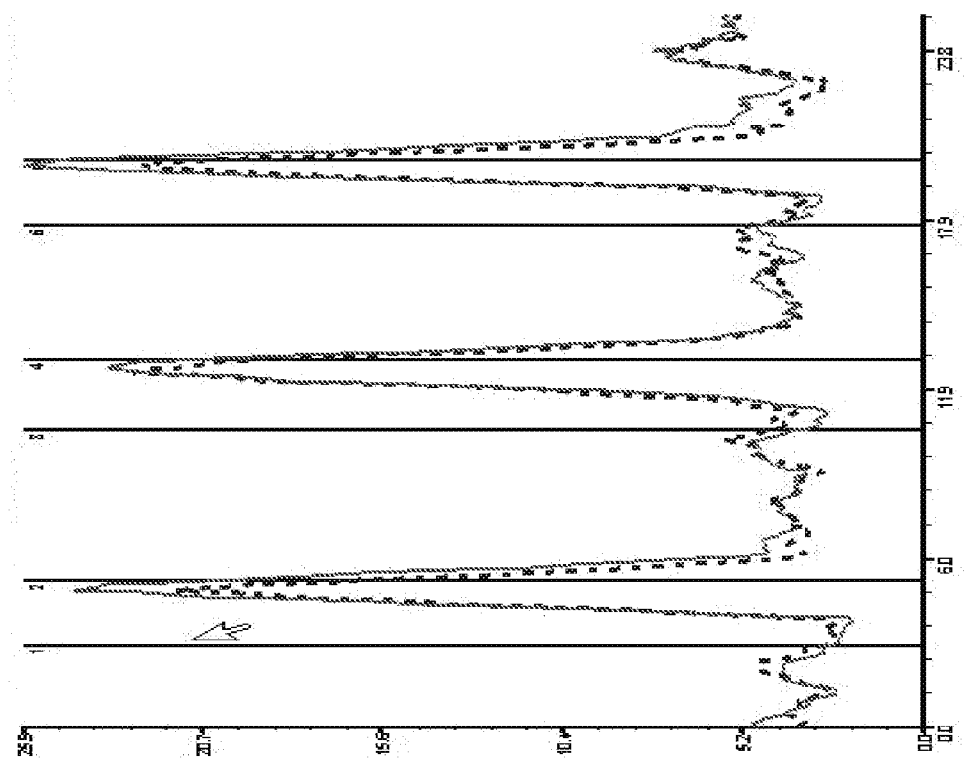
FIG. 17B
FIG. 17C

PERSONAL EMERGENCY RESPONSE (PER) SYSTEM

This application is a continuation of application Ser. No. 13/052,386, filed Mar. 21, 2011, application Ser. No. 12/770,553 filed Apr. 29, 2010, application Ser. No. 11/480,231 filed Jun. 30, 2006, and application Ser. No. 11/252,279 filed Oct. 16, 2005, the contents of which are incorporated by reference.

BACKGROUND

This invention relates generally to a PER system.

Improvements in living condition and advances in health care have resulted in a marked prolongation of life expectancy for elderly and disabled population. These individuals, a growing part of society, are dependent upon the delivery of home health and general care, which has its own set of challenges and drawbacks. This population needs continuous general, as well as medical, supervision and care. The creation of retirement facilities and old age homes, as well as other geriatric facilities, provides only a partial solution to the problems facing the geriatric population. As discussed in U.S. Pat. Nos. 5,544,649 and 6,433,690, the notion of ambulatory (home environment) patient care is gaining increased popularity and importance. As discussed in the '649 patent, the number of old aged people receiving home care services under Medicare has shown a 13% annual growth rate and has tripled in 10 years (1978-1988) from 769,000 to 2.59 million. This shift in patient care from the "sheltered" institutional milieu to the patient's home, work place, or recreational environment is driven in part by cost and in part to a new care concept that prefers keeping the aged and the disabled in their own natural environment for as long as possible.

Typically, home care is carried out either by the patient's family or by nonprofessional help. The monitoring equipment at home care facilities is usually minimal or nonexistent, and the patient has to be transported to the doctor's office or other diagnostic facility to allow proper evaluation and treatment. Patient follow-up is done by means of home visits of nurses which are of sporadic nature, time consuming and generally very expensive. A visiting nurse can perform about 5-6 home visits per day. The visits have to be short and can usually not be carried out on a daily basis. Moreover, a visiting nurse program provides no facilities for continuous monitoring of the patient and thus no care, except in fortuitous circumstances, in times of emergency.

SUMMARY

In one aspect, a system includes one or more sensors mounted on a mobile patient; a wireless transceiver to communicate with a remote station; and a processor coupled to the sensor and the wireless transceiver to request assistance if the processor detects a fall by the mobile patient.

In another aspect, a method to monitor a person includes capturing motions from the person using a mobile device attached to the person; determining a pattern associated with a dangerous condition; and requesting assistance if a dangerous condition is detected.

In yet another aspect, a method of automatically requesting assistance for a mobile patient includes attaching a mobile device with one or more accelerometers on the patient to detect patient motion; determining a fall based on detected patient motion; and automatically requesting assistance from the mobile device on behalf of the patient if help is needed.

In a further aspect, a method to provide personal emergency response for a patient includes wearing a mobile device with a help button and at least one or more accelerometers on the patient to detect patient motion; determining a fall based on detected motions including one or more changes in height or one or more accelerations associated with movements by the patient; waiting for a predetermined period to detect if the patient can recover from the fall and automatically requesting assistance if the patient is unable to recover from the fall; and requesting assistance if the patient pushes the help button.

In yet another aspect, a monitoring system includes one or more wireless nodes forming a wireless mesh network; a user activity sensor including a wireless mesh transceiver adapted to communicate with the one or more wireless nodes using the wireless mesh network; and a digital monitoring agent coupled to the wireless transceiver through the wireless mesh network to request assistance from a third party based on the user activity sensor.

Implementations of the system may include one or more of the following. The user activity sensor includes: an indoor position sensor, a motion sensor, a door sensor, a bathroom sensor, a water overflow sensor, an exercise equipment sensor, a smoke detector, an oven sensor, a cooking range sensor, a dish washer sensor, a cabinet door sensor, a refrigerator sensor, a refrigerator container sensor, a kitchen water flow sensor, a dish sensor, a bowl sensor, a chair sitting sensor, a sofa sitting sensor, a bed sensor, a weight sensor, a television viewing sensor, a radio listening sensor, an EMG detector, EEG detector, an EKG detector, an ECG detector, a bio-impedance sensor, an electromagnetic detector, an ultrasonic detector, an optical detector, a differential amplifier, an accelerometer, a video camera, a sound transducer, a digital stethoscope. The digital monitoring agent comprises one of: a Hidden Markov Model (HMM) recognizer, a dynamic time warp (DTW) recognizer, a neural network, a fuzzy logic engine, a Bayesian network, an expert system, a rule-driven system. The agent monitors user activity without requiring the sensor to be worn on the body. The agent monitors cooking appliances for a hazardous condition and shuts down the appliances using the mesh network. An in-door positioning system communicates with one or more mesh network appliances to provide location information. A call center coupled to the appliance to provide a human response. A web server coupled to the mesh network and to the POTS to provide information to an authorized remote user. A wireless router coupled to the mesh network and wherein the wireless router comprises one of: 802.11 router, 802.16 router, WiFi router, WiMAX router, Bluetooth router, X10 router. A mesh network appliance coupled to a power line to communicate X10 data to and from the mesh network. The appliance transmits and receives voice from the person over the mesh network. Bioimpedance data can be used to determine one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss, heart attack, stroke attack. A patch having second BI or EKG sensor in communication with the wireless transceiver. The appliance transmits and receives voice from the person over the mesh network to one of: a doctor, a nurse, a medical assistant, a caregiver, an emergency response unit, a family member. The system can store and analyze patient information such as medicine taking habits, television viewing habits, radio listening habits, eating and drinking habits, sleeping habits, or excise habits. A housing having one or more bioelectric contacts can be placed on the patient, the housing selected from one of: a patch, a wrist-watch, a band, a wristband, a chest band, a leg band, a sock, a glove, a foot pad, a head-band, an ear-clip, an ear phone, a shower-cap, an armband, an ear-ring, eye-glasses, sunglasses, a belt, a sock, a shirt, a garment, a jewelry, a bed spread, a pillow cover, a pillow, a mattress, a blanket, each having one or more sensors in communication with the wireless mesh network.

In another aspect, a method to monitor a person includes capturing and transmitting the person's daily activities over a wireless mesh network; determining a pattern associated with the person's daily activities; and requesting assistance if the person's current activity varies from the pattern or if a dangerous condition is detected.

In implementations, the method includes attaching a housing having one or more bioelectric contacts coupleable to the person, the housing selected from one of: a patch, a wristwatch, a band, a wristband, a chest band, a leg band, a sock, a glove, a foot pad, a head-band, an ear-clip, an ear phone, a shower-cap, an armband, an ear-ring, eye-glasses, sunglasses, a belt, a sock, a shirt, a garment, a jewelry, a bed spread, a pillow cover, a pillow, a mattress, a blanket, each having one or more sensors in communication with the wireless mesh network. The method includes detecting a weakness in left half and right half of the person's body; a walking pattern for loss of balance or coordination; requesting hands/feet movement in a predetermined pattern and reading accelerometer output in accordance with the predetermined pattern; checking whether the person experienced dizziness or headache; displaying a text image and asking the person to read back the text image one eye at a time; using a speech recognizer to detect confusion, trouble speaking or understanding; and asking the person if numbness is felt in the body.

In another aspect, a monitoring system for a person includes one or more wireless nodes and a stroke sensor coupled to the person and the wireless nodes to determine a stroke attack. In another aspect, a monitoring system for a person includes one or more wireless nodes and an electromyography (EMG) sensor coupled to the person and the wireless nodes to determine a stroke attack. In yet another aspect, a health care monitoring system for a person includes one or more wireless nodes forming a wireless mesh network; a wearable appliance having a sound transducer coupled to the wireless transceiver; and a bioelectric impedance (BI) sensor coupled to the wireless mesh network to communicate BI data over the wireless mesh network. In a further aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth. In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected. In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

Advantages of the system may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the patterns and/or images and human involvement is allowed only under pre-designated events. The system allows skilled doctors, nurses, physical therapists, family members, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The system reduces costs by automating data collection and compliance monitoring. Regular monitoring of the basic wellness parameters provides significant benefits in helping to capture adverse events sooner, reduce hospital admissions, and improve the effectiveness of medications, hence, lowering patient care costs and improving the overall quality of care. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improved the Quality of Care for the patient.

BRIEF DESCRIPTION OF THE DRAWINGS

FIG. 3 shows an exemplary process for monitoring the person.
FIG. 4 shows another exemplary for monitoring the person.
FIG. 5 illustrates yet another exemplary process for monitoring the person.
FIGS. 8-14 show various exemplary wearable appliances to monitor a patient.
FIGS. 16C-E shows exemplary stroke determination processes.
FIGS. 17B-C show exemplary EMG graphs of a patient.

DESCRIPTION

Figure 1:
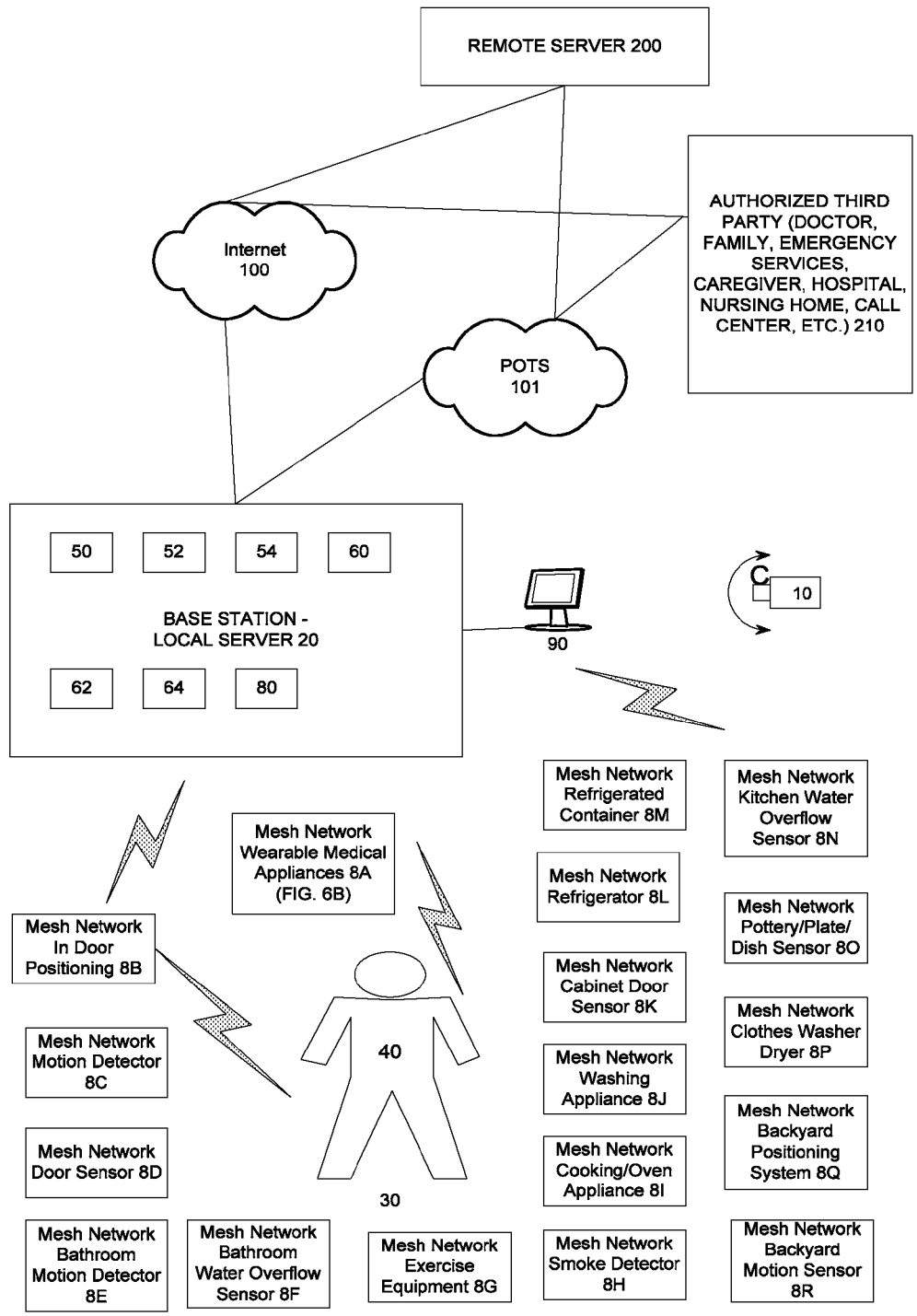
FIG. 1A illustrates an exemplary system for monitoring a person.
FIG. 1B shows an exemplary motion detector.
FIG. 1C shows an exemplary PIR motion detector.

FIG. 1A shows an exemplary mesh network patient monitoring system. The system can operate in a home, a nursing home, or a hospital. In this system, one or more mesh network appliances 8 are provided to enable wireless communication in the home monitoring system. As shown in FIG. 1A, a mesh network of sensors 8A-8R is shown. One implementation of mesh network is a ZigBee mesh network, which is discussed in more details in FIG. 2 below. ZigBee is built on an Institute of Electrical and Electronics Engineers (IEEE) global standard, 802.15.4, similar to the standards that govern Bluetooth and Wi-Fi. Open standards encourage innovation and competition, which bring down costs. Unlike Bluetooth and Wi-Fi networks, which require central hubs that distribute information to dispersed devices, ZigBee allows devices to form mesh networks, where each unit can relay information to its neighbors. Mesh networks are more robust than their hub-and-spoke counterparts; if a node breaks down, other nodes can automatically reroute transmissions around it. Mesh networking could let ZigBee systems link as many as 64,000 devices; Bluetooth networks, by contrast, are limited to just eight.

The mesh network includes one or more mesh network wearable medical appliances 8A which can monitor physiological measurements such as EKG, EMG, EEG, bioimpedance sensor, heart rate sensor, blood pressure sensor, or insulin sensor, among others. More details on these devices are described in commonly owned, co-pending applications that are incorporated by reference above. Appliances 8A in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or base station server 20 by way of a wireless radio frequency (RF) link using a proprietary or non-proprietary protocol.

The mesh network includes an in-door positioning 8B. The system has two or more wireless mesh network nodes that communicate with a mobile mesh network node. The radio signal strength indication (RSSI) is used to determine distance between two nodes, and triangulation is used to determine position. A localization process can be used to improve the position determination. In one embodiment, the mobile node periodically sends out packets containing RSSI and accelerometer data. The other two nodes receive the packets. After a packet is successfully received, RF signal strength RSSI reading is determined. The resulting signal strength measurements from the fixed sensing nodes are used to determine the wearer's location. Due to uncertainty associated with noisy data and the signal strength's nonlinearity, a probabilistic Monte Carlo localization technique to implement a particle filter to localize the location. Particle filters work by first distributing random samples called particles over the space being observed. Each particle represents a possible physical location in the environment. A probability value is assigned to each particle. This probability represents the likelihood that the person is at the location specified by the particle. At each time step, each particle is reevaluated and its probability value is updated according to the ZigBee signal strength measurements. Less likely particles are then redistributed around more likely particles. This is done by building a cumulative sum graph of the normalized probabilities of each particle. This graph is then randomly sampled to create a histogram that dictates where the particles should be distributed at the next time step. The particles concentrate around locations that have a higher probability of being the person's location. After the particles have their new coordinates, a small amount of random noise is added to each particle's location so that they're distributed around likely locations instead of concentrating at a single point. The location of the person resides at the intersection of two imaginary spheres centered at each of the sensing nodes, with radii proportional to the signal strength.

The in-door positioning system 8B links one or more mesh network appliances to provide location information. Inside the home or office, the radio frequency signals have negligible multipath delay spread (for timing purposes) over short distances. Hence, radio strength can be used as a basis for determining position. Alternatively, time of arrival can be used to determine position, or a combination of radio signal strength and time of arrival can be used. Position estimates can also be achieved in an embodiment by beamforming, a method that exchanges time-stamped raw data among the nodes. While the processing is relatively more costly, it yields processed data with a higher signal to noise ratio (SNR) for subsequent classification decisions, and enables estimates of angles of arrival for targets that are outside the convex hull of the participating sensors. Two such clusters of ZigBee nodes can then provide for triangulation of distant targets. Further, beamforming enables suppression of interfering sources, by placing nulls in the synthetic beam pattern in their directions. Another use of beamforming is in self-location of nodes when the positions of only a very small number of nodes or appliances are known such as those sensors nearest the wireless stations. In one implementation where each node knows the distances to its neighbors due to their positions, and some small fraction of the nodes (such as those nearest a PC with GPS) of the network know their true locations. As part of the network-building procedure, estimates of the locations of the nodes that lie within or near the convex hull of the nodes with known position can be quickly generated. To start, the shortest distance (multihop) paths are determined between each reference node. All nodes on this path are assigned a location that is the simple linear average of the two reference locations, as if the path were a straight line. A node which lies on the intersection of two such paths is assigned the average of the two indicated locations. All nodes that have been assigned locations now serve as references. The shortest paths among these new reference nodes are computed, assigning locations to all intermediate nodes as before, and continuing these iterations until no further nodes get assigned locations. This will not assign initial position estimates to all sensors. The remainder can be assigned locations based on pairwise averages of distances to the nearest four original reference nodes. Some consistency checks on location can be made using trigonometry and one further reference node to determine whether or not the node likely lies within the convex hull of the original four reference sensors.

In two dimensions, if two nodes have known locations, and the distances to a third node are known from the two nodes, then trigonometry can be used to precisely determine the location of the third node. Distances from another node can resolve any ambiguity. Similarly, simple geometry produces precise calculations in three dimensions given four reference nodes. But since the references may also have uncertainty, an alternative procedure is to perform a series of iterations where successive trigonometric calculations result only in a delta of movement in the position of the node. This process can determine locations of nodes outside the convex hull of the reference sensors. It is also amenable to averaging over the positions of all neighbors, since there will often be more neighbors than are strictly required to determine location. This will reduce the effects of distance measurement errors.

Alternatively, the network can solve the complete set of equations of intersections of hyperbola as a least squares optimization problem.

In yet another embodiment, any or all of the nodes may include transducers for acoustic, infrared (IR), and radio frequency (RF) ranging. Therefore, the nodes have heterogeneous capabilities for ranging. The heterogeneous capabilities further include different margins of ranging error. Furthermore, the ranging system is re-used for sensing and communication functions. For example, wideband acoustic functionality is available for use in communicating, bistatic sensing, and ranging. Such heterogeneous capability of the sensors 40 can provide for ranging functionality in addition to communications functions. As one example, repeated use of the communications function improves position determination accuracy over time. Also, when the ranging and the timing are conducted together, they can be integrated in a self-organization protocol in order to reduce energy consumption. Moreover, information from several ranging sources is capable of being fused to provide improved accuracy and resistance to environmental variability. Each ranging means is exploited as a communication means, thereby providing improved robustness in the presence of noise and interference. Those skilled in the art will realize that there are many architectural possibilities, but allowing for heterogeneity from the outset is a component in many of the architectures.

Figure 1B:
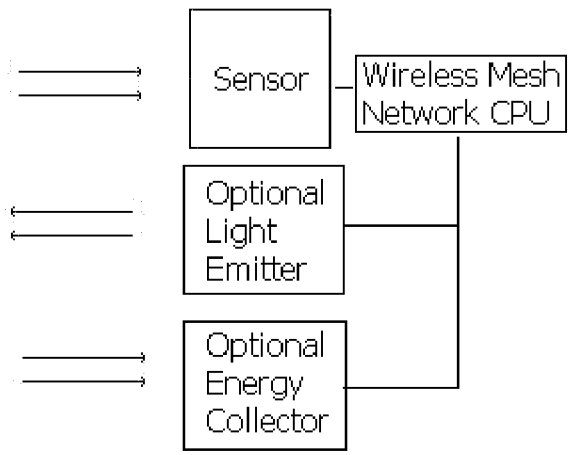

A mesh network motion detector 8C can be used in the network. FIG. 1B shows an exemplary system that includes an active or passive motion sensor connected to a wireless mesh network processor. For certain applications such as night guide light, the wireless mesh network processor can control an optional light emitter such as a light bulb or LED array for evening lighting purposes when motion is detected. For ease of placement, the system can include an energy collector or harvester device such as a solar cell to power the entire system.

The motion sensors can be grouped into two categories. The first are passive devices, such as PIR systems, stereoscopic vision and swept-focus ranging systems. The second are active devices, such as laser, microwave and ultrasonic range finding systems.

In one embodiment, the sensor can be an ultrasonic ranging device such as a Polaroid ranging module. This device is an active time-of-flight device developed for their cameras to allow automatic camera focusing. It determines the range to a target by measuring elapsed time between the transmission of a "chirp" of pulses and a detected echo. The one millisecond chirp consists of four discrete frequencies composed of 8 cycles at 60 KHz, 8 cycles at 56 KHz, 16 cycles at 52.5 KHz, and 24 cycles at 49.41 KHz. This pulse train increases the probability of signal reflection from a wide range of targets.

In another embodiment, the motion sensor can be a radio detection and ranging (RADAR) K-Band microwave RF (radio frequency) transmitter whose signal gets reflected by the target person. The reflected signal will have a Doppler shift proportional to the target speed. This Doppler frequency shift is detected in the receiver, amplified, filtered, and then digitized in an analog-to-digital converter (ADC), and passed onto the digital signal processing (DSP) chip. The DSP chip filters out false and low-level return signals to identify the speed of the person. The speed, along with various statistics and averages, is then sent over the wireless mesh network. In one implementation, the sensor sends out high frequency (such as 24 GHz) radio waves and measures the difference between the signal it transmitted and the signal bounced back to it and relays this information to the DSP to determine the speed of the individual. In yet another embodiment, a microwave signal is used to detect motion.

Figure 1C:
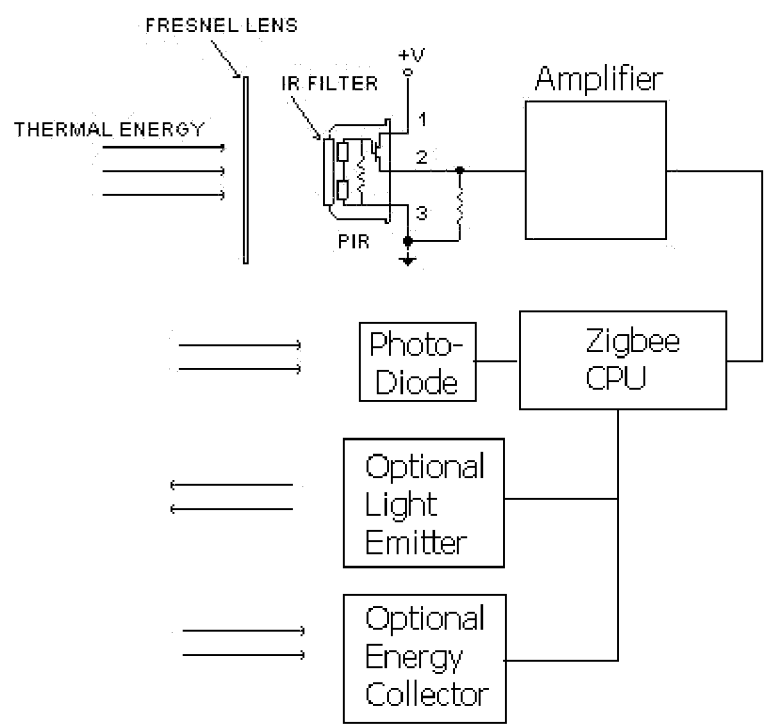

FIG. 1C shows one implementation of a PIR motion sensor. A pyroelectric sensor is used with a crystalline material that generates a surface electric charge when exposed to heat in the form of infrared radiation. When the amount of radiation striking the crystal changes, the amount of charge also changes and can then be measured with a sensitive FET device built into the sensor. The sensor has two sensing elements connected in a voltage bucking configuration. This arrangement cancels signals caused by vibration, temperature changes and sunlight. A body passing in front of the sensor will activate first one and then the other element whereas other sources will affect both elements simultaneously and be cancelled. The radiation source must pass across the sensor in a horizontal direction when sensor pins 1 and 2 are on a horizontal plane so that the elements are sequentially exposed to the IR source. The FET source terminal pin 2 connects through a pulldown resistor of about 100 K to ground and feeds into a two stage amplifier having signal conditioning circuits. The amplifier is typically bandwidth limited to below 10 Hz to reject high frequency noise and is followed by a window comparator that responds to both the positive and negative transitions of the sensor output signal. A filtered power source of from 3 to 15 volts should be connected to the FET drain terminal pin 1. One exemplary device is the RE200B PIR sensor and an exemplary module is the QK76 PIR Motion Detector Module, available from Q Kits Ltd. Of Kingston Ontario, whose output is an active high pulse of approximately 0.5 seconds and remains active as long as there is motion. A focusing lens is used in front of the sensor to focus thermal energy. The output of the sensor is provided to an amplifier, which output is provided to a mesh network wireless chip such as a single chip ZigBee transceiver with processor available from Freescale or Texas Instrument (ChipCon). The ZigBee chip can receive data from a photodiode and control a light emitter (such as LED array or light bulb) to provide night lighting in one option. This embodiment can also optionally harvest solar energy to charge the device when light is available.

A combination of active and passive motion sensors can be used for the mesh network motion detector 8C. They inject energy (light, microwaves or sound) into the environment in order to detect a change. In one embodiment, a beam of light crosses the room near the door, and a photosensor on the other side of the room detects the beam. When a person breaks the beam, the photosensor detects the change in the amount of light and sends a signal over the mesh network. In another embodiment, a radar detects when someone passes near the door. The radar sends out a burst of microwave radio energy and waits for the reflected energy to bounce back. When a person moves into the field of microwave energy, it changes the amount of reflected energy or the time it takes for the reflection to arrive, and the radar sends a signal over the mesh network to indicate a person is crossing the zone and optionally opens the door. Similarly, an ultrasonic transducer can be used to send sound waves, bouncing them off a target and waiting for the echo.

Passive motion sensors can be used as well. In one embodiment, the motion sensing such as those on lights (and security systems) is a passive system that detects infrared energy. These sensors are known as PIR (passive infrared) detectors or pyroelectric sensors. The sensor is sensitive to the temperature of a human body which has a skin temperature of about 93 degrees F. and radiates infrared energy with a wavelength between 9 and 10 micrometers. Therefore, the sensors are typically sensitive in the range of 8 to 12 micrometers. The sensor can be a photo-sensor—the infrared light bumps electrons off a substrate, and the electrons are detected and amplified into a signal that is then sent over the mesh network to the controller. The sensor looks for a rapid change in the amount of infrared energy. When a person walks by, the amount of infrared energy in the field of view changes rapidly and is detected. The motion sensor can be a wide field of view by using suitable lens covering the sensor to focus and bend light through plastic lenses.

In a basic embodiment, a single motion sensor 8C can be placed between the bed of the user and the bathroom. In a case where only a door sensor 8D is provided within the system, the door sensor 8D can be placed on the door of the bathroom. Such basic configuration can determine whether the user being monitored has gotten out of bed or has gone to the bathroom after a predetermined time. The daily living activity is captured and the information is captured for pattern analysis by the base station 20. For example, the pattern analysis can determine if the user remains in bed a specified length of time beyond the usual waking time or has not gone from the bed to the bathroom for a predetermined time period. If an abnormal lack of user activity is determined, the system can request the third-party 210 to take preventive action. A status report can be sent to the third party 210 indicating a potential problem with the patient.

A mesh network door sensor 8D can transmit door opening/closing to the base station 20. The door sensor can be magnetic sensors, or can be a wire that complete a circuit when the door is closed, can be an optical beam that is interrupted when the door moves, a reed-switch that detects door movement, or can be any suitable method to detect door opening or closing. The system can also be applied to windows to detect window opening and closing.

A mesh network bathroom motion detector 8E is provided to detect motions within a specific room, in this case a bathroom. Room specific sensors such as a mesh network bathroom water overflow sensor 8F can be provided. In one embodiment, a pair of wires is positioned on the bathroom floor and when liquid shorts the wires, a signal is sent over the mesh network to indicate bathtub overflow problem. Other room specific sensors can include a toilet sensor (not shown). The toilet sensor can simply detect lid opening/closing operations. In another implementation, the toilet sensor can include piezoelectric sensors that sense the viscosity of the patient excrements. In yet other implementations, the toilet sensor includes temperature sensor or other chemical analyzers that determine the composition or indicators thereof and forward the information over the mesh network.

The system also receives information from mesh network enabled exercise equipment 8G. Data transmitted by the equipment can include the length of the exercise, the type of exercise, the calories burned, the distance exercised, and the heart rate, among others.

The system can receive information from mesh network smoke detector or fire alarm device 8H. In one embodiment, if the smoke detector 8H detects a fire, the smoke detector 8H can turn on the lights on the floor that guide the patient to safety.

The system can also monitor cooking related activities. In one embodiment, a kitchen motion sensor is used. A mesh network cooking or oven appliance 8I transmits cooking duration and temperature and other parameters to the base station 20 for monitoring in case the patient accidentally left the oven or cooking device on. A mesh network washing appliance 8J can provide washing duration and completion time to the base station 20. Further, a mesh network cabinet door sensor 8K can provide usage data for certain important items in a cabinet (such as medication, among others). A mesh network refrigerator 8L provides information such as opening/closing of the refrigerator and other useful data such as type and remaining quantity of items in a particular refrigerated container 8M. The kitchen can also incorporate a kitchen water overflow sensor 8N near the sink. A mesh network pottery/plate/dish sensor 8O can be used to monitor if the patient is using these items on a frequent basis.

When an oven/stove safety detector module or software on the base station 20 receives information indicating that the oven or stove is on from sensor 8I, the system determines whether the oven or stove should be turned off. For example, if the patient is sleeping on a bed or sofa and the oven is on for an extended period of time, the base station 20 can instruct the mesh network oven appliance 8I to reduce the heat and page the patient. If the patient answers the page, the system can display the oven condition and request patient instruction. If the patient does not respond or respond with instruction to turn off the oven, the base station 20 can instruct the appliance 8I to turn off the oven. The system can also receive data from a cloth washer/dryer 8P to determine usage.

For the backyard, a mesh network positioning system 8Q can be used. Additionally, a backyard motion sensor 8R can communicate data over the mesh network for security as well as safety monitoring purposes.

In one heterogeneous sensor network embodiment, ZigBee nodes are used for local data communication, and high through put WiFi nodes are used to improve sensor network performance and reduce the nodes' energy consumption by offloading some of the wireless responsibilities to devices that can be plugged into power sources. The structure is analogous to a highway overlaid on a roadway system. Sensor data can then enter and exit the 802.11 highway at multiple interchanges in order to bypass the side roads, the wireless ZigBee nodes to increase bandwidth and reduce energy on average because the nodes are not solely responsible for moving data through the network.

Other appliances can be a bed spread or couch cover that includes a pressure transducer to detect a person sitting on the bed or couch. Another embodiment uses a simple contact switch that is depressed when the person sits on the bed or couch. The device can also be placed under chairs to detect sitting at a table. The pressure transducer or contact switch is connected to a mesh network processor/transceiver to transmit each occurrence when the user sits on a chair or rests on the bed. Based on the contact switch(es), the system can determine how long the user lies on the bed, and based on EEG sensors on the sheet, the system can determine how long the user sleeps and the quality of the sleep.

In another embodiment, a pressure transducer can be provided on a chair that measure the user's weight each time he or she uses the chair. Similarly, a bed transducer or scale can be provided to capture the user's weight and transmit the weight data over the mesh network. For a bed scale, two beam shaped load cells are provided at two ends of the bed along with support bars. The total weight is thus distributed over these two beams. The beam shaped load cell has a deflectable beam portion. Strain transducers for measuring deflection of the beam portion are located inside the beam portion. The strain transducer communicates its portion of the total weight to the mesh network weight processor. The bed scale is adjusted to compensate for the weight of the bed and the mattress. When the individual rests on the bed, the total weight is taken and the empty weight of the bed and mattress is subtracted to arrive at the weight of the individual person. Similarly, for a chair scale, each leg of the chair rests on a load cell with a deflectable beam portion. The total weight is thus distributed over the four leg beams.

The beam shaped load cell has a deflectable beam portion. Strain transducers for measuring deflection of the beam portion are located inside the beam portion. The strain transducer communicates its portion of the total weight to the mesh network weight processor. The chair scale is adjusted to compensate for the weight of the chair. When the individual sits on the chair, the total weight is taken and the empty weight of the chair is subtracted to arrive at the weight of the individual person.

In another embodiment, a temperature sensor can be provided on the chair, sofa, couch, or bed to detect the temperature of the patient and transmit the information over the mesh network.

In another embodiment, ZigBee sensors are placed along with light switches. When the user turns on the light in a room, the activity is recorded along with the coordinate of the switch. Such fixed location information is useful in fine tuning or recalibrating the in-door position sensor 8B. The light switches can be powered by an energy harvester such as a piezoelectric device that is energized by the flip of the switch. Alternatively, solar cell can be used to power the circuitry associated with the switches.

In another embodiment, sensors can be placed on the stairs to determine the stair climbing pace of the user and track his/her performance to detect if there are cardiovascular problems. For example, stroke victims can take longer to climb a stair case. In one embodiment, a light sensor and a light beam can be placed at the top and bottom of a stair case and when the beam is interrupted, the system can record the time required to go up-stair or down-stair.

The mesh network also covers entertainment devices such as ZigBee enabled televisions and stereo equipment. Thus, the type of entertainment enjoyed by the patient can also be monitored by the mesh network. Interactive TV responses or alternatively TV channel flipping/switching can be monitored by system to sense the alertness of the user. If the user turns on the TV, but shows no motion for an extended period of time, this can be viewed as potential stroke problem where the viewer is extremely passive when he/she normally is much more active.

Figure 2:
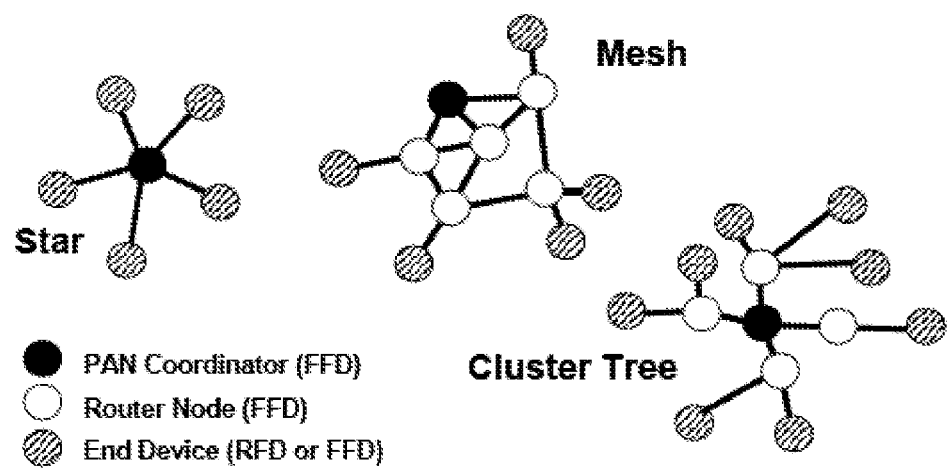
FIG. 2 shows an exemplary mesh network.

Appliances 8A-8R in the mesh network can include home security monitoring devices, door alarm, window alarm, home temperature control devices, fire alarm devices, among others. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15.4 network. More details of the mesh network is shown in FIG. 2 and discussed in more detail below.

The system can be used to monitor and assist elderly persons, functionally impaired persons or the like on a temporary short-term basis or on a long-term basis. The base station 20 is linked to various mesh network sensors provided within a number of activity detectors 8A-8R. Activity detectors 8A-8R monitor various activities of daily living of the user of the monitoring system. The base station 20 has a DAA to interface a voice communication circuit to the POTS 101 so that the user can wirelessly communicate with the authorized third party such as a call center without having to walk to a speaker phone. The base station 20 can also store voicemail and other messages such as pill reminder messages and play the messages for the user.

The patient monitoring system integrates sensor data from different activity domains to make a number of determinations at predetermined times on a twenty-four hour basis. One activity domain determination within the patient monitoring system includes movement of the person being monitored. In this movement domain determinations are made by the indoor position sensor 8B and/or the motion detector 8C to determine whether the user is up and around. Another activity domain determination is medication compliance where the system determines whether the user is following a predetermined medication regimen by detecting pill unit opening or closure. The system can also monitor dangerous conditions such as to whether a cooking range or stove has been left on inappropriately by querying mesh network controllers in the cooking range, stove, or cooking appliance. Other systems may include, for example, other potentially harmful appliances such as heaters, irons or electric space heaters.

The system of sensors the patient monitoring system can determine, for example, whether users are up and about in their homes and whether they are having difficulty managing their medications. It can also be determined whether the user has accidentally left a stove on or has failed to get out of bed a predetermined number of hours after a usual waking time. If the patient monitoring system detects any of these or other problems it can then first page the user on the wearable device such as wrist watch to provide a reminder about the medications, stove, or other detected problems. If the patient does not respond, the system elevates the issue to the authorized third party 210.

The system can track the activities of the patient and distribute specialized gerontological daily activity summary reports to users, family members, case managers, physicians and others. It also makes it possible to collect and act upon the designated priority information which may indicate immediate problems for the user. The system can generate periodic reports which may include collections, compilations and arrangements of information on any or all of the monitored activities within the user's living area. These electronic records may be used in combination with any other information to produce any type of periodic activity reports desired on the user being monitored. These user activity reports may be used by a professional case manager or a designated family member to determine if the user is experiencing problems with specific activities of daily living. Thus these problems may be dealt with before they become a threat to the continued well being of the user and the ability of the user to live independently. Furthermore, in addition to providing remote case monitoring and in-home reminders, the patient monitoring system may be programmed to take corrective actions when certain problems are detected. A social worker, health professional or designated family member can query the base station 20 or can respond to the transmitted information according to a predetermined protocol.

The system can provide case management that may monitor approximately a plurality of distributed clients. The system can receive information from the distributed patient monitoring systems on an immediate basis or at predetermined time intervals. For example, the remote case monitoring system may receive information on an hourly, daily or weekly basis. If the patient's local base station 20 determines that a potential problem exists, the base station 20 forwards the request to the server 200 running the case management software, and this event may be brought to the immediate attention of the human case monitor at a call center, for example, by means of a computer screen. The remote case manager may examine individual case and data records for the client being monitored to learn the predetermined response for the monitored person when the reported event occurs. Likely interventions required of personnel at the case management site may include calling a local case manager, a hospital social worker or a local next of kin. Other actions the remote case monitor may execute include calling the user, remotely downloading the last twenty-four or forty-eight hours worth of event summary information from the local patient monitoring system and remotely initiating a diagnostic sequence on the local patient monitoring system. The protocol of procedures for intervention by the remote case monitor may differ from one remote case monitor system to another and from one user to another. It is anticipated in the preferred embodiment of the invention that various intervention decisions such as who to call when predetermined events occur and what messages to deliver may be carried out by a machine intelligence expert system (not shown) at the remote case monitoring system or by a person or a combination of both. The local patient monitoring system may also be programmed to carry out such decisions as who to call when appropriate. For example, the patient monitoring system may have a contact list of people to contact in various emergencies. In addition to receiving and interpreting data indicating the need for intervention in event of emergencies, the remote case monitoring software on the server 200 routinely receives downloaded data from individual patient monitoring systems 20 at predetermined intervals. This data is interpreted on the individual and aggregate level by means of trend analysis software which detects larger than statistically normal deviations from event pattern measurements. The remote case monitoring system on the server 200 may use this analysis to produce periodic summary reports of events relating to everyday living tasks in the home environment of the user. More specifically these reports may be used to detect certain event classes, to weight them in terms of their relative importance and to compare them with baselines of task performance. The events weighed with respect to their importance may include getting out of bed, managing medication, the proper control of a stove, the proper control of water flow, and the proper control of selected electrical appliances. Based upon the reports of these events, gerontological living summary reports may be prepared in machine form and paper form at the remote case management software for distribution to pre-designated parties involved in the case management of the patient. These parties may include the users themselves, relatives of the user, case manager social workers, physicians and other appropriate formal and informal providers. The system can produce trend analysis reports which show the frequency of occurrence of different events over a predetermined time period such as six months. Thus the trend analysis report might show that over the course of six months the user became increasingly noncompliant with medications and/or increasingly likely to leave the stove on inappropriately. Using a known trend analysis technique, software driven reports can detect increasing frequencies of problems of every day activities. The trend analysis report may be a monthly paper or machine report which provides several indicators of performance on different areas of everyday living monitored by the patient monitoring system. These areas may include waking and sleeping, medication management, stove management, water flow management and the operation of additional appliances. The raw data for this report is based on the event log data transferred from the base station 20 or the server 200 using standard data transfer and priority specific modes. The trend analysis report can plot deviations in behavior indicating changes in plot trend. For example, the trend analysis report can plot waking and sleeping hours and the number of times a user goes to the bathroom. While none of this in itself indicates a situation requiring intervention, sudden changes in sleep habits, bathroom use, even appliance use may indicate sudden changes in health or cognitive well being requiring a relative or a case management social worker or case management social worker or a physician to visit or interview the user. While any number of combinations of interpreted data can be used in any number of specialized reports, it is anticipated that most case management sites and most relatives would want to know the frequency and severity of specific errors, the extent and accuracy of medication compliance and whether a waking or sleeping pattern of a user is changing radically. The trend analysis report provides case managers and relatives with this information and enables them to better help the user by locating subtle changes in behavior patterns, monitoring various kinds of potentially dangerous errors and keeping a record of baseline functioning in relation to monitored activities.

For patients whose safety concerns outweigh privacy issue, a plurality of monitoring cameras 10 may optionally be placed in various predetermined positions in a home of a patient 30. The cameras 10 can be wired or wireless. For example, the cameras can communicate over infrared links or over radio links conforming to the 802X (e.g. 802.11A, 802.11B, 802.11G, 802.15) standard or the Bluetooth standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliance 8 detects that the user needs assistance or that an emergency had occurred.

The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

The patient 30 may wear one or more wearable patient monitoring appliances such as wrist-watches or clip on devices or electronic jewelry to monitor the patient. One wearable appliance such as a wrist-watch includes sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others. In the HMM embodiment, user activities are automatically classified and any variance from the usual pattern is flagged for monitoring by the authorized third party 210. In another embodiment, a Bayesian network is used to analyze and automatically build user ambulatory patterns to check if the user is not acting "normally."

As shown in FIG. 3, pseudo-code for one embodiment of a pattern recognizer to assist the patient is as follows:
 Build pattern of daily activities
 Do
  Detect if the user's daily activities are within a predetermined threshold of normal activities
  Check that medication cabinet has been accessed on daily basis
  Check door/window is closed in the evening unless specified in advance
  Check that bathroom is not flooded
  Check that patient is not in bathroom for excessive amounts of time
  Check patient toilet for potential disease
  Check for normal usage of exercise equipment in accordance with doctor recommendations
  Check kitchen appliances to minimize risks of fire or flooding hazard
  Check cloth washer/dryer for usage activity
  Check refrigerator activity
  Check backyard motion sensor for intrusion and/or assistance that may be required if the user is injured in the backyard
  Check thermostat and heater/AC for temperature setting
  Check sleeping activities
  Check eating activities
  Check weight
  Check TV viewing or radio listening or computer usage habit Check traversing speed on stair
  If abnormality is detected, request assistance from authorized third party
  Update daily activity data structure
  Generate periodic summary/report/recommendations to person and authorized third parties
 Loop Through various software modules 50-80, the system monitors the behavioral patterns of the patient and can intervene if necessary. For example, the system can detect that the oven is on for an excessive amount of time and can turn off the oven using commands communicated over the mesh network. Authorized users 210 can see a display of the patient's activities on the screen using data securely transmitted over the Internet from the base station 20.

FIG. 4 shows an exemplary process to monitor a person. First, the process captures and transmits the person's daily activities over a wireless mesh network. The process determines a pattern associated with the person's daily activities. Next, the person or patient attaches a housing having one or more bioelectric contacts coupleable to the person, the housing selected from one of: a patch, a wristwatch, a band, a wristband, a chest band, a leg band, a sock, a glove, a foot pad, a head-band, an ear-clip, an ear phone, a shower-cap, an armband, an ear-ring, eye-glasses, sun-glasses, a belt, a sock, a shirt, a garment, a jewelry, a bed spread, a pillow cover, a pillow, a mattress, a blanket, each having one or more sensors in communication with the wireless mesh network. The system detects a weakness in left half and right half of the person's body; a walking pattern for loss of balance or coordination; requesting hands/feet movement in a predetermined pattern and reading accelerometer output in accordance with the predetermined pattern; checking whether the person experienced dizziness or headache; displaying a text image and asking the person to read back the text image one eye at a time; using a speech recognizer to detect confusion, trouble speaking or understanding; and asking the person if numbness is felt in the body. The process requests assistance from third party 210 if the person's current activity varies from the pattern or if a dangerous condition is detected so that assistance is rendered on a timely basis.

In one embodiment, data driven analyzers may be used to track the patient's daily living pattern. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient stoke patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's EEG, EKG, BI, ultrasound, optical, acoustic, electromagnetic, or electrical parameters are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences. Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user daily pattern. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the daily living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b(j) O(t) corresponds to the probability assigned by the model that the feature frame symbol is O(t). The model arrangement is a matrix A=[a(i,j)] of transition probabilities and a technique of computing B=b (j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

For one embodiment with video monitoring, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module 52 monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0, 0, 0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line.

A module monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that the patient had taken a bath or a shower. However, if a person falls and remains motionless for a predetermined period, the system would record the event and notify a designated person to get assistance.

Through a video viewing module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives data from the base station server 20 and passes the data to one or more remote servers 200. The images are transmitted from the server 200 over a secure communication link such as virtual private network (VPN) to the remote server(s) 200.

In one embodiment where cameras are deployed, the server 200 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 200 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

In the camera embodiment, the transactions between the server 200 and one of the remote servers 200 are detailed. The server 200 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64 k or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 200 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a microprocessor. The transceiver sends activation signals to and receives identification data from the tag. The antenna may be enclosed with the reader or located outside the reader as a separate piece. RFID readers communicate directly with the RFID tags and send encrypted usage data over the patient's network to the server 200 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

Various arrangements of medication holders and dispensers may be used. For example, the medications within a medication holder may be organized according to the time of day they are taken. In this type of organization medications which are taken at the same time may be loaded together into a single compartment within the medication holder. A plurality of these compartments may be provided. The opening and closing of these compartments may be monitored. Each medication batch (for example morning batch, evening batch) is associated with a code for identification purposes.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 20 can order these items automatically. The server 20 also monitors drug compliance, and if the patient does not remove the bottle to dispense medication as prescribed, the server 200 sends a warning to the healthcare provider.

The base station 20 can determine when user compliance does not conform to a scheduled regimen. After a selected time period, for example, one-half hour, without user compliance, a voice reminder can be sent to a voice enabled wristwatch to remind the user to take medications. These reminders and inquiries may be made with respect to all medications or with respect to specific medications. The base station 20 may also provide specific time scheduled reminders to take medication.

The database tracks typical arm and leg movements to determine whether the user is experiencing muscle weakness reflective of a stroke. If muscle weakness is detected, the system presents the user with additional tests to confirm the likelihood of a stroke attack. If the information indicates a stroke had occurred, the system stores the time of the stroke detection and calls for emergency assistance to get timely treatment for the stroke. The user's habits and movements can be determined by the system for stroke detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
| --- | --- | --- | --- |
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t)$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability $b(j) O(t)$ corresponds to the probability assigned by the model that the feature frame symbol is $O(t)$. The model arrangement is a matrix $A=[a(i,j)]$ of transition probabilities and a technique of computing $B=b(j) O(t)$, the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

In one embodiment, a wearable appliance can be used. The wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical 'check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding 'suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of appliances by the user. Data can be synchronized between the Repository and appliance(s) via the base station 20. The user can preview the readings received from the appliance(s) and reject erroneous readings. The user or treating professional can set up the system to generate alerts against received data, based on pre-defined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the base station server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the base station 20 and each appliance on initialization. In one embodiment, each appliance 8 transmits data to the base station 20 in an XML format for ease of interfacing and is either kept encrypted or in a non-readable format on the base station 20 for security reasons.

The base station 20 frequently collects and synchronizes data from the appliances 8. The base station 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others. In one embodiment, the base station server 20 serves a web page customized by the user or the user's representative as the monitoring center that third parties such as family, physicians, or caregivers can log in and access information. In another embodiment, the base station 20 communicates with the server 200 at a call center so that the call center provides all services. In yet another embodiment, a hybrid solution where authorized representatives can log in to the base station server 20 access patient information while the call center logs into both the server 200 and the base station server 20 to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

Due to its awareness of the patient's position, the server 200 can optionally control a mobility assistance device such as a smart cane or robot. The robotic smart cane sends video from its camera to the server 20, which in turn coordinates the position of the robot, as determined by the cameras 10 mounted in the home as well as the robot camera. The robot position, as determined by the server 20, is then transmitted to the robot for navigation. The robot has a frame with an extended handle. The handle includes handle sensors mounted thereon to detect the force places on each handle to receive as input the movement desired by the patient. In one embodiment, the robot has a control navigation system that accepts patient command as well as robot self-guidance command. The mobility is a result of give-and-take between the patient's self-propulsion and the walker's automated reactions. Thus, when the patient moves the handle to the right, the robot determines that the patient is interested in turning and actuates the drive systems appropriately. However, if the patient is turning into an obstacle, as determined by the cameras and the server 20, the drive system provides gentle resistance that tells the patient of an impending collision.

If, for example, a patient does not see a coffee table ahead, the walker will detect it, override the patient's steering to avoid it, and thereby prevent a possible fall. Onboard software processes the data from 180 degrees of approaching terrain and steers the front wheel toward openings and away from obstacles.

The control module executes software that enables the robot to move around its environment safely. The software performs localization, mapping, path planning and obstacle avoidance. In one embodiment, images from a plurality of wall-mounted cameras 10 are transmitted to the server 20. The server 20 collects images of the robot and triangulates the robot position by cross-referencing the images. The information is then correlated with the image from the robot-mounted camera and optical encoders that count the wheel rotations to calculate traveled distance for range measurement. In this process, a visual map of unique "landmarks" created as the robot moves along its path is annotated with the robot's position to indicate the position estimate of the landmark. The current image, seen from the robot, is compared with the images in the database to find matching landmarks. Such matches are used to update the position of the robot according to the relative position of the matching landmark. By repeatedly updating the position of landmarks based on new data, the software incrementally improves the map by calculating more accurate estimates for the position of the landmarks. An improved map results in more accurate robot position estimates. Better position estimates contribute to better estimates for the landmark positions and so on. If the environment changes so much that the robot no longer recognizes previous landmarks, the robot automatically updates the map with new landmarks. Outdated landmarks that are no longer recognized can easily be deleted from the map by simply determining if they were seen or matched when expected.

Using the obstacle avoidance algorithm, the robot generates corrective movements to avoid obstacles not represented in the path planner such as open/closed doors, furniture, people, and more. The robot rapidly detects obstacles using its sensors and controls its speed and heading to avoid obstacles.

The hazard avoidance mechanisms provide a reflexive response to hazardous situations to insure the robot's safety and guarantee that it does not damage itself or the environment. Mechanisms for hazard avoidance include collision detection using not one but a complementary set of sensors and techniques. For instance, collision avoidance can be provided using contact sensing, motor load sensing, and vision. The combination of multiple sources for collision detection guarantees safe collision avoidance. Collision detection provides a last resort for negotiating obstacles in case obstacle avoidance fails to do so in the first place, which can be caused by moving objects or software and hardware failures.

If the walker is in motion (as determined by the wheel encoder), the force applied to the brake pads is inversely proportional to the distance to obstacles. If the walker is stopped, the brakes should be fully applied to provide a stable base on which the patient can rest. When the walker is stopped and the patient wishes to move again, the brakes should come off slowly to prevent the walker from lurching forward.

The walker should mostly follow the patient's commands, as this is crucial for patient acceptance. For the safety braking and the safety braking and steering control systems, the control system only influences the motion when obstacles or cliffs are near the patient. In other words, the walker is, typically, fully patient controlled. For all other situations, the control system submits to the patient's desire. This does not mean that the control system shuts down, or does not provide the usual safety features. In fact, all of the control systems fall back on their emergency braking to keep the patient safe. When the control system has had to brake to avoid an obstacle or has given up trying to lead the patient on a particular path, the patient must disengage the brakes (via a pushbutton) or re-engage the path following (again via a pushbutton) to regain control or allow collaboration again. This lets the patient select the walker's mode manually when they disagree with the control system's choices.

FIG. 5 shows an exemplary process to monitor patient. First, the process sets up mesh network appliances (1000). Next, the process determines patient position using in-door positioning system (1002). The process then determines patient movement using accelerometer output (1004). Sharp accelerations may be used to indicate fall. Further, the z axis accelerometer changes can indicate the height of the appliance from the floor and if the height is near zero, the system infers that the patient had fallen. The system can also determine vital parameter including patient heart rate (1006). The system determines if patient needs assistance based on in-door position, fall detection and vital parameter (1008). If a fall is suspected, the system confirms the fall by communicating with the patient prior to calling a third party such as the patient's physician, nurse, family member, 911, 511, 411, or a paid call center to get assistance for the patient (1010). If confirmed or if the patient is non-responsive, the system contacts the third party and sends voice over mesh network to appliance on the patient to allow one or more third parties to talk with the patient (1012). If needed, the system calls and/or conferences emergency personnel into the call (1014).

In one embodiment, if the patient is outside of the mesh network range such as when the user is traveling away from his/her home, the system continuously records information into memory until the home mesh network is reached or until the monitoring appliance reaches an internet access point. While the wearable appliance is outside of the mesh network range, the device searches for a cell phone with an expansion card plugged into a cell phone expansion slot such as the SDIO slot. If the wearable appliance detects a cell phone that is mesh network compatible, the wearable appliance communicates with the cell phone and provides information to the server 200 using the cellular connection. In one embodiment, a Zigbee SDIO card from C-guys, Inc., enables device-to-device communications for PDAs and smart phones. C-guys' ZigBee SDIO card includes the company's CG-100 SDIO application interface controller, which is designed to convert an application signal to an SD signal (or vice versa). The ZigBee card can provide signal ranges of up to 10 m in the 2.4 GHz band and data rates of up to 200 kbps. The card has peer-to-peer communications mode and supports direct application to PDAs or any SD supported hand-held cell phones. In this embodiment, the PDA or cell phone can provide a GPS position information instead of the indoor position information generated by the mesh network appliances 8.

The cell phone GPS position information, accelerometer information and vital information such as heart rate information is transmitted using the cellular channel to the server 200 for processing as is normal. In another embodiment where the phone works through WiFi (802.11) or WiMAX (802.16) or ultra-wideband protocol instead of the cellular protocol, the wearable appliance can communicate over these protocols using a suitable mesh network interface to the phone. In instances where the wearable appliance is outside of its home base and a dangerous condition such as a fall is detected, the wearable appliance can initiate a distress call to the authorized third party using cellular, WiFi, WiMAX, or UWB protocols as is available.

Figure 6:
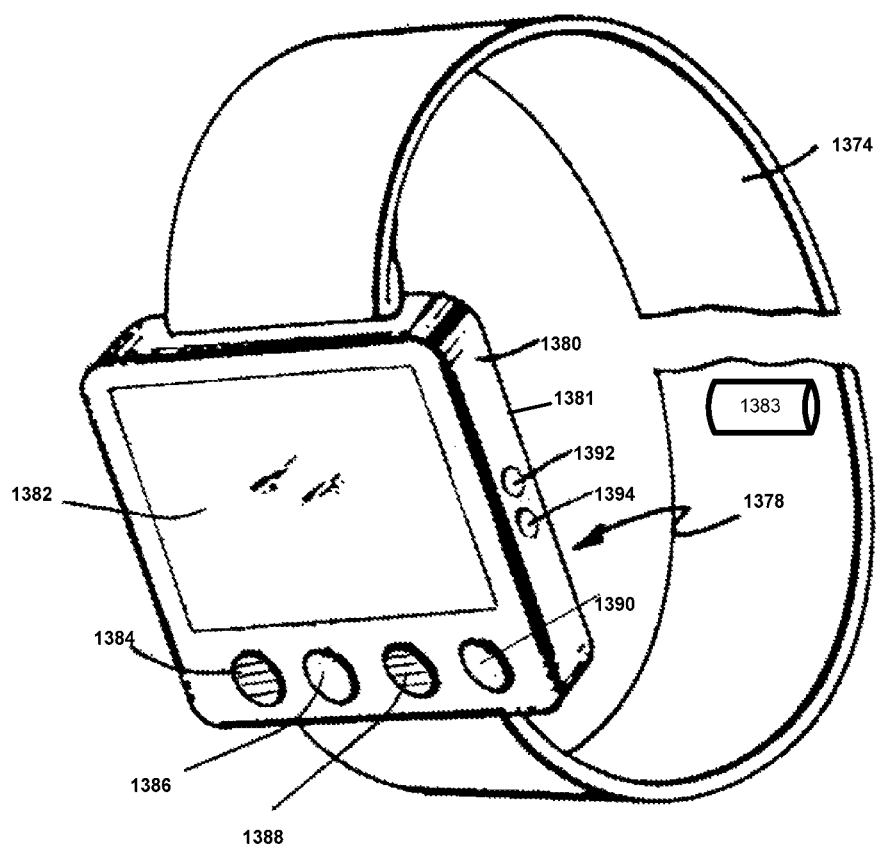
FIG. 6 shows an exemplary wrist-watch based assistance device.

FIG. 6 shows a portable embodiment of the present invention where the voice recognizer is housed in a wrist-watch. As shown in FIG. 6, the device includes a wrist-watch sized case 1380 supported on a wrist band 1374. The case 1380 may be of a number of variations of shape but can be conveniently made a rectangular, approaching a box-like configuration. The wrist-band 1374 can be an expansion band or a wrist-watch strap of plastic, leather or woven material. The processor or CPU of the wearable appliance is connected to a radio frequency (RF) transmitter/receiver (such as a Bluetooth device, a Zigbee device, a WiFi device, a WiMAX device, or an 802.X transceiver, among others.

In one embodiment, the back of the device is a conductive metal electrode 1381 that in conjunction with a second electrode 1383 mounted on the wrist band 1374, enables differential EKG or ECG to be measured. The electrical signal derived from the electrodes is typically 1 mV peak-peak. In one embodiment where only one electrode 1381 or 1383 is available, an amplification of about 1000 is necessary to render this signal usable for heart rate detection. In the embodiment with electrodes 1381 and 1383 available, a differential amplifier is used to take advantage of the identical common mode signals from the EKG contact points, the common mode noise is automatically cancelled out using a matched differential amplifier. In one embodiment, the differential amplifier is a Texas Instruments INA321 instrumentation amplifier that has matched and balanced integrated gain resistors. This device is specified to operate with a minimum of 2.7V single rail power supply. The INA321 provides a fixed amplification of 5× for the EKG signal. With its CMRR specification of 94 dB extended up to 3 KHz the INA321 rejects the common mode noise signals including the line frequency and its harmonics. The quiescent current of the INA321 is 40 mA and the shut down mode current is less than 1 mA. The amplified EKG signal is internally fed to the on chip analog to digital converter. The ADC samples the EKG signal with a sampling frequency of 512 Hz. Precise sampling period is achieved by triggering the ADC conversions with a timer that is clocked from a 32.768 kHz low frequency crystal oscillator. The sampled EKG waveform contains some amount of super imposed line frequency content. This line frequency noise is removed by digitally filtering the samples. In one implementation, a 17-tap low pass FIR filter with pass band upper frequency of 6 Hz and stop band lower frequency of 30 Hz is implemented in this application. The filter coefficients are scaled to compensate the filter attenuation and provide additional gain for the EKG signal at the filter output. This adds up to a total amplification factor of greater than 1000× for the EKG signal.

The wrist band 1374 can also contain other electrical devices such as ultrasound transducer, optical transducer or electromagnetic sensors, among others. In one embodiment, the transducer is an ultrasonic transducer that generates and transmits an acoustic wave upon command from the CPU during one period and listens to the echo returns during a subsequent period. In use, the transmitted bursts of sonic energy are scattered by red blood cells flowing through the subject's radial artery, and a portion of the scattered energy is directed back toward the ultrasonic transducer 84. The time required for the return energy to reach the ultrasonic transducer varies according to the speed of sound in the tissue and according to the depth of the artery. Typical transit times are in the range of 6 to 7 microseconds. The ultrasonic transducer is used to receive the reflected ultrasound energy during the dead times between the successive transmitted bursts. The frequency of the ultrasonic transducer's transmit signal will differ from that of the return signal, because the scattering red blood cells within the radial artery are moving. Thus, the return signal, effectively, is frequency modulated by the blood flow velocity.

A driving and receiving circuit generates electrical pulses which, when applied to the transducer, produce acoustic energy having a frequency on the order of 8 MHz, a pulse width or duration of approximately 8 microseconds, and a pulse repetition interval (PRI) of approximately 16 μs, although other values of frequency, pulse width, and PRI may be used. In one embodiment, the transducer 84 emits an 8 microsecond pulse, which is followed by an 8 microsecond "listen" period, every 16 microseconds. The echoes from these pulses are received by the ultrasonic transducer 84 during the listen period. The ultrasonic transducer can be a ceramic piezoelectric device of the type well known in the art, although other types may be substituted.

An analog signal representative of the Doppler frequency of the echo is received by the transducer and converted to a digital representation by the ADC, and supplied to the CPU for signal processing. Within the CPU, the digitized Doppler frequency is scaled to compute the blood flow velocity within the artery based on the Doppler frequency. Based on the real time the blood flow velocity, the CPU applies the vital model to the corresponding blood flow velocity to produce the estimated blood pressure value.

Prior to operation, calibration is done using a calibration device and the monitoring device to simultaneously collect blood pressure values (systolic, diastolic pressures) and a corresponding blood flow velocity generated by the monitoring device. The calibration device is attached to the base station and measures systolic and diastolic blood pressure using a cuff-based blood pressure monitoring device that includes a motor-controlled pump and data-processing electronics. While the cuff-based blood pressure monitoring device collects patient data, the transducer collects patient data in parallel and through the watch's radio transmitter, blood flow velocity is sent to the base station for generating a computer model that converts the blood flow velocity information into systolic and diastolic blood pressure values and this information is sent wirelessly from the base station to the watch for display and to a remote server if needed. This process is repeated at a later time (e.g., 15 minutes later) to collect a second set of calibration parameters. In one embodiment, the computer model fits the blood flow velocity to the systolic/diastolic values. In another embodiment, the computer trains a neural network or HMM to recognize the systolic and diastolic blood pressure values.

After the computer model has been generated, the system is ready for real-time blood pressure monitoring. In an acoustic embodiment, the transducer directs ultrasound at the patient's artery and subsequently listens to the echoes therefrom. The echoes are used to determine blood flow, which is fed to the computer model to generate the systolic and diastolic pressure values as well as heart rate value. The CPU's output signal is then converted to a form useful to the user such as a digital or analog display, computer data file, or audible indicator. The output signal can drive a speaker to enable an operator to hear a representation of the Doppler signals and thereby to determine when the transducer is located approximately over the radial artery. The output signal can also be wirelessly sent to a base station for subsequent analysis by a physician, nurse, caregiver, or treating professional. The output signal can also be analyzed for medical attention and medical treatment.

It is noted that while the above embodiment utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 84) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to be equivalent.

In one optical embodiment, the transducer can be an optical transducer. The optical transducer can be a light source and a photo-detector embedded in the wrist band portions 1374. The light source can be light-emitting diodes that generate red ($\lambda$~630 nm) and infrared ($\lambda$~900 nm) radiation, for example. The light source and the photo-detector are slidably adjustable and can be moved along the wrist band to optimize beam transmission and pick up. As the heart pumps blood through the patient's finger, blood cells absorb and transmit varying amounts of the red and infrared radiation depending on how much oxygen binds to the cells' hemoglobin. The photo-detector detects transmission at the predetermined wavelengths, for example red and infrared wavelengths, and provides the detected transmission to a pulse-oximetry circuit embedded within the wrist-watch. The output of the pulse-oximetry circuit is digitized into a time-dependent optical waveform, which is then sent back to the pulse-oximetry circuit and analyzed to determine the user's vital signs.

In the electromagnetic sensor embodiment, the wrist band 1374 is a flexible plastic material incorporated with a flexible magnet. The magnet provides a magnetic field, and one or more electrodes similar to electrode 1383 are positioned on the wrist band to measure voltage drops which are proportional to the blood velocity. The electromagnetic embodiment may be mounted on the upper arm of the patient, on the ankle or on the neck where peripheral blood vessels pass through and their blood velocity may be measured with minimal interruptions. The flexible magnet produces a pseudo-uniform (non-gradient) magnetic field. The magnetic field can be normal to the blood flow direction when wrist band 1374 is mounted on the user's wrist or may be a rotative pseudo-uniform magnetic field so that the magnetic field is in a transversal direction in respect to the blood flow direction.

The electrode output signals are processed to obtain a differential measurement enhancing the signal to noise ratio. The flow information is derived based on the periodicity of the signals. The decoded signal is filtered over several periods and then analyzed for changes used to estimate artery and vein blood flow. Systemic stroke volume and cardiac output may be calculated from the peripheral SV index value.

The wrist-band 1374 further contains an antenna 1376 for transmitting or receiving radio frequency signals. The wrist-band 1374 and the antenna 1376 inside the band are mechanically coupled to the top and bottom sides of the wrist-watch housing 1380. Further, the antenna 1376 is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing 1380 contains the processor and associated peripherals to provide the human-machine interface. A display 1382 is located on the front section of the housing 1380. A speaker 1384, a microphone 1388, and a plurality of push-button switches 1386 and 1390 are also located on the front section of housing 1380.

The electronic circuitry housed in the watch case 1380 detects adverse conditions such as falls or seizures. In one implementation, the circuitry can recognize speech, namely utterances of spoken words by the user, and converting the utterances into digital signals. The circuitry for detecting and processing speech to be sent from the wristwatch to the base station 20 over the mesh network includes a central processing unit (CPU) connected to a ROM/RAM memory via a bus. The CPU is a preferably low power 16-bit or 32-bit microprocessor and the memory is preferably a high density, low-power RAM. The CPU is coupled via the bus to processor wake-up logic, one or more accelerometers to detect sudden movement in a patient, an ADC 102 which receives speech input from the microphone. The ADC converts the analog signal produced by the microphone into a sequence of digital values representing the amplitude of the signal produced by the microphone at a sequence of evenly spaced times. The CPU is also coupled to a digital to analog (D/A) converter, which drives the speaker to communicate with the user. Speech signals from the microphone are first amplified, pass through an antialiasing filter before being sampled. The front-end processing includes an amplifier, a bandpass filter to avoid antialiasing, and an analog-to-digital (A/D) converter or a CODEC. To minimize space, the ADC, the DAC and the interface for wireless transceiver and switches may be integrated into one integrated circuit to save space. In one embodiment, the wrist watch acts as a walkie-talkie so that voice is received over the mesh network by the base station 20 and then delivered to a call center over the POTS or PSTN network. In another embodiment, voice is provided to the call center using the Internet through suitable VOIP techniques. In one embodiment, speech recognition such as a speech recognizer is discussed in U.S. Pat. No. 6,070,140 by the inventor of the instant invention, the content of which is incorporated by reference.

In one embodiment, the wireless nodes convert freely available energy inherent in most operating environments into conditioned electrical power. Energy harvesting is defined as the conversion of ambient energy into usable electrical energy. When compared with the energy stored in common storage elements, like batteries and the like, the environment represents a relatively inexhaustible source of energy. Energy harvesters can be based on piezoelectric devices, solar cells or electromagnetic devices that convert mechanical vibrations.

Power generation with piezoelectrics can be done with body vibrations or by physical compression (impacting the material and using a rapid deceleration using foot action, for example). The vibration energy harvester consists of three main parts. A piezoelectric transducer (PZT) serves as the energy conversion device, a specialized power converter rectifies the resulting voltage, and a capacitor or battery stores the power. The PZT takes the form of an aluminum cantilever with a piezoelectric patch. The vibration-induced strain in the PZT produces an ac voltage. The system repeatedly charges a battery or capacitor, which then operates the EKG/EMG sensors or other sensors at a relatively low duty cycle. In one embodiment, a vest made of piezoelectric materials can be wrapped around a person's chest to generate power when strained through breathing as breathing increases the circumference of the chest for an average human by about 2.5 to 5 cm. Energy can be constantly harvested because breathing is a constant activity, even when a person is sedate. In another embodiment, piezoelectric materials are placed in between the sole and the insole; therefore as the shoe bends from walking, the materials bend along with it. When the stave is bent, the piezoelectric sheets on the outside surface are pulled into expansion, while those on the inside surface are pushed into contraction due to their differing radii of curvature, producing voltages across the electrodes. In another embodiment, PZT materials from Advanced Cerametrics, Inc., Lambertville, N.J. can be incorporated into flexible, motion sensitive (vibration, compression or flexure), active fiber composite shapes that can be placed in shoes, boots, and clothing or any location where there is a source of waste energy or mechanical force. These flexible composites generate power from the scavenged energy and harness it using microprocessor controls developed specifically for this purpose. Advanced Cerametric's viscose suspension spinning process (VSSP) can produce fibers ranging in diameter from 10 μm (⅕₀ of a human hair) to 250 μm and mechanical to electrical transduction efficiency can reach 70 percent compared with the 16-18 percent common to solar energy conversion. The composite fibers can be molded into user-defined shapes and is flexible and motion-sensitive. In one implementation, energy is harvested by the body motion such as the foot action or vibration of the PZT composites. The energy is converted and stored in a low-leakage charge circuit until a predetermined threshold voltage is reached. Once the threshold is reached, the regulated power is allowed to flow for a sufficient period to power the wireless node such as the Zigbee CPU/transceiver. The transmission is detected by nearby wireless nodes that are AC-powered and forwarded to the base station for signal processing. Power comes from the vibration of the system being monitored and the unit requires no maintenance, thus reducing life-cycle costs. In one embodiment, the housing of the unit can be PZT composite, thus reducing the weight.

In another embodiment, body energy generation systems include electro active polymers (EAPs) and dielectric elastomers. EAPs are a class of active materials that have a mechanical response to electrical stimulation and produce an electric potential in response to mechanical stimulation. EAPs are divided into two categories, electronic, driven by electric field, and ionic, driven by diffusion of ions. In one embodiment, ionic polymers are used as biological actuators that assist muscles for organs such as the heart and eyes. Since the ionic polymers require a solvent, the hydrated human body provides a natural environment. Polymers are actuated to contract, assisting the heart to pump, or correcting the shape of the eye to improve vision. Another use is as miniature surgical tools that can be inserted inside the body. EAPs can also be used as artificial smooth muscles, one of the original ideas for EAPs. These muscles could be placed in exoskeletal suits for soldiers or prosthetic devices for disabled persons. Along with the energy generation device, ionic polymers can be the energy storage vessel for harvesting energy. The capacitive characteristics of the EAP allow the polymers to be used in place of a standard capacitor bank. With EAP based jacket, when a person moves his/her arms, it will put the electro active material around the elbow in tension to generate power. Dielectric elastomers can support 50-100% area strain and generate power when compressed. Although the material could again be used in a bending arm type application, a shoe type electric generator can be deployed by placing the dielectric elastomers in the sole of a shoe. The constant compressive force provided by the feet while walking would ensure adequate power generation.

For wireless nodes that require more power, electromagnetics, including coils, magnets, and a resonant beam, and micro-generators can be used to produce electricity from readily available foot movement. Typically, a transmitter needs about 30 mW, but the device transmits for only tens of milliseconds, and a capacitor in the circuit can be charged using harvested energy and the capacitor energy drives the wireless transmission, which is the heaviest power requirement. Electromagnetic energy harvesting uses a magnetic field to convert mechanical energy to electrical. A coil attached to the oscillating mass traverses through a magnetic field that is established by a stationary magnet. The coil travels through a varying amount of magnetic flux, inducing a voltage according to Faraday's law. The induced voltage is inherently small and must therefore be increased to viably source energy. Methods to increase the induced voltage include using a transformer, increasing the number of turns of the coil, and/or increasing the permanent magnetic field. Electromagnetic devices use the motion of a magnet relative to a wire coil to generate an electric voltage. A permanent magnet is placed inside a wound coil. As the magnet is moved through the coil it causes a changing magnetic flux. This flux is responsible for generating the voltage which collects on the coil terminals. This voltage can then be supplied to an electrical load. Because an electromagnetic device needs a magnet to be sliding through the coil to produce voltage, energy harvesting through vibrations is an ideal application. In one embodiment, electromagnetic devices are placed inside the heel of a shoe. One implementation uses a sliding magnet-coil design, the other, opposing magnets with one fixed and one free to move inside the coil. If the length of the coil is increased, which increases the turns, the device is able to produce more power.

In an electrostatic (capacitive) embodiment, energy harvesting relies on the changing capacitance of vibration-dependant varactors. A varactor, or variable capacitor, is initially charged and, as its plates separate because of vibrations, mechanical energy is transformed into electrical energy. MEMS variable capacitors are fabricated through relatively mature silicon micro-machining techniques.

In another embodiment, the wireless node can be powered from thermal and/or kinetic energy. Temperature differentials between opposite segments of a conducting material result in heat flow and consequently charge flow, since mobile, high-energy carriers diffuse from high to low concentration regions. Thermopiles consisting of n- and p-type materials electrically joined at the high-temperature junction are therefore constructed, allowing heat flow to carry the dominant charge carriers of each material to the low temperature end, establishing in the process a voltage difference across the base electrodes. The generated voltage and power is proportional to the temperature differential and the Seebeck coefficient of the thermoelectric materials. Body heat from a user's wrist is captured by a thermoelectric element whose output is boosted and used to charge the a lithium ion rechargeable battery. The unit utilizes the Seeback Effect which describes the voltage created when a temperature difference exists across two different metals. The thermoelectric generator takes body heat and dissipates it to the ambient air, creating electricity in the process.

In another embodiment, the kinetic energy of a person's movement is converted into energy. As a person moves their weight, a small weight inside the wireless node moves like a pendulum and turns a magnet to produce electricity which can be stored in a super-capacitor or a rechargeable lithium battery. Similarly, in a vibration energy embodiment, energy extraction from vibrations is based on the movement of a "spring-mounted" mass relative to its support frame. Mechanical acceleration is produced by vibrations that in turn cause the mass component to move and oscillate (kinetic energy). This relative displacement causes opposing frictional and damping forces to be exerted against the mass, thereby reducing and eventually extinguishing the oscillations. The damping forces literally absorb the kinetic energy of the initial vibration. This energy can be converted into electrical energy via an electric field (electrostatic), magnetic field (electromagnetic), or strain on a piezoelectric material.

Another embodiment extracts energy from the surrounding environment using a small rectenna (microwave-power receivers or ultrasound power receivers) placed in patches or membranes on the skin or alternatively injected underneath the skin. The rectenna converts the received emitted power back to usable low frequency/dc power. A basic rectenna consists of an antenna, a low pass filter, an ac/dc converter and a dc bypass filter. The rectenna can capture renewable electromagnetic energy available in the radio frequency (RF) bands such as AM radio, FM radio, TV, very high frequency (VHF), ultra high frequency (UHF), global system for mobile communications (GSM), digital cellular systems (DCS) and especially the personal communication system (PCS) bands, and unlicensed ISM bands such as 2.4 GHz and 5.8 GHz bands, among others. The system captures the ubiquitous electromagnetic energy (ambient RF noise and signals) opportunistically present in the environment and transforming that energy into useful electrical power. The energy-harvesting antenna is preferably designed to be a wideband, omnidirectional antenna or antenna array that has maximum efficiency at selected bands of frequencies containing the highest energy levels. In a system with an array of antennas, each antenna in the array can be designed to have maximum efficiency at the same or different bands of frequency from one another. The collected RF energy is then converted into usable DC power using a diode-type or other suitable rectifier. This power may be used to drive, for example, an amplifier/filter module connected to a second antenna system that is optimized for a particular frequency and application. One antenna system can act as an energy harvester while the other antenna acts as a signal transmitter/receiver. The antenna circuit elements are formed using standard wafer manufacturing techniques. The antenna output is stepped up and rectified before presented to a trickle charger. The charger can recharge a complete battery by providing a larger potential difference between terminals and more power for charging during a period of time. If battery includes individual micro-battery cells, the trickle charger provides smaller amounts of power to each individual battery cell, with the charging proceeding on a cell by cell basis. Charging of the battery cells continues whenever ambient power is available. As the load depletes cells, depleted cells are switched out with charged cells. The rotation of depleted cells and charged cells continues as required. Energy is banked and managed on a micro-cell basis.

In a solar cell embodiment, photovoltaic cells convert incident light into electrical energy. Each cell consists of a reverse biased pn+ junction, where light interfaces with the heavily doped and narrow n+ region. Photons are absorbed within the depletion region, generating electron-hole pairs. The built-in electric field of the junction immediately separates each pair, accumulating electrons and holes in the n+ and p-regions, respectively, and establishing in the process an open circuit voltage. With a load connected, accumulated electrons travel through the load and recombine with holes at the p-side, generating a photocurrent that is directly proportional to light intensity and independent of cell voltage.

As the energy-harvesting sources supply energy in irregular, random "bursts," an intermittent charger waits until sufficient energy is accumulated in a specially designed transitional storage such as a capacitor before attempting to transfer it to the storage device, lithium-ion battery, in this case. Moreover, the system must partition its functions into time slices (time-division multiplex), ensuring enough energy is harvested and stored in the battery before engaging in power-sensitive tasks. Energy can be stored using a secondary (rechargeable) battery and/or a supercapacitor. The different characteristics of batteries and supercapacitors make them suitable for different functions of energy storage. Supercapacitors provide the most volumetrically efficient approach to meeting high power pulsed loads. If the energy must be stored for a long time, and released slowly, for example as back up, a battery would be the preferred energy storage device. If the energy must be delivered quickly, as in a pulse for RF communications, but long term storage is not critical, a supercapacitor would be sufficient. The system can employ i) a battery (or several batteries), ii) a supercapacitor (or supercapacitors), or iii) a combination of batteries and supercapacitors appropriate for the application of interest. In one embodiment, a microbattery and a microsupercapacitor can be used to store energy. Like batteries, supercapacitors are electrochemical devices; however, rather than generating a voltage from a chemical reaction, supercapacitors store energy by separating charged species in an electrolyte. In one embodiment, a flexible, thin-film, rechargeable battery from Cymbet Corp. of Elk River, Minn. provides 3.6V and can be recharged by a reader. The battery cells can be from 5 to 25 microns thick. The batteries can be recharged with solar energy, or can be recharged by inductive coupling. The tag is put within range of a coil attached to an energy source. The coil "couples" with the antenna on the RFID tag, enabling the tag to draw energy from the magnetic field created by the two coils.

FIG. 6B shows an exemplary mesh network working with the wearable appliance of FIG. 6A. Data collected and communicated on the display 1382 of the watch as well as voice is transmitted to a base station 1390 for communicating over a network to an authorized party 1394. The watch and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX or 802.16 standard base station that can communicate VOIP and data over a wide area network. In one implementation, Zigbee or 802.15 appliances communicate locally and then transmits to the wide area network (WAN) such as the Internet over WiFi or WiMAX. Alternatively, the base station can communicate with the WAN over POTS and a wireless network such as cellular or WiMAX or both.

Figure 7:
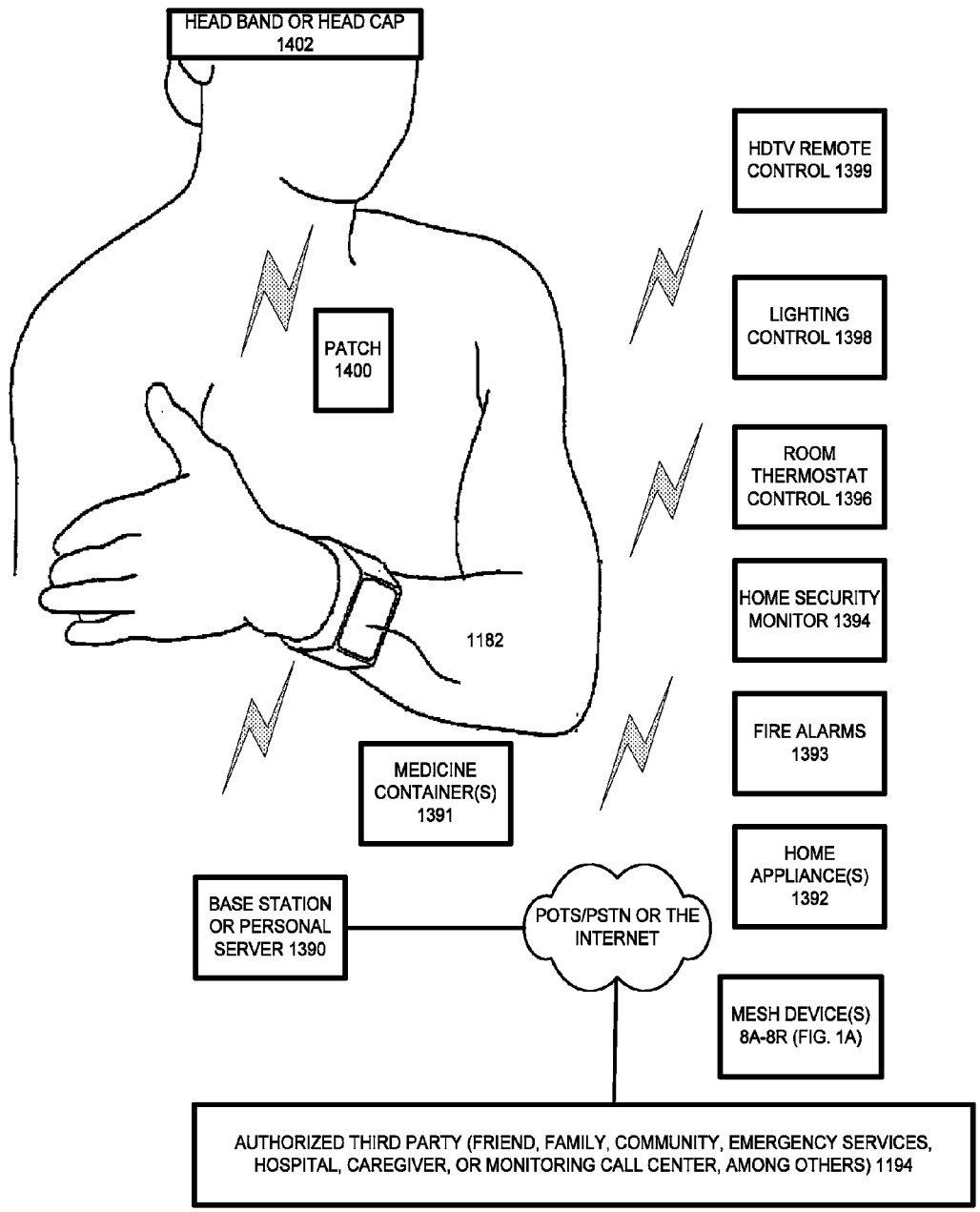
FIG. 7 shows an exemplary mesh network working with the wearable appliance of FIG. 6A.

One embodiment of FIG. 7 includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist watch or wrist band are used to apply AC or DC constant current into the body or body segment. The voltage signal from the surface of the body is measured in terms of impedance using the same or an additional two electrodes on the watch or wrist band. In a bipolar implementation, one electrode on the wrist watch or wrist band is used to apply AC or DC constant current into the body or body segment. The voltage signal from the surface of the body is measured in terms of impedance using the same or an alternative electrode on the watch or wrist band. The system of FIG. 6B may include a BI patch 1400 that wirelessly communicates BI information with the wrist watch. Other patches 1400 can be used to collect other medical information or vital parameter and communicate with the wrist watch or base station or the information could be relayed through each wireless node or appliance to reach a destination appliance such as the base station, for example. The system of FIG. 6B can also include a head-cap 1402 that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes (I1, I2) is used as current electrodes to introduce a low intensity constant current at high frequency into the body. A pair of electrodes (E1, E2) measures changes accompanying physiological events. Voltage measured across E1-E2 is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodess in these embodiments can be the same, adjacent to one another, or at significantly different locations. The electrode(s) can apply current levels from 20 uA to 10 mA rms at a frequency range of 20-100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower-body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyperhydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor includes detecting and/or monitoring hypovolemia, hemorrhage or blood loss. The impedance measurements can be made sequentially over a period of in time; and the system can determine whether the subject is externally or internally bleeding based on a change in measured impedance. The watch can also report temperature, heat flux, vasodilation and blood pressure along with the BI information.

In one embodiment, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity ρ of blood and the length L of the chest, the impedance change ΔZ and base impedance (Zo) to the volume change ΔV of the tissue under measurement can be derived as follows:

$$\Delta V = \rho \frac{L^2}{Z_0^2} \Delta Z$$

In one embodiment, SV is determined as a function of the first derivative of the impedance waveform (dZ/dtmax) and the left ventricular ejection time (LVET)

$$SV = \rho \frac{L^2}{Z_0^2} \left(\frac{dZ}{dt}\right)_{max} LVET$$

In one embodiment, L is approximated to be 17% of the patient's height (H) to yield the following:

$$SV = \left(\frac{(0.17H)^3}{4.2}\right) \frac{\left(\frac{dZ}{dt}\right)_{max}}{Z_0} LVET$$

In another embodiment, δ or the actual weight divided by the ideal weight is used:

$$SV = \delta \times \left(\frac{(0.17H)^3}{4.2}\right) \frac{\left(\frac{dZ}{dt}\right)_{max}}{Z_0} LVET$$

The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

Once SV has been determined, CO can be determined according to the following expression:

CO=SV*HR, where HR=heart rate

CO can be determined for every heart-beat. Thus, the system can determine SV and CO on a beat-to-beat basis.

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetrapolar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurements procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 911 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Po2 (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near 40% of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

Additional sensors such as thermocouples or thermistors and/or heat flux sensors can also be provided to provide measured values useful in analysis. In general, skin surface temperature will change with changes in blood flow in the vicinity of the skin surface of an organism. Such changes in blood flow can occur for a number of reasons, including thermal regulation, conservation of blood volume, and hormonal changes. In one implementation, skin surface measurements of temperature or heat flux are made in conjunction with hydration monitoring so that such changes in blood flow can be detected and appropriately treated.

In one embodiment, the patch includes a sound transducer such as a microphone or a piezoelectric transducer to pick up sound produced by bones or joints during movement. If bone surfaces are rough and poorly lubricated, as in an arthritic knee, they will move unevenly against each other, producing a high-frequency, scratching sound. The high-frequency sound from joints is picked up by wide-band acoustic sensor(s) or microphone(s) on a patient's body such as the knee. As the patient flexes and extends their knee, the sensors measure the sound frequency emitted by the knee and correlate the sound to monitor osteoarthritis, for example.

In another embodiment, the patch includes a Galvanic Skin Response (GSR) sensor. In this sensor, a small current is passed through one of the electrodes into the user's body such as the fingers and the CPU calculates how long it takes for a capacitor to fill up. The length of time the capacitor takes to fill up allows us to calculate the skin resistance: a short time means low resistance while a long time means high resistance. The GSR reflects sweat gland activity and changes in the sympathetic nervous system and measurement variables. Measured from the palm or fingertips, there are changes in the relative conductance of a small electrical current between the electrodes. The activity of the sweat glands in response to sympathetic nervous stimulation (Increased sympathetic activation) results in an increase in the level of conductance. Fear, anger, startle response, orienting response and sexual feelings are all among the emotions which may produce similar GSR responses.

In yet another embodiment, measurement of lung function such as peak expiratory flow readings is done though a sensor such as Wright's peak flow meter. In another embodiment, a respiratory estimator is provided that avoids the inconvenience of having the patient breathing through the flow sensor. In the respiratory estimator embodiment, heart period data from EKG/ECG is used to extract respiratory detection features. The heart period data is transformed into time-frequency distribution by applying a time-frequency transformation such as short-term Fourier transformation (STFT). Other possible methods are, for example, complex demodulation and wavelet transformation. Next, one or more respiratory detection features may be determined by setting up amplitude modulation of time-frequency plane, among others. The respiratory recognizer first generates a math model that correlates the respiratory detection features with the actual flow readings. The math model can be adaptive based on pre-determined data and on the combination of different features to provide a single estimate of the respiration. The estimator can be based on different mathematical functions, such as a curve fitting approach with linear or polynomical equations, and other types of neural network implementations, non-linear models, fuzzy systems, time series models, and other types of multivariate models capable of transferring and combining the information from several inputs into one estimate. Once the math model has been generated, the respirator estimator provides a real-time flow estimate by receiving EKG/ECG information and applying the information to the math model to compute the respiratory rate. Next, the computation of ventilation uses information on the tidal volume. An estimate of the tidal volume may be derived by utilizing different forms of information on the basis of the heart period signal. For example, the functional organization of the respiratory system has an impact in both respiratory period and tidal volume. Therefore, given the known relationships between the respiratory period and tidal volume during and transitions to different states, the information inherent in the heart period derived respiratory frequency may be used in providing values of tidal volume. In specific, the tidal volume contains inherent dynamics which may be, after modeling, applied to capture more closely the behavioral dynamics of the tidal volume. Moreover, it appears that the heart period signal, itself, is closely associated with tidal volume and may be therefore used to increase the reliability of deriving information on tidal volume. The accuracy of the tidal volume estimation may be further enhanced by using information on the subjects vital capacity (i.e., the maximal quantity of air that can be contained in the lungs during one breath). The information on vital capacity, as based on physiological measurement or on estimates derived from body measures such as height and weight, may be helpful in estimating tidal volume, since it is likely to reduce the effects of individual differences on the estimated tidal volume. Using information on the vital capacity, the mathematical model may first give values on the percentage of lung capacity in use, which may be then transformed to liters per breath. The optimizing of tidal volume estimation can based on, for example, least squares or other type of fit between the features and actual tidal volume. The minute ventilation may be derived by multiplying respiratory rate (breaths/min) with tidal volume (liters/breath).

In another embodiment, inductive plethysmography can be used to measure a cross-sectional area of the body by determining the self-inductance of a flexible conductor closely encircling the area to be measured. Since the inductance of a substantially planar conductive loop is well known to vary as, inter alia, the cross-sectional area of the loop, a inductance measurement may be converted into a plethysmographic area determination. Varying loop inductance may be measured by techniques known in the art, such as, e.g., by connecting the loop as the inductance in a variable frequency LC oscillator, the frequency of the oscillator then varying with the cross-sectional area of the loop inductance varies. Oscillator frequency is converted into a digital value, which is then further processed to yield the physiological parameters of interest. Specifically, a flexible conductor measuring a cross-sectional area of the body is closely looped around the area of the body so that the inductance, and the changes in inductance, being measured results from magnetic flux through the cross-sectional area being measured. The inductance thus depends directly on the cross-sectional area being measured, and not indirectly on an area which changes as a result of the factors changing the measured cross-sectional area. Various physiological parameters of medical and research interest may be extracted from repetitive measurements of the areas of various cross-sections of the body. For example, pulmonary function parameters, such as respiration volumes and rates and apneas and their types, may be determined from measurements of, at least, a chest transverse cross-sectional area and also an abdominal transverse cross-sectional area. Cardiac parameters, such central venous pressure, left and right ventricular volumes waveforms, and aortic and carotid artery pressure waveforms, may be extracted from repetitive measurements of transverse cross-sectional areas of the neck and of the chest passing through the heart. Timing measurements can be obtained from concurrent ECG measurements, and less preferably from the carotid pulse signal present in the neck. From the cardiac-related signals, indications of ischemia may be obtained independently of any ECG changes. Ventricular wall ischemia is known to result in paradoxical wall motion during ventricular contraction (the ischemic segment paradoxically "balloons" outward instead of normally contracting inward). Such paradoxical wall motion, and thus indications of cardiac ischemia, may be extracted from chest transverse cross-section area measurements. Left or right ventricular ischemia may be distinguished where paradoxical motion is seen predominantly in left or right ventricular waveforms, respectively. For another example, observations of the onset of contraction in the left and right ventricles separately may be of use in providing feedback to bi-ventricular cardiac pacing devices. For a further example, pulse oximetry determines hemoglobin saturation by measuring the changing infrared optical properties of a finger. This signal may be disambiguated and combined with pulmonary data to yield improved information concerning lung function.

In one embodiment to monitor and predict stroke attack, a cranial bioimpedance sensor is applied to detect fluids in the brain. The brain tissue can be modeled as an electrical circuit where cells with the lipid bilayer act as capacitors and the intra and extra cellular fluids act as resistors. The opposition to the flow of the electrical current through the cellular fluids is resistance. The system takes 50-kHz single-frequency bio-impedance measurements reflecting the electrical conductivity of brain tissue. The opposition to the flow of the current by the capacitance of lipid bilayer is reactance. In this embodiment, microamps of current at 50 kHz are applied to the electrode system. In one implementation, the electrode system consists of a pair of coaxial electrodes each of which has a current electrode and a voltage sensing electrode. For the measurement of cerebral bioimpedance, one pair of gel current electrodes is placed on closed eyelids and the second pair of voltage electrodes is placed in the suboccipital region projecting towards the foramen magnum. The electrical current passes through the orbital fissures and brain tissue. The drop in voltage is detected by the suboccipital electrodes and then calculated by the processor to bioimpedance values. The bioimpedance value is used to detect brain edema, which is defined as an increase in the water content of cerebral tissue which then leads to an increase in overall brain mass. Two types of brain edema are vasogenic or cytotoxic. Vasogenic edema is a result of increased capillary permeability. Cytotoxic edema reflects the increase of brain water due to an osmotic imbalance between plasma and the brain extracellular fluid. Cerebral edema in brain swelling contributes to the increase in intracranial pressure and an early detection leads to timely stroke intervention.

In another example, a cranial bioimpedance tomography system contructs brain impedance maps from surface measurements using nonlinear optimization. A nonlinear optimization technique utilizing known and stored constraint values permits reconstruction of a wide range of conductivity values in the tissue. In the nonlinear system, a Jacobian Matrix is renewed for a plurality of iterations. The Jacobian Matrix describes changes in surface voltage that result from changes in conductivity. The Jacobian Matrix stores information relating to the pattern and position of measuring electrodes, and the geometry and conductivity distributions of measurements resulting in a normal case and in an abnormal case. The nonlinear estimation determines the maximum voltage difference in the normal and abnormal cases.

In one embodiment, an electrode array sensor can include impedance, bio-potential, or electromagnetic field tomography imaging of cranial tissue. The electrode array sensor can be a geometric array of discrete electrodes having an equally-spaced geometry of multiple nodes that are capable of functioning as sense and reference electrodes. In a typical tomography application the electrodes are equally-spaced in a circular configuration. Alternatively, the electrodes can have non-equal spacing and/or can be in rectangular or other configurations in one circuit or multiple circuits. Electrodes can be configured in concentric layers too. Points of extension form multiple nodes that are capable of functioning as an electrical reference. Data from the multiple reference points can be collected to generate a spectrographic composite for monitoring over time.

The patient's brain cell generates an electromagnetic field of positive or negative polarity, typically in the millivolt range. The sensor measures the electromagnetic field by detecting the difference in potential between one or more test electrodes and a reference electrode. The bio-potential sensor uses signal conditioners or processors to condition the potential signal. In one example, the test electrode and reference electrode are coupled to a signal conditioner/processor that includes a lowpass filter to remove undesired high frequency signal components. The electromagnetic field signal is typically a slowly varying DC voltage signal. The lowpass filter removes undesired alternating current components arising from static discharge, electromagnetic interference, and other sources.

In one embodiment, the impedance sensor has an electrode structure with annular concentric circles including a central electrode, an intermediate electrode and an outer electrode, all of which are connected to the skin. One electrode is a common electrode and supplies a low frequency signal between this common electrode and another of the three electrodes. An amplifier converts the resulting current into a voltage between the common electrode and another of the three electrodes. A switch switches between a first circuit using the intermediate electrode as the common electrode and a second circuit that uses the outer electrode as a common electrode. The sensor selects depth by controlling the extension of the electric field in the vicinity of the measuring electrodes using the control electrode between the measuring electrodes. The control electrode is actively driven with the same frequency as the measuring electrodes to a signal level taken from one of the measuring electrodes but multiplied by a complex number with real and imaginary parts controlled to attain a desired depth penetration. The controlling field functions in the manner of a field effect transistor in which ionic and polarization effects act upon tissue in the manner of a semiconductor material.

With multiple groups of electrodes and a capability to measure at a plurality of depths, the system can perform tomographic imaging or measurement, and/or object recognition. In one embodiment, a fast reconstruction technique is used to reduce computation load by utilizing prior information of normal and abnormal tissue conductivity characteristics to estimate tissue condition without requiring full computation of a non-linear inverse solution.

In another embodiment, the bioimpedance system can be used with electro-encephalograph (EEG) or ERP. Since this embodiment collects signals related to blood flow in the brain, collection can be concentrated in those regions of the brain surface corresponding to blood vessels of interest. A headcap with additional electrodes placed in proximity to regions of the brain surface fed by a blood vessel of interest, such as the medial cerebral artery enables targeted information from the regions of interest to be collected. The headcap can cover the region of the brain surface that is fed by the medial cerebral artery. Other embodiments of the headcap can concentrate electrodes on other regions of the brain surface, such as the region associated with the somatosensory motor cortex. In alternative embodiments, the headcap can cover the skull more completely. Further, such a headcap can include electrodes thoughout the cap while concentrating electrodes in a region of interest. Depending upon the particular application, arrays of 1-16 head electrodes may be used, as compared to the International 10/20 system of 19-21 head electrodes generally used in an EEG instrument.

In one implementation, each amplifier for each EEG channel is a high quality analog amplifier device. Full bandwidth and ultra-low noise amplification are obtained for each electrode. Low pass, high pass, hum notch filters, gain, un-block, calibration and electrode impedance check facilities are included in each amplifier. All 8 channels in one EEG amplifier unit have the same filter, gain, etc. settings. Noise figures of less than 0.1 uV r.m.s. are achieved at the input and optical coupling stages. These figures, coupled with good isolation/common mode rejection result in signal clarity. Nine high pass filter ranges include 0.01 Hz for readiness potential measurement, and 30 Hz for EMG measurement.

In one embodiment, stimulations to elicit EEG signals are used in two different modes, i.e., auditory clicks and electric pulses to the skin. The stimuli, although concurrent, are at different prime number frequencies to permit separation of different evoked potentials (EPs) and avoid interference. Such concurrent stimulations for EP permit a more rapid, and less costly, examination and provide the patient's responses more quickly. Power spectra of spontaneous EEG, waveshapes of Averaged Evoked Potentials, and extracted measures, such as frequency specific power ratios, can be transmitted to a remote receiver. The latencies of successive EP peaks of the patient may be compared to those of a normal group by use of a normative template. To test for ischemic stroke or intracerebral or subarachnoid hemorrhage, the system provides a blood oxygen saturation monitor, using an infra-red or laser source, to alert the user if the patient's blood in the brain or some brain region is deoxygenated.

A stimulus device may optionally be placed on each subject, such as an audio generator in the form of an ear plug, which produces a series of "click" sounds. The subject's brain waves are detected and converted into audio tones. The device may have an array of LED (Light Emitting Diodes) which blink depending on the power and frequency composition of the brain wave signal. Power ratios in the frequencies of audio or somatosensory stimuli are similarly encoded. The EEG can be transmitted to a remote physician or medical aide who is properly trained to determine whether the patient's brain function is abnormal and may evaluate the functional state of various levels of the patient's nervous system.

In another embodiment, three pairs of electrodes are attached to the head of the subject under examination via tape or by wearing a cap with electrodes embedded. In one embodiment, the electrode pairs are as follows:
 1) top of head to anterior throat
 2) inion-nasion
 3) left to right mastoid (behind ear).

A ground electrode is located at an inactive site of the upper part of the vertebral column. The electrodes are connected to differential amplification devices as disclosed below. Because the electrical charges of the brain are so small (on the order of microvolts), amplification is needed. The three amplified analog signals are converted to digital signals and averaged over a certain number of successive digital values to eliminate erroneous values originated by noise on the analog signal.

All steps defined above are linked to a timing signal which is also responsible for generating stimuli to the subject. The responses are processed in a timed relation to the stimuli and averaged as the brain responds to these stimuli. Of special interest are the responses within certain time periods and time instances after the occurrence of a stimulus of interest. These time periods and instances and their references can be:
 25 to 60 milliseconds: P1-N1
 180 to 250 milliseconds: N2
 100 milliseconds: N100
 200 milliseconds: P2
 300 milliseconds: P300.

In an examination two stimuli sets may be used in a manner that the brain has to respond to the two stimuli differently, one stimulus has a high probability of occurrence, and the other stimulus is a rare occurring phenomena. The rare response is the response of importance. Three response signals are sensed and joined into a three dimensional cartesian system by a mapping program. The assignments can be
 nasion-inion=X,
 left-right mastoid=Y, and
 top of head to anterior throat=Z.

The assignment of the probes to the axes and the simultaneous sampling of the three response signals at the same rate and time relative to the stimuli allows to real-time map the electrical signal in a three dimensional space. The signal can be displayed in a perspective representation of the three dimensional space, or the three components of the vector are displayed by projecting the vector onto the three planes X-Y, Y-Z, and X-Z, and the three planes are inspected together or separately. Spatial information is preserved for reconstruction as a map. The Vector Amplitude (VA) measure provides information about how far from the center of the head the observed event is occurring; the center of the head being the center (0,0,0) of the coordinate system.

The cranial bioimpedance sensor can be applied singly or in combination with a cranial blood flow sensor, which can be optical, ultrasound, electromagnetic sensor(s) as described in more details below. In an ultrasound imaging implementation, the carotid artery is checked for plaque build-up. Atherosclerosis is systemic—meaning that if the carotid artery has plaque buildup, other important arteries, such as coronary and leg arteries, might also be atherosclerotic.

In another embodiment, an epicardial array monopolar ECG system converts signals into the multichannel spectrum domain and identifies decision variables from the autospectra. The system detects and localizes the epicardial projections of ischemic myocardial ECGs during the cardiac activation phase. This is done by transforming ECG signals from an epicardial or torso sensor array into the multichannel spectral domain and identifying any one or more of a plurality of decision variables. The ECG array data can be used to detect, localize and quantify reversible myocardial ischemia.

In yet another embodiment, a trans-cranial Doppler velocimetry sensor provides a non-invasive technique for measuring blood flow in the brain. An ultrasound beam from a transducer is directed through one of three natural acoustical windows in the skull to produce a waveform of blood flow in the arteries using Doppler sonography. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

To detect stroke attack, the system can detect numbness or weakness of the face, arm or leg, especially on one side of the body. The system detects sudden confusion, trouble speaking or understanding, sudden trouble seeing in one or both eyes, sudden trouble walking, dizziness, loss of balance or coordination, or sudden, severe headache with no known cause. In one embodiment to detect heart attack, the system detects discomfort in the center of the chest that lasts more than a few minutes, or that goes away and comes back. Symptoms can include pain or discomfort in one or both arms, the back, neck, jaw or stomach. The system can also monitor for shortness of breath which may occur with or without chest discomfort. Other signs may include breaking out in a cold sweat, nausea or lightheadedness. In order to best analyze a patient's risk of stroke, additional patient data is utilized by a stroke risk analyzer. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the antinuclear antibody panel, B-vitamin deficiency, C-reactive protein value, calcium level, cholesterol levels, entidal CO2, fibromogin, amount of folic acid, glucose level, hematocrit percentage, H-pylori antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, family history of stroke, surgery history, for example. The automated analyzer can also consider related pathologies in analyzing a patient's risk of stroke, including but not limited to gastritis, increased intracranial pressure, sleep disorders, small vessel disease, and vasculitis.

In one embodiment, the processor and transceiver on the watch, the patch(es) and the base station conform to the Zigbee protocol. ZigBee is a cost-effective, standards-based wireless networking solution that supports low data-rates, low-power consumption, security, and reliability. Single chip Zigbee controllers with wireless transceivers built-in include the Chipcon/Ember CC2420: Single-chip 802.15.4 radio transceiver and the FreeScale single chip Zigbee and microcontroller. In various embodiments, the processor communicates with a Z axis accelerometer measures the patient's up and down motion and/or an X and Y axis accelerometer measures the patient's forward and side movements. In one embodiment, EKG and/or blood pressure parameters can be captured by the processor. The controllers upload the captured data when the memory is full or while in wireless contact with other Zigbee nodes.

The wristwatch device can also be used to control home automation. The user can have flexible management of lighting, heating and cooling systems from anywhere in the home. The watch automates control of multiple home systems to improve conservation, convenience and safety. The watch can capture highly detailed electric, water and gas utility usage data and embed intelligence to optimize consumption of natural resources. The system is convenient in that it can be installed, upgraded and networked without wires. The patient can receive automatic notification upon detection of unusual events in his or her home. For example, if smoke or carbon monoxide detectors detect a problem, the wrist-watch can buzz or vibrate to alert the user and the central hub triggers selected lights to illuminate the safest exit route.

In another embodiment, the watch serves a key fob allowing the user to wirelessly unlock doors controlled by Zigbee wireless receiver. In this embodiment, when the user is within range, the door Zigbee transceiver receives a request to unlock the door, and the Zigbee transceiver on the door transmits an authentication request using suitable security mechanism. Upon entry, the Zigbee doorlock device sends access signals to the lighting, air-conditioning and entertainment systems, among others. The lights and temperature are automatically set to pre-programmed preferences when the user's presence is detected.

Although Zigbee is mentioned as an exemplary protocol, other protocols such as UWB, Bluetooth, WiFi and WiMAX can be used as well.

The sensor can be active and powered by body motion or body heat. The sensor can detect low battery situation and warn the user to provide a replacement battery. In one embodiment, a plurality of sensors attached to the person collects the vital parameters. For example, the sensors can be attached to the infant's clothing (shirt or pant), diaper, undergarment or bed sheet, bed linen, or bed spread. The patient may wear one or more sensors, for example devices for sensing EMG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The heartbeat detector can be one of: EKG detector, ECG detector, optical detector, ultrasonic detector, or microphone/digital stethoscope for picking up heart sound. In one embodiment, one EKG/ECG contact point is provided on the back of the wrist watch case and one or more EKG/ECG contact points are provided on the surface of the watch so that when a user's finger or skin touches the contact points, an electrical signal indicative of heartbeat activity is generated. An electrocardiogram (ECG) or EKG is a graphic tracing of the voltage generated by the cardiac or heart muscle during a heartbeat. It provides very accurate evaluation of the performance of the heart. The heart generates an electrochemical impulse that spreads out in the heart in such a fashion as to cause the cells to contract and relax in a timely order and thus give the heart a pumping characteristic. This sequence is initiated by a group of nerve cells called the sinoatrial (SA) node resulting in a polarization and depolarization of the cells of the heart. Because this action is electrical in nature and because the body is conductive with its fluid content, this electrochemical action can be measured at the surface of the body. An actual voltage potential of approximately 1 mV develops between various body points. This can be measured by placing electrode contacts on the body. The four extremities and the chest wall have become standard sites for applying the electrodes. Standardizing electrocardiograms makes it possible to compare them as taken from person to person and from time to time from the same person. The normal electrocardiogram shows typical upward and downward deflections that reflect the alternate contraction of the atria (the two upper chambers) and of the ventricles (the two lower chambers) of the heart. The voltages produced represent pressures exerted by the heart muscles in one pumping cycle. The first upward deflection, P, is due to atria contraction and is known as the atrial complex. The other deflections, Q, R, S, and T, are all due to the action of the ventricles and are known as the ventricular complexes. Any deviation from the norm in a particular electrocardiogram is indicative of a possible heart disorder.

The CPU measures the time duration between the sequential pulses and converts each such measurement into a corresponding timing measurement indicative of heart rate. The CPU also processes a predetermined number of most recently occurring timing measurements in a prescribed fashion, to produce an estimate of heartbeat rate for display on a display device on the watch and/or for transmission over the wireless network. This estimate is updated with the occurrence of each successive pulse.

In one embodiment, the CPU produces the estimate of heartbeat rate by first averaging a plurality of measurements, then adjusting the particular one of the measurements that differs most from the average to be equal to that average, and finally computing an adjusted average based on the adjusted set of measurements. The process may repeat the foregoing operations a number of times so that the estimate of heartbeat rate is substantially unaffected by the occurrence of heartbeat artifacts.

In one EKG or ECG detector, the heartbeat detection circuitry includes a differential amplifier for amplifying the signal transmitted from the EKG/ECG electrodes and for converting it into single-ended form, and a bandpass filter and a 60 Hz notch filter for removing background noise. The CPU measures the time durations between the successive pulses and estimates the heartbeat rate. The time durations between the successive pulses of the pulse sequence signal provides an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the stored measurements are averaged, to produce an average rate measurement. The CPU optionally determines which of the stored measurements differs most from the average, and replaces that measurement with the average.

Upon initiation, the CPU increments a period timer used in measuring the time duration between successive pulses. This timer is incremented in steps of about two milliseconds in one embodiment. It is then determined whether or not a pulse has occurred during the previous two milliseconds. If it has not, the CPU returns to the initial step of incrementing the period timer. If a heartbeat has occurred, on the other hand, the CPU converts the time duration measurement currently stored in the period timer to a corresponding heartbeat rate, preferably expressed in bpm. After the heartbeat rate measurement is computed, the CPU determines whether or not the computed rate is intermediate prescribed thresholds of 20 bpm and 240 bpm. If it is not, it is assumed that the detected pulse was not in fact a heartbeat and the period timer is cleared.

In an optical heartbeat detector embodiment, an optical transducer is positioned on a finger, wrist, or ear lobe. The ear, wrist or finger pulse oximeter waveform is then analyzed to extract the beat-to-beat amplitude, area, and width (half height) measurements. The oximeter waveform is used to generate heartbeat rate in this embodiment. In one implementation, a reflective sensor such as the Honeywell HLC1395 can be used. The device emits lights from a window in the infrared spectrum and receives reflected light in a second window. When the heart beats, blood flow increases temporarily and more red blood cells flow through the windows, which increases the light reflected back to the detector. The light can be reflected, refracted, scattered, and absorbed by one or more detectors. Suitable noise reduction is done, and the resulting optical waveform is captured by the CPU.

In another optical embodiment, blood pressure is estimated from the optical reading using a mathematical model such as a linear correlation with a known blood pressure reading. In this embodiment, the pulse oximeter readings are compared to the blood-pressure readings from a known working blood pressure measurement device during calibration. Using these measurements the linear equation is developed relating oximeter output waveform such as width to blood-pressure (systolic, mean and pulse pressure). In one embodiment, a transform (such as a Fourier analysis or a Wavelet transform) of the oximeter output can be used to generate a model to relate the oximeter output waveform to the blood pressure. Other non-linear math model or relationship can be determined to relate the oximeter waveform to the blood pressure.

In one implementation, the pulse oximeter probe and a blood pressure cuff are placed on the corresponding contralateral limb to the oscillometric (Dinamap 8100; Critikon, Inc, Tampa, Fla., USA) cuff site. The pulse oximeter captures data on plethysmographic waveform, heart rate, and oxygen saturation. Simultaneous blood pressure measurements were obtained from the oscillometric device, and the pulse oximeter. Systolic, diastolic, and mean blood pressures are recorded from the oscillometric device. This information is used derive calibration parameters relating the pulse oximeter output to the expected blood pressure. During real time operation, the calibration parameters are applied to the oximeter output to predict blood pressure in a continuous or in a periodic fashion. In yet another embodiment, the device includes an accelerometer or alternative motion-detecting device to determine when the patient's hand is at rest, thereby reducing motion-related artifacts introduced to the measurement during calibration and/or operation. The accelerometer can also function as a falls detection device.

In an ultrasonic embodiment, a piezo film sensor element is placed on the wristwatch band. The sensor can be the SDT1-028K made by Measurement Specialties, Inc. The sensor should have features such as: (a) it is sensitive to low level mechanical movements, (b) it has an electrostatic shield located on both sides of the element (to minimize 50/60 Hz AC line interference), (c) it is responsive to low frequency movements in the 0.7-12 Hz range of interest. A filter/amplifier circuit has a three-pole low pass filter with a lower (−3 dB) cutoff frequency at about 12-13 Hz. The low-pass filter prevents unwanted 50/60 Hz AC line interference from entering the sensor. However, the piezo film element has a wide band frequency response so the filter also attenuates any extraneous sound waves or vibrations that get into the piezo element. The DC gain is about +30 dB.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In one embodiment that can determine blood pressure, two piezo film sensors and filter/amplifier circuits can be configured as a non-invasive velocity type blood pressure monitor. One sensor can be on the wrist and the other can be located on the inner left elbow at the same location where Korotkoff sounds are monitored during traditional blood pressure measurements with a spygmometer. The correlation between pulse delay and blood pressure is well known in the art of non-invasive blood pressure monitors.

In yet another embodiment, an ultrasonic transducer generates and transmits an acoustic wave into the user's body such as the wrist or finger. The transducer subsequently receives pressure waves in the form of echoes resulting from the transmitted acoustic waves. In one embodiment, an ultrasonic driving and receiving circuit generates electrical pulses which, when applied to the transducer produce acoustic energy having a frequency on the order of 8 MHz, a pulse width or duration of approximately 8 microseconds, and a pulse repetition interval (PRI) of approximately 16 microseconds, although other values of frequency, pulse width, and PRI may be used. Hence, the transducer emits an 8 microsecond ultrasonic pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted. The transducer converts the received acoustic signal to an electrical signal, which is then supplied to the receiving section of the ultrasonic driver and receiver circuit 616, which contains two receiver circuits. The output of the first receiver circuit is an analog signal representative of the Doppler frequency of the echo received by the transducer which is digitized and supplied to the CPU. Within the CPU, the digitized Doppler frequency is scaled to compute the blood velocity within the artery based on the Doppler frequency. The time-frequency distribution of the blood velocity is then computed. Finally, the CPU maps in time the peak of the time-frequency distribution to the corresponding pressure waveform to produce the estimated mean arterial pressure (MAP). The output of the ultrasonic receiver circuit is an analog echo signal proportional to absorption of the transmitted frequencies by blood or tissue. This analog signal is digitized and process so that each group of echoes, generated for a different transversal position, is integrated to determine a mean value. The mean echo values are compared to determine the minimum value, which is caused by direct positioning over the artery. In one embodiment, the device includes an accelerometer or alternative motion-detecting device to determine when the patient's hand is at rest, thereby reducing motion-related artifacts introduced to the measurement.

In yet another ultrasonic embodiment, a transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the system includes a pair of piezoelectric crystals at an angle to each other, wherein the angle is determined by the depth of the object being monitored. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the user's wrist and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow. Ultrasonic energy is delivered to one of the two piezoelectric elements in the module by the power amplifier. The other element picks up the reflected ultrasonic signal as Doppler frequencies.

In a digital stethoscope embodiment, a microphone or a piezoelectric transducer is placed near the wrist artery to pick up heart rate information. In one embodiment, the microphone sensor and optionally the EKG sensor are place on the wrist band 1374 of the watch to analyze the acoustic signal or signals emanating from the cardiovascular system and, optionally can combine the sound with an electric signal (EKG) emanating from the cardiovascular system and/or an acoustic signal emanating from the respiratory system. The system can perform automated auscultation of the cardiovascular system, the respiratory system, or both. For example, the system can differentiate pathological from benign heart murmurs, detect cardiovascular diseases or conditions that might otherwise escape attention, recommend that the patient go through for a diagnostic study such as an echocardiography or to a specialist, monitor the course of a disease and the effects of therapy, decide when additional therapy or intervention is necessary, and providing a more objective basis for the decision(s) made. In one embodiment, the analysis includes selecting one or more beats for analysis, wherein each beat comprises an acoustic signal emanating from the cardiovascular system; performing a time-frequency analysis of beats selected for analysis so as to provide information regarding the distribution of energy, the relative distribution of energy, or both, over different frequency ranges at one or more points in the cardiac cycle; and processing the information to reach a clinically relevant conclusion or recommendation. In another implementation, the system selects one or more beats for analysis, wherein each beat comprises an acoustic signal emanating from the cardiovascular system; performs a time-frequency analysis of beats selected for analysis so as to provide information regarding the distribution of energy, the relative distribution of energy, or both, over different frequency ranges at one or more points in the cardiac cycle; and present information derived at least in part from the acoustic signal, wherein the information comprises one or more items selected from the group consisting of: a visual or audio presentation of a prototypical beat, a display of the time-frequency decomposition of one or more beats or prototypical beats, and a playback of the acoustic signal at a reduced rate with preservation of frequency content.

In an electromagnetic embodiment where the wrist band incorporates a flexible magnet to provide a magnetic field and one or more electrodes positioned on the wrist band to measure voltage drops which are proportional to the blood velocity, instantaneously variation of the flow can be detected but not artery flow by itself. To estimate the flow of blood in the artery, the user or an actuator such as motorized cuff temporarily stops the blood flow in the vein by applying external pressure or by any other method. During the period of time in which the vein flow is occluded, the decay of the artery flow is measured. This measurement may be used for zeroing the sensor and may be used in a model for estimating the steady artery flow. The decay in artery flow due to occlusion of veins is measured to arrive at a model the rate of artery decay. The system then estimates an average artery flow before occlusion. The blood flow can then be related to the blood pressure.

In another embodiment, an ionic flow sensor is used with a driving electrode that produces a pulsatile current. The pulsatile current causes a separation of positive and negative charges that flows in the blood of the arteries and veins passing in the wrist area. Using electrophoresis principle, the resistance of the volume surrounded by the source first decreases and then increases. The difference in resistance in the blood acts as a mark that moves according to the flow of blood so that marks are flowing in opposite directions by arteries and veins.

In the above embodiments, accelerometer information is used to detect that the patient is at rest prior to making a blood pressure measurement and estimation. Further, a temperature sensor may be incorporated so that the temperature is known at any minute. The processor correlates the temperature measurement to the blood flow measurement for calibration purposes.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

FIG. 7 shows an exemplary mesh network that includes the wrist-watch of FIG. 6 in communication with a mesh network including a telephone such as a wired telephone as well as a cordless telephone. In one embodiment, the mesh network is an IEEE 802.15.4 (ZigBee) network. IEEE 802.15.4 defines two device types; the reduced function device (RFD) and the full function device (FFD). In ZigBee these are referred to as the ZigBee Physical Device types. In a ZigBee network a node can have three roles: ZigBee Coordinator, ZigBee Router, and ZigBee End Device. These are the ZigBee Logical Device types. The main responsibility of a ZigBee Coordinator is to establish a network and to define its main parameters (e.g. choosing a radio-frequency channel and defining a unique network identifier). One can extend the communication range of a network by using ZigBee Routers. These can act as relays between devices that are too far apart to communicate directly. ZigBee End Devices do not participate in routing. An FFD can talk to RFDs or other FFDs, while an RFD can talk only to an FFD. An RFD is intended for applications that are extremely simple, such as a light switch or a passive infrared sensor; they do not have the need to send large amounts of data and may only associate with a single FFD at a time. Consequently, the RFD can be implemented using minimal resources and memory capacity and have lower cost than an FFD. An FFD can be used to implement all three ZigBee Logical Device types, while an RFD can take the role as an End Device.

One embodiment supports a multicluster-multihop network assembly to enable communication among every node in a distribution of nodes. The algorithm should ensure total connectivity, given a network distribution that will allow total connectivity. One such algorithm of an embodiment is described in U.S. Pat. No. 6,832,251, the content of which is incorporated by referenced. The '251 algorithm runs on each node independently. Consequently, the algorithm does not have global knowledge of network topology, only local knowledge of its immediate neighborhood. This makes it well suited to a wide variety of applications in which the topology may be time-varying, and the number of nodes may be unknown. Initially, all nodes consider themselves remotes on cluster zero. The assembly algorithm floods one packet (called an assembly packet) throughout the network. As the packet is flooded, each node modifies it slightly to indicate what the next node should do. The assembly packet tells a node whether it is a base or a remote, and to what cluster it belongs. If a node has seen an assembly packet before, it will ignore all further assembly packets.

The algorithm starts by selecting (manually or automatically) a start node. For example, this could be the first node to wake up. This start node becomes a base on cluster 1, and floods an assembly packet to all of its neighbors, telling them to be remotes on cluster 1. These remotes in turn tell all their neighbors to be bases on cluster 2. Only nodes that have not seen an assembly packet before will respond to this request, so nodes that already have decided what to be will not change their status. The packet continues on, oscillating back and forth between "become base/become remote", and increasing the cluster number each time. Since the packet is flooded to all neighbors at every step, it will reach every node in the network. Because of the oscillating nature of the "become base/become remote" instructions, no two bases will be adjacent. The basic algorithm establishes a multi-cluster network with all gateways between clusters, but self-assembly time is proportional with the size of the network. Further, it includes only single hop clusters. Many generalizations are possible, however. If many nodes can begin the network nucleation, all that is required to harmonize the clusters is a mechanism that recognizes precedence (e.g., time of nucleation, size of sub-network), so that conflicts in boundary clusters are resolved. Multiple-hop clusters can be enabled by means of establishing new clusters from nodes that are N hops distant from the master.

Having established a network in this fashion, the masters can be optimized either based on number of neighbors, or other criteria such as minimum energy per neighbor communication. Thus, the basic algorithm is at the heart of a number of variations that lead to a scalable multi-cluster network that establishes itself in time, and that is nearly independent of the number of nodes, with clusters arranged according to any of a wide range of optimality criteria. Network synchronism is established at the same time as the network connections, since the assembly packet(s) convey timing information outwards from connected nodes.

The network nodes can be mesh network appliances to provide voice communications, home security, door access control, lighting control, power outlet control, dimmer control, switch control, temperature control, humidity control, carbon monoxide control, fire alarm control, blind control, shade control, window control, oven control, cooking range control, personal computer control, entertainment console control, television control, projector control, garage door control, car control, pool temperature control, water pump control, furnace control, heater control, thermostat control, electricity meter monitor, water meter monitor, gas meter monitor, or remote diagnostics. The telephone can be connected to a cellular telephone to answer calls directed at the cellular telephone. The connection can be wired or wireless using Bluetooth or ZigBee. The telephone synchronizes calendar, contact, emails, blogs, or instant messaging with the cellular telephone. Similarly, the telephone synchronizes calendar, contact, emails, blogs, or instant messaging with a personal computer. A web server can communicate with the Internet through the POTS to provide information to an authorized remote user who logs into the server. A wireless router such as 802.11 router, 802.16 router, WiFi router, WiMAX router, Bluetooth router, X10 router can be connected to the mesh network.

A mesh network appliance can be connected to a power line to communicate X10 data to and from the mesh network. X10 is a communication protocol that allows up to 256 X10 products to talk to each other using the existing electrical wiring in the home. Typically, the installation is simple, a transmitter plugs (or wires) in at one location in the home and sends its control signal (on, off, dim, bright, etc.) to a receiver which plugs (or wires) into another location in the home. The mesh network appliance translates messages intended for X10 device to be relayed over the ZigBee wireless network, and then transmitted over the power line using a ZigBee to X10 converter appliance.

Figure 8:
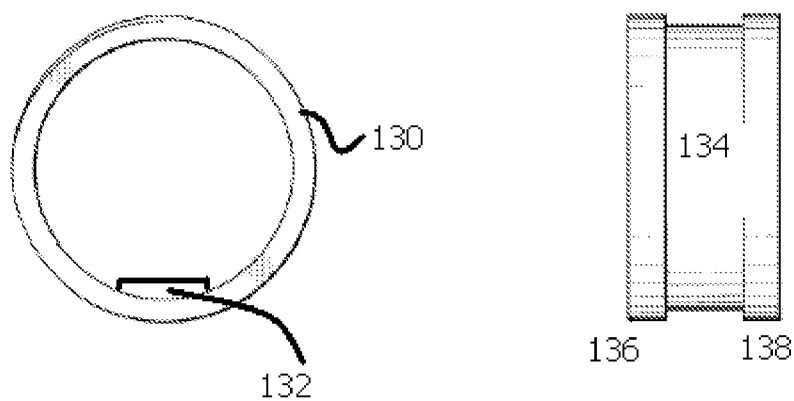

Turning now to FIGS. 8-13, various exemplary monitoring devices are shown. In FIG. 8, a ring 130 has an opening 132 for transmitting and receiving acoustic energy to and from the sensor 84 in an acoustic implementation. In an optical implementation, a second opening (not shown) is provided to emit an optical signal from an LED, for example, and an optical detector can be located at the opening 132 to receive the optical signal passing through the finger wearing the ring 130. In another implementation, the ring has an electrically movable portion 134 and rigid portions 136-138 connected thereto. The electrically movable portion 134 can squeeze the finger as directed by the CPU during an applanation sweep to determine the arterial blood pressure.

Figure 9:
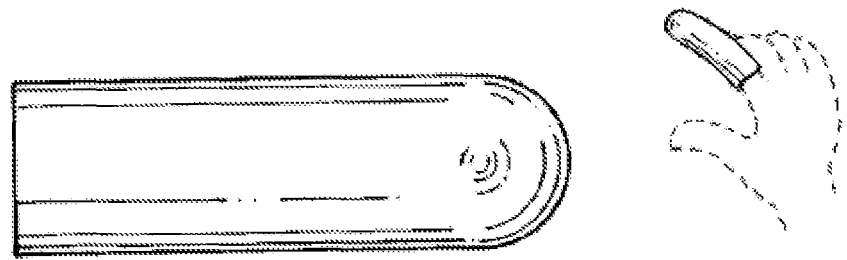

FIG. 9 shows an alternate finger cover embodiment where a finger-mounted module housing the photo-detector and light source. The finger mounted module can be used to measure information that is processed to determine the user's blood pressure by measuring blood flow in the user's finger and sending the information through a wireless connection to the base station. In one implementation, the housing is made from a flexible polymer material.

Figure 10:
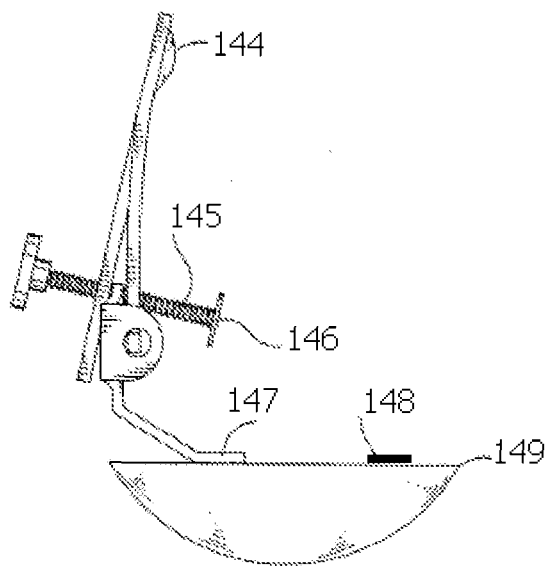

In an embodiment to be worn on the patient's ear lobe, the monitoring device can be part of an earring jewelry clipped to the ear lobe. In the implementation of FIG. 10, the monitoring device has a jewelry body 149 that contains the monitoring electronics and power source. The surface of the body 149 is an ornamental surface such as jade, ivory, pearl, silver, or gold, among others. The body 149 has an opening 148 that transmits energy such as optical or acoustic energy through the ear lobe to be detected by a sensor 144 mounted on a clamp portion that is secured to the body 149 at a base 147. The energy detected through the sensor 144 is communicated through an electrical connector to the electronics in the jewelry body 149 for processing the received energy and for performing wireless communication with a base station. In FIG. 2E, a bolt 145 having a stop end 146 allows the user to adjust the pressure of the clamp against the ear lobe. In other implementations, a spring biased clip is employed to retain the clip on the wearer's ear lobe. A pair of members, which snap together under pressure, are commonly used and the spring pressure employed should be strong enough to suit different thicknesses of the ear lobe.

Figure 11:
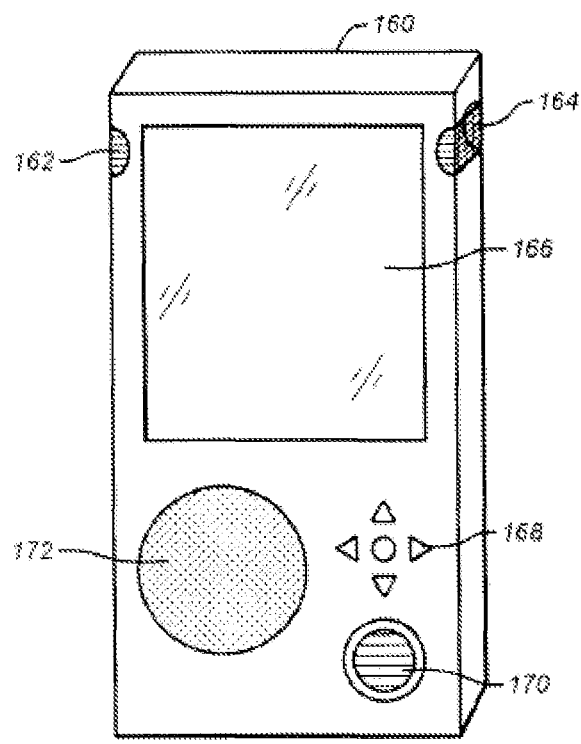
Figure 12:
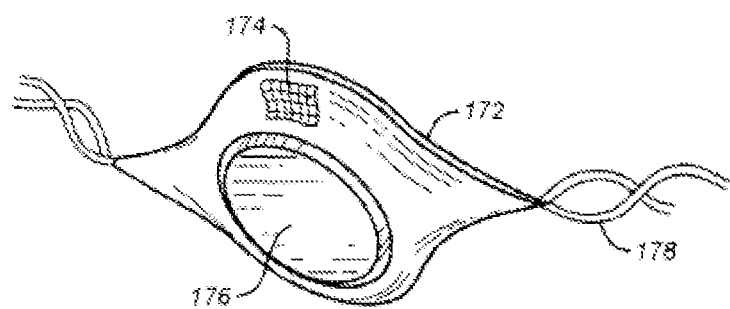

FIGS. 11 and 12 show two additional embodiments of the monitoring device. In FIG. 11, a wearable monitoring device is shown. The monitoring device has a body 160 comprising microphone ports 162, 164 and 170 arranged in a first order noise cancelling microphone arrangement. The microphones 162 and 164 are configured to optimally receive distant noises, while the microphone 170 is optimized for capturing the user's speech. A touch sensitive display 166 and a plurality of keys 168 are provided to capture hand inputs. Further, a speaker 172 is provided to generate a verbal feedback to the user.

Turning now to FIG. 12, a jewelry-sized monitoring device is illustrated. In this embodiment, a body 172 houses a microphone port 174 and a speaker port 176. The body 172 is coupled to the user via the necklace 178 so as to provide a personal, highly accessible personal computer. Due to space limitations, voice input/output is an important user interface of the jewelry-sized computer. Although a necklace is disclosed, one skilled in the art can use a number of other substitutes such as a belt, a brace, a ring, or a band to secure the jewelry-sized computer to the user.

FIG. 13 shows an exemplary ear phone embodiment 180. The ear phone 180 has an optical transmitter 182 which emits LED wavelengths that are received by the optical receiver 184. The blood oximetry information is generated and used to determine blood pulse or blood pressure. Additionally, a module 186 contains mesh network communication electronics, accelerometer, and physiological sensors such as EKG/ECG sensors or temperature sensors or ultrasonic sensors. In addition, a speaker (not shown) is provided to enable voice communication over the mesh network, and a microphone 188 is provided to pick up voice during verbal communication and pick up heart sound when the user is not using the microphone for voice communication. The ear phone optionally has an ear canal temperature sensor for sensing temperature in a human.

FIG. 14A shows an exemplary adhesive patch embodiment. The patch may be applied to a persons skin by anyone including the person themselves or an authorized person such as a family member or physician. The adhesive patch is shown generally at 190 having a gauze pad 194 attached to one side of a backing 192, preferably of plastic, and wherein the pad can have an impermeable side 194 coating with backing 192 and a module 196 which contains electronics for communicating with the mesh network and for sensing acceleration and bioimpedance, EKG/ECG, heart sound, microphone, optical sensor, or ultrasonic sensor in contacts with a wearer's skin. In one embodiment, the module 196 has a skin side that may be coated with a conductive electrode lotion or gel to improve the contact. The entire patch described above may be covered with a plastic or foil strip to retain moisture and retard evaporation by a conductive electrode lotion or gel provided improve the electrode contact. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. The entire patch is then packaged as sterile as are other over-the-counter adhesive bandages. When the patch is worn out, the module 196 may be removed and a new patch backing 192 may be used in place of the old patch. One or more patches may be applied to the patient's body and these patches may communicate wirelessly using the mesh network or alternatively they may communicate through a personal area network using the patient's body as a communication medium.

The term "positional measurement," as that term is used herein, is not limited to longitude and latitude measurements, or to metes and bounds, but includes information in any form from which geophysical positions can be derived. These include, but are not limited to, the distance and direction from a known benchmark, measurements of the time required for certain signals to travel from a known source to the geophysical location where the signals may be electromagnetic or other forms, or measured in terms of phase, range, Doppler or other units.

FIG. 14B shows a sunglass or eyeglass embodiment which contains electronics for communicating with the mesh network and for sensing acceleration and bioimpedance, EKG/ECG, EMG, heart sound, microphone, optical sensor, or ultrasonic sensor in contacts with a wearer's skin. In one embodiment, the ear module 310 contains optical sensors to detect temperature, blood flow and blood oxygen level as well as a speaker to provide wireless communication or hearing aid. The blood flow or velocity information can be used to estimate blood pressure. The side module 312 can contain an array of bioimpedance sensors such as bipolar or tetrapolar bioimpedance probes to sense fluids in the brain. Additional bioimpedance electrodes can be positioned around the rim of the glasses as well as the glass handle or in any spots on the eyewear that contacts the user. The side module 312 or 314 can also contain one or more EKG electrodes to detect heart beat parameters and to detect heart problems. The side module 312 or 314 can also contain piezoelectric transducers or microphones to detect heart activities near the brain. The side module 312 or 314 can also contain ultrasound transmitter and receiver to create an ultrasound model of brain fluids. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. In another embodiment, electronics components are distributed between first and second ear stems. In yet another embodiment, the method further comprises providing a nose bridge, wherein digital signals generated by the electronics circuit are transmitted across the nose bridge. The eyewear device may communicate wirelessly using the mesh network or alternatively they may communicate through a personal area network using the patient's body as a communication medium. Voice can be transmitted over the mesh wireless network. The speaker can play digital audio file, which can be compressed according to a compression format. The compression format may be selected from the group consisting of: PCM, DPCM, ADPCM, AAC, RAW, DM, RIFF, WAV, BWF, RIFF, AU, SND, CDA, MPEG, MPEG-1, MPEG-2, MPEG-2.5, MPEG-4, MPEG-J, MPEG 2-ACC, MP3, MP3Pro, ACE, MACE, MACE-3, MACE-6, AC-3, ATRAC, ATRAC3, EPAC, Twin VQ, VQF, WMA, WMA with DRM, DTS, DVD Audio, SACD, TAC, SHN, OGG, Ogg Vorbis, Ogg Tarkin, Ogg Theora, ASF, LQT, QDMC, A2b, .ra, .rm, and Real Audio G2, RMX formats, Fairplay, Quicktime, SWF, and PCA, among others.

In one embodiment, the eye wear device of FIG. 14B can provide a data port, wherein the data port is carried by the ear stem. The data port may be a mini-USB connector, a FIREWIRE connector, an IEEE 1394 cable connector, an RS232 connector, a JTAB connector, an antenna, a wireless receiver, a radio, an RF receiver, or a Bluetooth receiver. In another embodiment, the wearable device is removably connectable to a computing device. The wearable wireless audio device may be removably connectable to a computing device with a data port, wherein said data port is mounted to said wearable wireless audio device. In another embodiment, projectors can project images on the glasses to provide head-mounted display on the eye wear device. The processor can display fact, figure, to do list, and reminders need in front of the user's eyes.

Figure 15A:
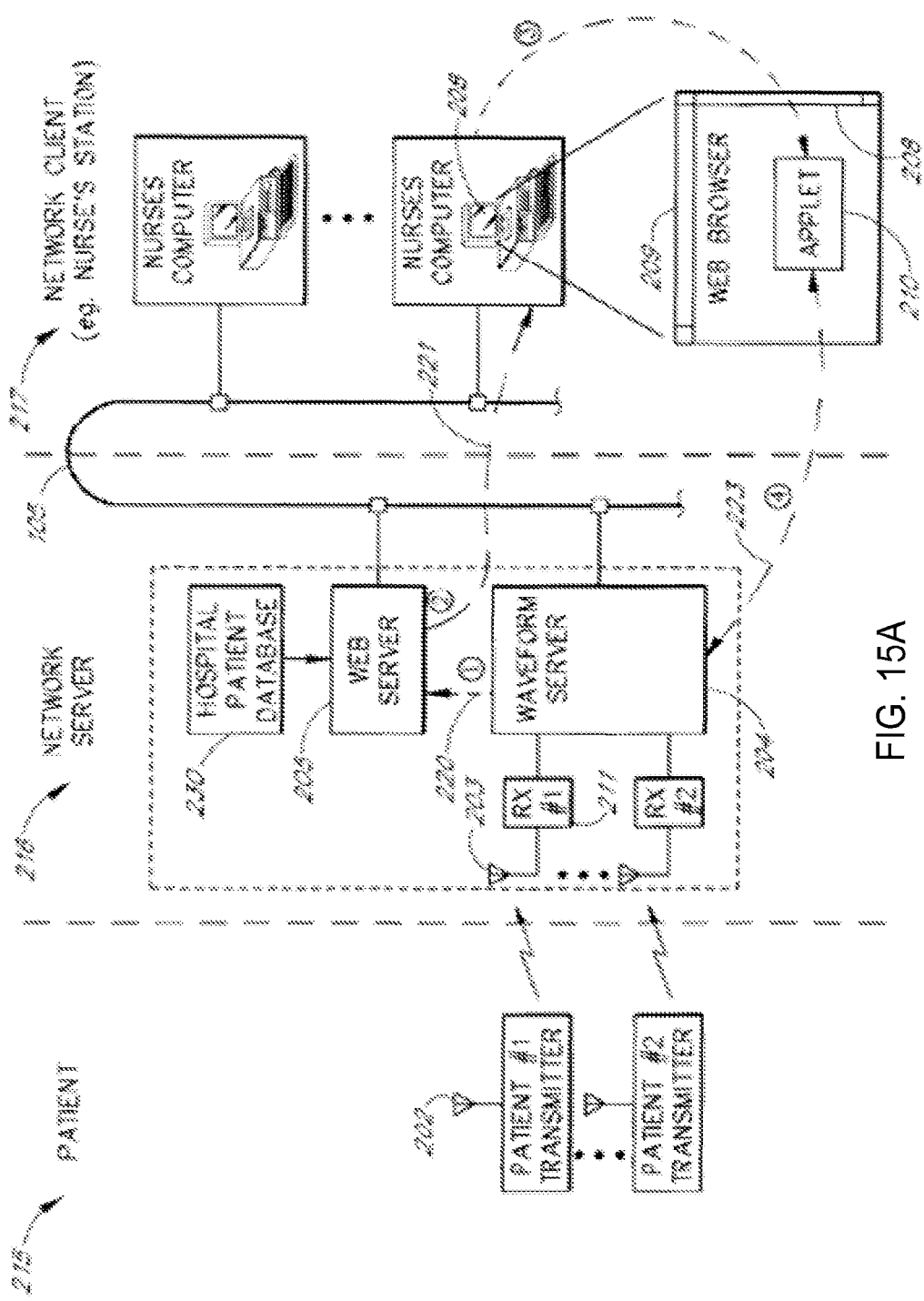
FIGS. 15A-15B show exemplary systems for performing patient monitoring.

FIG. 15A shows a system block diagram of the network-based patient monitoring system in a hospital or nursing home setting. The system has a patient component 215, a server component 216, and a client component 217. The patient component 215 has one or more mesh network patient transmitters 202 for transmitting data to the central station. The central server comprises one or more Web servers 205, one or more waveform servers 204 and one or more mesh network receivers 211. The output of each mesh network receiver 211 is connected to at least one of the waveform servers 204. The waveform servers 204 and Web the servers 205 are connected to the network 105. The Web servers 205 are also connected to a hospital database 230. The hospital database 230 contains patient records. In the embodiment of FIG. 15A, a plurality of nurse stations provide a plurality of nurse computer user interface 208. The user interface 208 receives data from an applet 210 that communicates with the waveform server 204 and updates the display of the nurse computers for treating patients.

The network client component 217 comprises a series of workstations 106 connected to the network 105. Each workstation 106 runs a World Wide Web (WWW or Web) browser application 208. Each Web browser can open a page that includes one or more media player applets 210. The waveform servers 204 use the network 105 to send a series of messages 220 to the Web servers 205. The Web servers 205 use the network 105 to communicate messages, shown as a path 221, to the workstations 106. The media player applets running on the workstations 106 use the network 105 to send messages over a path 223 directly to the waveform servers 204.

Figure 15B:
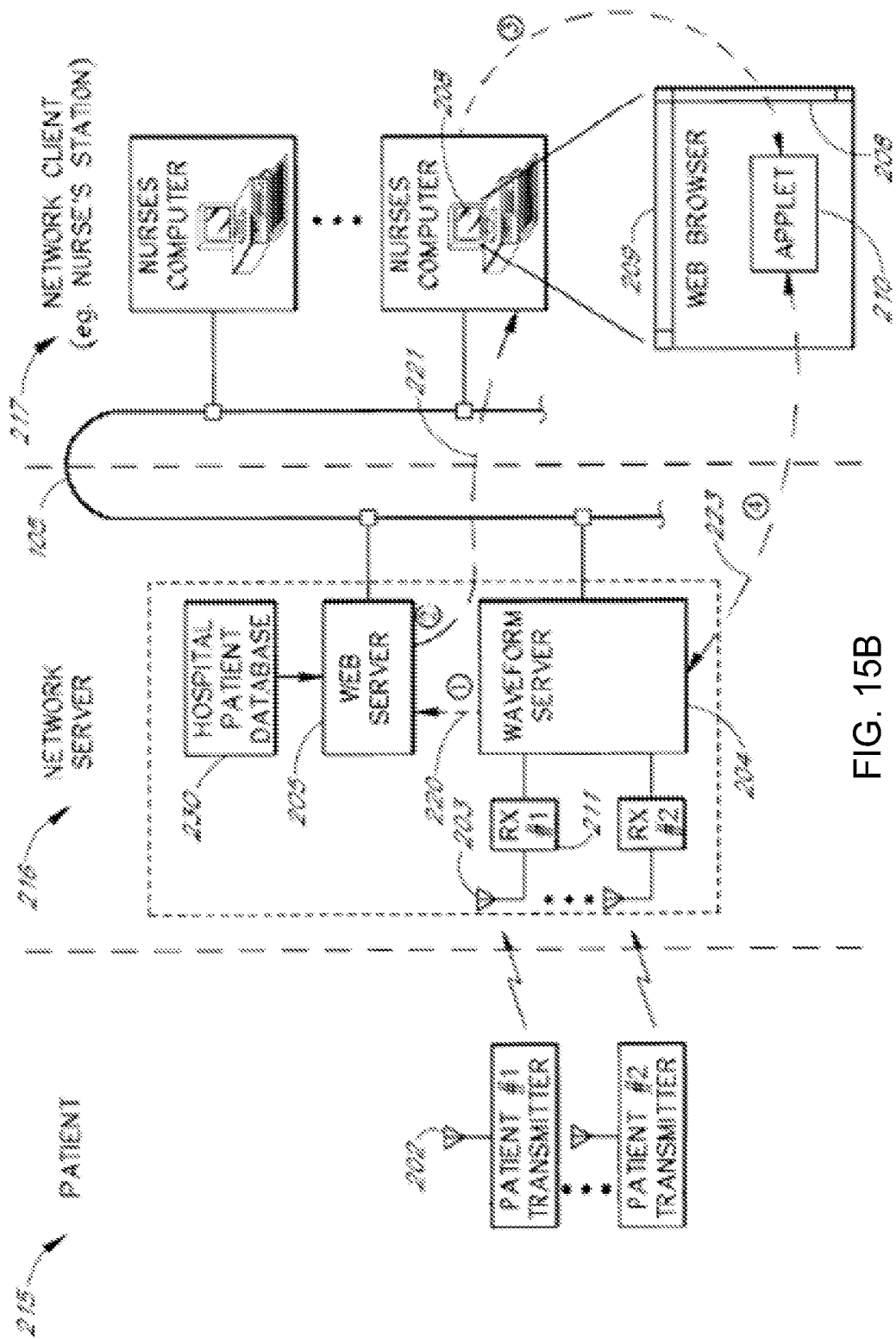

FIG. 15B shows a variation of the system of FIG. 15A for call center monitoring. In this embodiment, the patient appliances 202 wirelessly communicate to home base stations (not shown) which are connected to the POTS or PSTN network for voice as well as data transmission. The data is captured by the waveform server 204 and the voice is passed through to the call center agent computer 207 where the agent can communicate by voice with the patient. The call center agent can forward the call to a professional such as a nurse or doctor or emergency service personnel if necessary. Hence, the system can include a patient monitoring appliance coupled to the POTS or PSTN through the mesh network. The patient monitoring appliance monitors drug usage and patient falls. The patient monitoring appliance monitors patient movement. A call center can call to the telephone to provide a human response.

In one exemplary monitoring service providing system, such as an emergency service providing system, the system includes a communication network (e.g., the Public Switch Telephone Network or PSTN or POTS), a wide area communication network (e.g., TCP/IP network) in call centers. The communication network receives calls destined for one of the call centers. In this regard, each call destined for one of the call centers is preferably associated with a particular patient, a call identifier or a call identifier of a particular set of identifiers. A call identifier associated with an incoming call may be an identifier dialed or otherwise input by the caller. For example, the call centers may be locations for receiving calls from a particular hospital or nursing home.

To network may analyze the automatic number information (ANI) and/or automatic location information (ALI) associated with the call. In this regard, well known techniques exist for analyzing the ANI and ALI of an incoming call to identify the call as originating from a particular calling device or a particular calling area. Such techniques may be employed by the network to determine whether an incoming call originated from a calling device within an area serviced by the call centers. Moreover, if an incoming call originated from such an area and if the incoming call is associated with the particular call identifier referred to above, then the network preferably routes the call to a designated facility.

When a call is routed to the facility, a central data manager, which may be implemented in software, hardware, or a combination thereof, processes the call according to techniques that will be described in more detail hereafter and routes the call, over the wide area network, to one of the call centers depending on the ANI and/or ALI associated with the call. In processing the call, the central data manager may convert the call from one communication protocol to another communication protocol, such as voice over internet protocol (VOIP), for example, in order to increase the performance and/or efficiency of the system. The central data manager may also gather information to help the call centers in processing the call. There are various techniques that may be employed by the central data manager to enhance the performance and/or efficiency of the system, and examples of such techniques will be described in more detail hereafter.

Various benefits may be realized by utilizing a central facility to intercept or otherwise receive a call from the network and to then route the call to one of the call centers via WAN. For example, serving multiple call centers with a central data manager, may help to reduce total equipment costs. In this regard, it is not generally necessary to duplicate the processing performed by the central data manager at each of the call centers. Thus, equipment at each of the call centers may be reduced. As more call centers are added, the equipment savings enabled by implementing equipment at the central data manager instead of the call centers generally increases. Furthermore, the system is not dependent on any telephone company's switch for controlling the manner in which data is communicated to the call centers. In this regard, the central data manager may receive a call from the network and communicate the call to the destination call centers via any desirable communication technique, such as VOIP, for example. Data security is another possible benefit of the exemplary system 10 as the central data manager is able to store the data for different network providers associated with network on different partitions.

Figure 15C:
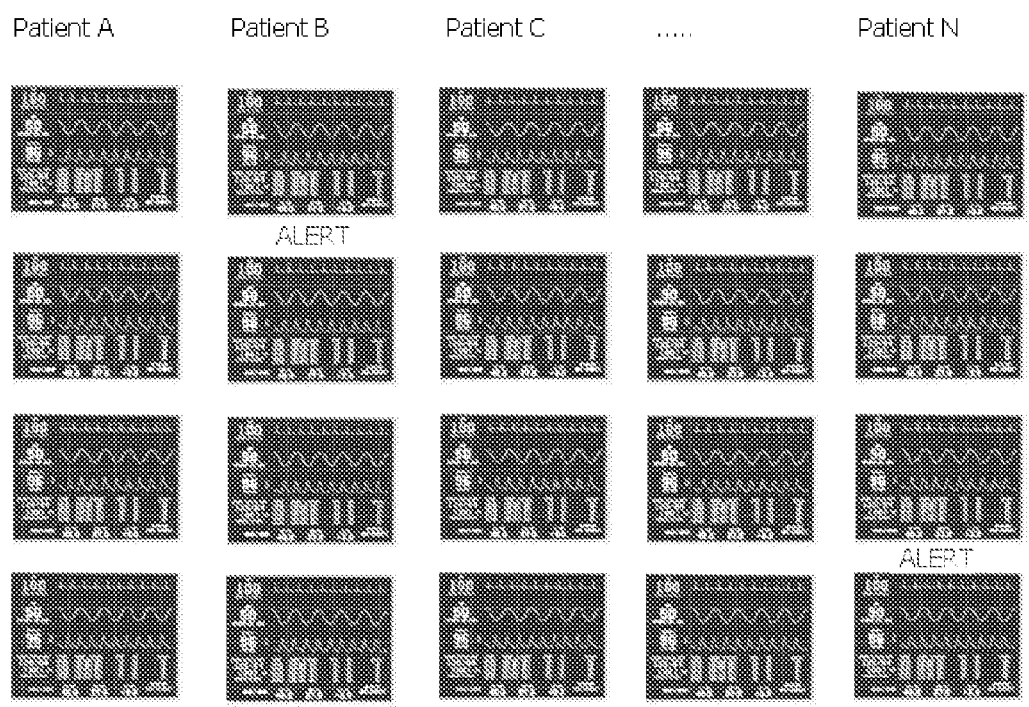
FIG. 15C shows an exemplary interface to monitor a plurality of persons.
Figure 15D:
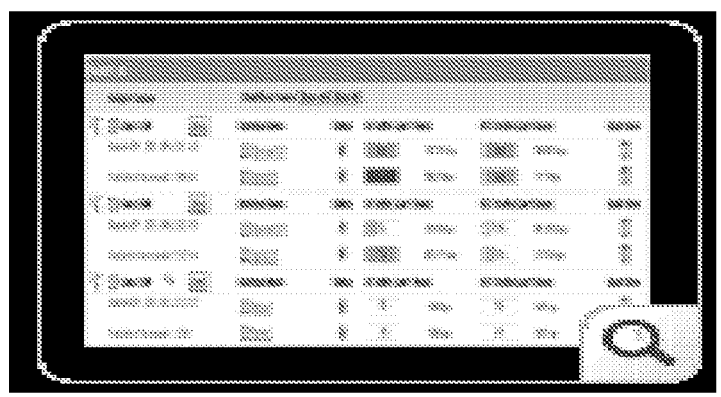
FIG. 15D shows an exemplary dash-board that provides summary information on the status of a plurality of persons.

While the patient interface 90 (FIG. 1A) can provide information for a single person, FIG. 15C shows an exemplary interface to monitor a plurality of persons, while FIG. 15D shows an exemplary dash-board that provides summary information on the status of a plurality of persons. As shown in FIG. 1C, for professional use such as in hospitals, nursing homes, or retirement homes, a display can track a plurality of patients. In FIG. 15C, a warning (such as sound or visual warning in the form of light or red flashing text) can be generated to point out the particular patient that may need help or attention. In FIG. 15D, a magnifier glass can be dragged over a particular individual icon to expand and show detailed vital parameters of the individual and if available, images from the camera 10 trained on the individual for real time video feedback. The user can initiate voice communication with the user for confirmation purposes by clicking on a button provided on the interface and speaking into a microphone on the professional's workstation.

Figure 15E:
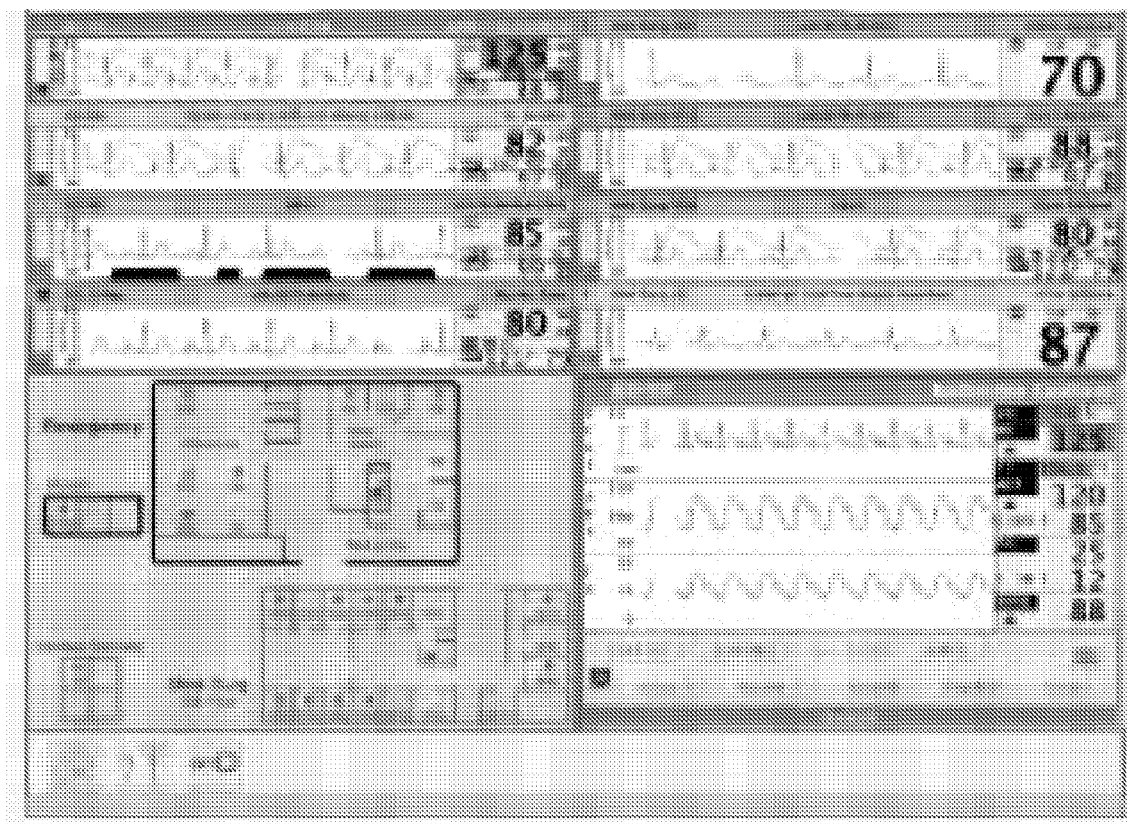
FIG. 15E shows an exemplary multi-station vital parameter user interface for a professional embodiment.
Figure 15F:
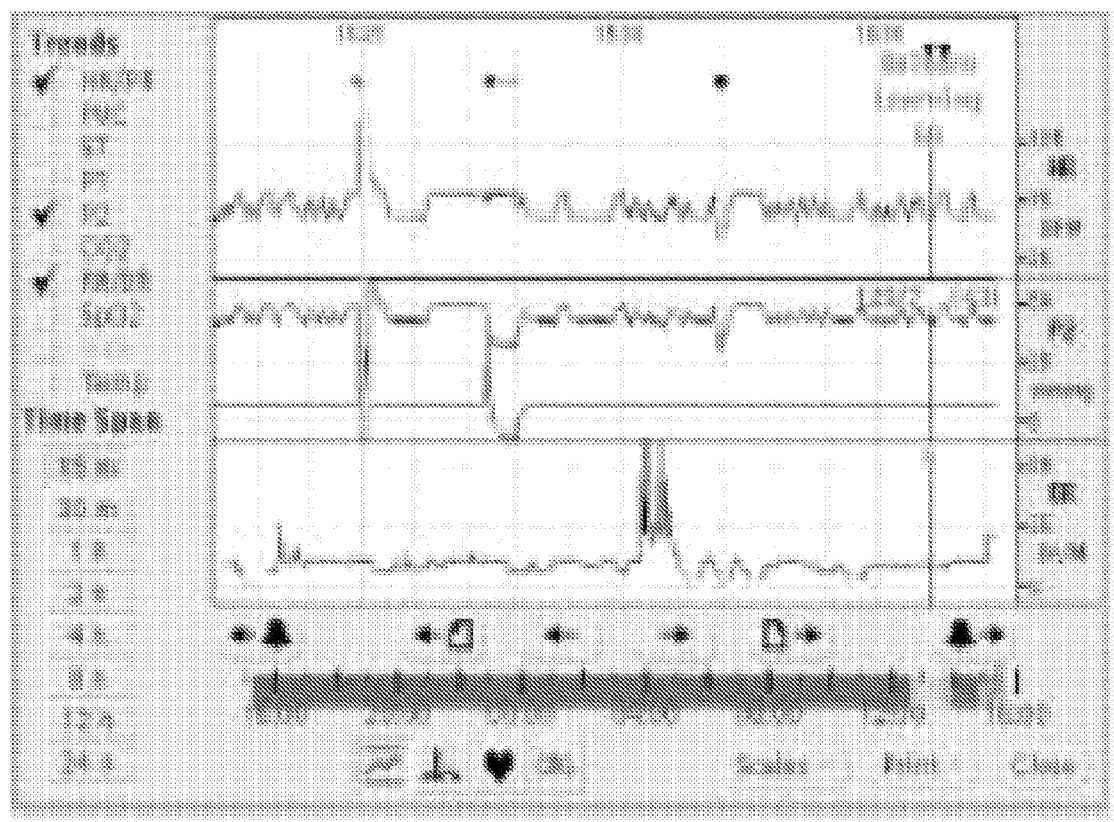
FIG. 15F shows an exemplary trending pattern display.

In one embodiment for professional users such as hospitals and nursing homes, a Central Monitoring Station provides alarm and vital sign oversight for a plurality of patients from a single computer workstation. FIG. 15E shows an exemplary multi-station vital parameter user interface for a professional embodiment, while FIG. 15F shows an exemplary trending pattern display. The clinician interface uses simple point and click actions with a computer mouse or trackball. The clinician can initiate or change monitoring functions from either the Central Station or the bedside monitor. One skilled in the art will recognize that patient data such as EKG/EMG/EEG/BP data can be shown either by a scrolling waveform that moves along the screen display, or by a moving bar where the waveform is essentially stationary and the bar moves across the screen.

In one embodiment, software for the professional monitoring system provides a login screen to enter user name and password, together with database credentials. In Select Record function, the user can select a person, based on either entered or pre-selected criteria. From here navigate to their demographics, medical record, etc. The system can show a persons demographics, includes aliases, people involved in their care, friends and family, previous addresses, home and work locations, alternative numbers and custom fields. The system can show all data elements of a person's medical record. These data elements are not 'hard wired', but may be configured in the data dictionary to suit particular user requirements. It is possible to create views of the record that filter it to show (for instance) just the medications or diagnosis, etc. Any data element can be designated 'plan able' in the data dictionary and then scheduled. A Summary Report can be done. Example of a report displayed in simple format, selecting particular elements and dates. As many of these reports as required can be created, going across all data in the system based on some criteria, with a particular selection of fields and sorting, grouping and totaling criteria. Reports can be created that can format and analyze any data stored on the server. The system supports OLE controls and can include graphs, bar codes, etc. These can be previewed on screen, printed out or exported in a wide variety of formats. The system also maintains a directory of all organizations the administrator wishes to record as well as your own. These locations are then used to record the location for elements of the medical record (where applicable), work addresses for people involved in the care and for residential addresses for people in residential care. The data elements that form the medical record are not 'hard wired' (ie predefined) but may be customized by the users to suit current and future requirements.

In one embodiment, the wearable appliance can store patient data in its data storage device such as flash memory. The data can include Immunizations and dates; medications (prescriptions and supplements); physician names, addresses, phone numbers, email addresses; location and details of advance directives; insurance company, billing address, phone number, policy number; emergency contacts, addresses, home/business/pager phone numbers, email addresses. The data can include color or black and white photo of the wearer of the device; a thumb print, iris print of other distinguishing physical characteristic; dental records; sample ECG or Cardiac Echo Scan; blood type; present medication being taken; drug interaction precautions; drug and/or allergic reaction precautions; a description of serious preexisting medical conditions; Emergency Medical Instructions, which could include: administering of certain suggested drugs or physical treatments; calling emergency physician numbers listed; bringing the patient to a certain type of clinic or facility based on religious beliefs; and living will instructions in the case of seriously ill patients; Organ Donor instructions; Living Will instructions which could include: instructions for life support or termination of treatment; notification of next of kin and/or friends including addresses and telephone numbers; ECG trace; Cardiac Echo Scan; EEG trace; diabetes test results; x-ray scans, among others. The wearable appliance stores the wearer's medical records and ID information. In one embodiment, to start the process new/original medical information is organized and edited to fit into the BWD page format either in physicians office or by a third party with access to a patient's medical records using the base unit storage and encrypting software which can be stored in a normal pc or other compatible computer device. The system can encrypt the records so as to be secure and confidential and only accessible to authorized individuals with compatible de-encrypting software. In the event the wearer is stricken with an emergency illness a Paramedic, EMT or Emergency Room Technician can use a wireless interrogator to rapidly retrieve and display the stored medical records in the wearable appliance and send the medical records via wireless telemetry to a remote emergency room or physicians office for rapid and life saving medical intervention in a crisis situation. In a Non-emergency Situation, the personal health information service is also helpful as it eliminates the hassle of repeatedly filling out forms when changing health plans or seeing a new physician; stores vaccination records to schools or organizations without calling the pediatrician; or enlists the doctor's or pharmacist's advice about multiple medications without carrying all the bottles to a personal visit. The system can store 48 hrs. of EKG, EEG, EMG, or blood pressure data.

In one embodiment, a plurality of body worn sensors with in-door positioning can be used as an Emergency Department and Urgent Care Center Tracking System. The system tracks time from triage to MD assessment, identifies patients that have not yet been registered, records room usage, average wait time, and average length of stay. The system allows user defined "activities" so that hospitals can track times and assist in improving patient flow and satisfaction. The system can set custom alerts and send email/pager notifications to better identify long patient wait times and record the number of these alert occurrences. The system can manage room usage by identifying those rooms which are under/over utilized. The hospital administrator can set manual or automatic alerts and generate custom reports for analysis of patient flow. The system maximizes revenue by streamlining processes and improving throughput; improves charge capture by ensuring compliance with regulatory standards; increases accountability by collecting clear, meaningful data; enhances risk management and QA; and decreases liability.

Figure 16A:
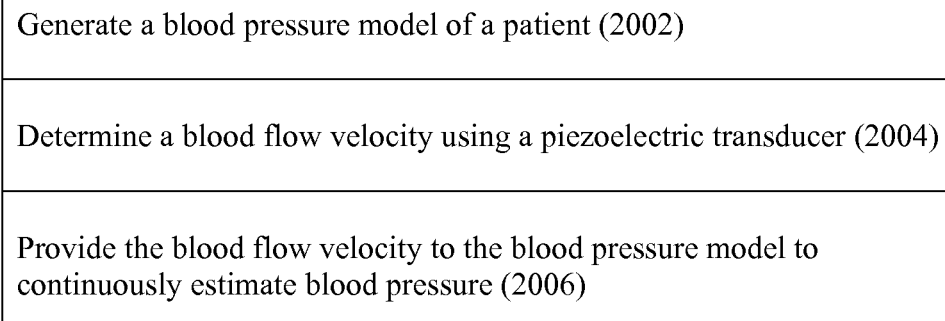
FIGS. 16A-16B show exemplary blood pressure determination processes.

FIG. 16A shows ant exemplary process to continuously determine blood pressure of a patient. The process generates a blood pressure model of a patient (2002); determines a blood flow velocity using a piezoelectric transducer (2004); and provides the blood flow velocity to the blood pressure model to continuously estimate blood pressure (2006).

Figure 16B:
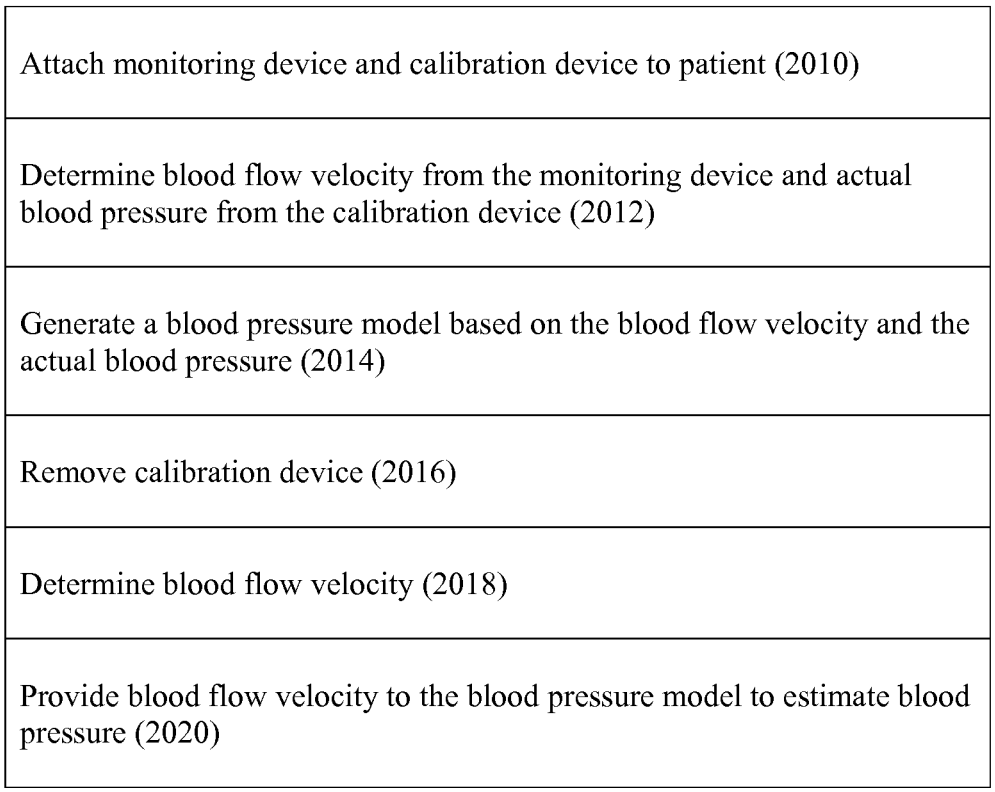

FIG. 16B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and the SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using the wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponds to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of $a(2,2)$, a probability $a(2,3)$ of entering state 3 and a probability of $a(2,4)=1-a(2, 1)-a(2,2)$ of entering state 4. The probability $a(2, 1)$ of entering state 1 or the probability $a(2,5)$ of entering state 5 is zero and the sum of the probabilities $a(2,1)$ through $a(2,5)$ is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

In one embodiment, a heart sound analyzer detects Normal S1, Split S1, Normal S2, Normal split S2, Wide split S2, Paradoxical split S2, Fixed split S2, S3 right ventricle origin, S3 left ventricle origin, opening snap, S4 right ventricle origin, S4 left ventricle origin, aortic ejection sound, and pulmonic ejection sound, among others. The sound analyzer can be an HMM type analyzer, a neural network type analyzer, a fuzzy logic type analyzer, a genetic algorithm type analyzer, a rule-based analyzer, or any suitable classifier. The heart sound data is captured, filtered, and the major features of the heart sound are determined and then operated by a classifier such as HMM or neural network, among others.

The analyzer can detect S1, whose major audible components are related to mitral and tricuspid valve closure. Mitral (MI) closure is the first audible component of the first sound. It normally occurs before tricuspid (T1) closure, and is of slightly higher intensity than T1. A split of the first sound occurs when both components that make up the sound are separately distinguishable. In a normally split first sound, the mitral and tricuspid components are 20 to 30 milliseconds apart. Under certain conditions a wide or abnormally split first sound can be heard. An abnormally wide split first sound can be due to either electrical or mechanical causes, which create asynchrony of the two ventricles. Some of the electrical causes may be right bundle branch block, premature ventricular beats and ventricular tachycardia. An apparently wide split can be caused by another sound around the time of the first. The closure of the aortic and pulmonic valves contributes to second sound production. In the normal sequence, the aortic valve closes before the pulmonic valve. The left sided mechanical events normally precede right sided events.

The system can analyze the second sound S2. The aortic (A2) component of the second sound is the loudest of the two components and is discernible at all auscultation sites, but especially well at the base. The pulmonic (P2) component of the second sound is the softer of the two components and is usually audible at base left. A physiological split occurs when both components of the second sound are separately distinguishable. Normally this split sound is heard on inspiration and becomes single on expiration. The A2 and P2 components of the physiological split usually coincide, or are less than 30 milliseconds apart during expiration and often moved to around 50 to 60 milliseconds apart by the end of inspiration. The physiological split is heard during inspiration because it is during that respiratory cycle that intrathoracic pressure drops. This drop permits more blood to return to the right heart. The increased blood volume in the right ventricle results in a delayed pulmonic valve closure. At the same time, the capacity of the pulmonary vessels in the lung is increased, which results in a slight decrease in the blood volume returning to the left heart. With less blood in the left ventricle, its ejection takes less time, resulting in earlier closing of the aortic valve. Therefore, the net effect of inspiration is to cause aortic closure to occur earlier, and pulmonary closure to occur later. Thus, a split second is heard during inspiration, and a single second sound is heard during expiration. A reversed (paradoxical) split of the second sound occurs when there is a reversal of the normal closure sequence with pulmonic closure occurring before aortic. During inspiration the second sound is single, and during expiration the second sound splits. This paradoxical splitting of the second sound may be heard when aortic closure is delayed, as in marked volume or pressure loads on the left ventricle (i.e., aortic stenosis) or with conduction defects which delay left ventricular depolarization (i.e., left bundle branch block). The normal physiological split second sound can be accentuated by conditions that cause an abnormal delay in pulmonic valve-1 closure. Such a delay may be due to an increased volume in the right ventricle as o compared with the left (atrial septal defect, or ventricular septal defect); chronic right ventricular outflow obstruction (pulmonic stenosis); acute or chronic dilatation of the right ventricle due to sudden rise in pulmonary artery pressure (pulmonary embolism); electrical delay or activation of AA the right ventricle (right bundle branch block); decreased elastic recoil of the pulmonary artery (idiopathic dilatation of the pulmonary artery). The wide split has a duration of 40 to 50' milliseconds, compared to the normal physiologic split of 30 milliseconds. Fixed splitting of the second sound refers to split sound which displays little or no respiratory variation. The two components making up the sound occur in their normal sequence, but the ventricles are unable to change their volumes with respiration. This finding is typical in atrial septal defect, but is occasionally heard in congestive heart failure. The fixed split is heard best at base left with the diaphragm.

The third heart sound is also of low frequency, but it is heard just after the second heart sound. It occurs in early diastole, during the time of rapid ventricular filling. This sound occurs about 140 to 160 milliseconds after the second sound. The S3 is often heard in normal children or young adults but when heard in individuals over the age of 40 it usually reflects cardiac disease characterized by ventricular dilatation, decreased systolic function, and elevated ventricular diastolic filling pressure. The nomenclature includes the term ventricular gallop, protodiastolic gallop, S3 gallop, or the more common, S3. When normal it is referred to as a physiological third heart sound, and is usually not heard past the age of forty. The abnormal, or pathological third heart sound, may be heard in individuals with coronary artery disease, cardiomyopathies, incompetent valves, left to right shunts, Ventricular Septal Defect (VSD), or Patent Ductus Arteriosus (PDA). The pathological S3 may be the first clinical sign of congestive heart failure. The fourth heart sound is a low frequency sound heard just before the first heart sound, usually preceding this sound by a longer interval than that separating the two components of the normal first sound. It has also been known as an "atrial gallop", a "presystolic gallop", and an "S4 gallop". It is most commonly known as an "S4".

The S4 is a diastolic sound, which occurs during the late diastolic filling phase at the time when the atria contract. When the ventricles have a decreased compliance, or are receiving an increased diastolic volume, they generate a low frequency vibration, the S4. Some authorities believe the S4 may be normal in youth, but is seldom considered normal after the age of 20. The abnormal or pathological S4 is heard in primary myocardial disease, coronary artery disease, hypertension, and aortic and pulmonic stenosis. The S4 may have its origin in either the left or right heart. The S4 of left ventricular origin is best heard at the apex, with the patient supine, or in the left lateral recumbent position. Its causes include severe hypertension, aortic stenosis, cardiomyopathies, and left ventricular myocardial infarctions. In association with ischemic heart disease the S4 is often loudest during episodes of angina pectoris or may occur early after an acute myocardial infarction, often becoming fainter as the patient improves. The S4 of right ventricular origin is best heard at the left lateral sternal border. It is usually accentuated with inspiration, and may be due to pulmonary stenosis, pulmonary hypertension, or right ventricular myocardial infarction. When both the third heart sound and a fourth heart sound are present, with a normal heart rate, 60-100 heart beats per minute, the four sound cadence of a quadruple rhythm may be heard.

Ejection sounds are high frequency clicky sounds occurring shortly after the first sound with the onset of ventricular ejection. They are produced by the opening of the semilunar valves, aortic or pulmonic, either when one of these valves is diseased, or when ejection is rapid through a normal valve. They are heard best at the base, and may be of either aortic or pulmonic origin. Ejection sounds of aortic origin often radiate widely and may be heard anywhere on a straight line from the base right to the apex. Aortic ejection sounds are most typically heard in patients with valvular aortic stenosis, but are occasionally heard in various other conditions, such as aortic insufficiency, coarctation of the aorta, or aneurysm of the ascending aorta. Ejection sounds of pulmonic origin are heard anywhere on a straight line from base left, where they are usually best heard, to the epigastrium. Pulmonic ejection sounds are typically heard in pulmonic stenosis, but may be encountered in pulmonary hypertension, atrial septal defects (ASD) or in conditions causing enlargement of the pulmonary artery. Clicks are high frequency sounds which occur in systole, either mid, early, or late. The click generally occurs at least 100 milliseconds after the first sound. The most common cause of the click is mitral valve prolapse. The clicks of mitral origin are best heard at the apex, or toward the left lateral sternal border. The click will move closer to the first sound when volume to the ventricle is reduced, as occurs in standing or the Valsalva maneuver. The opening snap is a short high frequency sound, which occurs after the second heart sound in early diastole. It usually follows the second sound by about 60 to 100 milliseconds. It is most frequently the result of the sudden arrest of the opening of the mitral valve, occurring in mitral stenosis, but may also be encountered in conditions producing increased flow through this valve (i.e., VSD or PDA). In tricuspid stenosis or in association with increased flow across the tricuspid valve, as in ASD, a tricuspid opening snap may be heard. The tricuspid opening snap is loudest at the left lateral sternal border, and becomes louder with inspiration.

Murmurs are sustained noises that are audible during the time periods of systole, diastole, or both. They are basically produced by these factors: 1) Backward regurgitation through a leaking valve or septal defect; 2) Forward flow through a narrowed or deformed valve or conduit or through an arterial venous connection; 3) High rate of blood flow through a normal or abnormal valve; 4) Vibration of loose structures within the heart (i.e., chordae tendineae or valvular tissue). Murmurs that occur when the ventricles are contracting, that is, during systole, are referred to as systolic murmurs. Murmurs occurring when the ventricles are relaxed and filling, that is during diastole, are referred to as diastolic murmurs. There are six characteristics useful in murmur identification and differentiation:

1) Location or the valve area over which the murmur is best heard. This is one clue to the origin of the murmur. Murmurs of mitral origin are usually best heard at the apex. Tricuspid murmurs at the lower left lateral sternal border, and pulmonic murmurs at base left. Aortic systolic murmurs are best heard at base right, and aortic diastolic murmurs at Erb's point, the third intercostal space to the left of the sternum.
2) Frequency (pitch). Low, medium, or high.
3) Intensity.
4) Quality.
5) Timing. (Occurring during systole, diastole, or both).
6) Areas where the sound is audible in addition to the area over which it is heard best.

Systolic murmurs are sustained noises that are audible during the time period of systole, or the period between S1 and S2. Forward flow across the aortic or pulmonic valves, or regurgitant flow from the mitral or tricuspid valve may produce a systolic murmur. Systolic murmurs may be normal, and can represent normal blood flow, i.e., thin chest, babies and children, or increased blood flow, i.e., pregnant women. Early systolic murmurs begin with or shortly after the first sound and peak in the first third of systole. Early murmurs have the greatest intensity in the early part of the cycle. The commonest cause is the innocent murmur of childhood (to be discussed later). A small ventricular septal defect (VSD) occasionally causes an early systolic murmur. The early systolic murmur of a small VSD begins with S1 and stops in mid systole, because as ejection continues and the ventricular size decreases, the small defect is sealed shut, causing the murmur to soften or cease. This murmur is characteristic of the type of children's VSD located in the muscular portion of the ventricular septum. This defect may disappear with age. A midsystolic murmur begins shortly after the first sound, peaks in the middle of systole, and does not quite extend to the second sound. It is the crescendo decrescendo murmur which builds up and decrease symmetrically. It is also known as an ejection murmur. It most commonly is due to forward blood flow through a normal, narrow or irregular valve, i.e., aortic or pulmonic stenosis. The murmur begins when the pressure in the respective ventricle exceeds the aortic or pulmonary arterial pressure. The most characteristic feature of this murmur is its cessation before the second sound, thus leaving this latter sound identifiable as a discrete entity. This type of murmur is commonly heard in normal individuals, particularly in the young, who usually have increased blood volumes flowing over normal valves. In this setting the murmur is usually short, with its peak intensity early in systole, and is soft, seldom over 2 over 6 in intensity. It is then designated as an innocent murmur. In order for a murmur to be classified as innocent (i.e. normal), the following are present:

1) Normal splitting of the second sound together with absence of abnormal sounds or murmurs, such as ejection sounds, diastolic murmurs, etc.
2) Normal jugular venus and carotid pulses
3) Normal precordial pulsations or palpation, and
4) Normal chest x-ray and ECG Obstruction or stenosis across the aortic or pulmonic valves also may give rise to a murmur of this type. These murmurs are usually longer and louder than the innocent murmur, and reach a peak intensity in mid-systole. The murmur of aortic stenosis is harsh in quality and is heard equally well with either the bell or the diaphragm. It is heard best at base right, and radiates to the apex and to the neck bilaterally.

An early diastolic murmur begins with a second sound, and peaks in the first third of diastole. Common causes are aortic regurgitation and pulmonic regurgitation. The early diastolic murmur of aortic regurgitation usually has a high frequency blowing quality, is heard best with a diaphragm at Erb's point, and radiates downward along the left sternal border. Aortic regurgitation tends to be of short duration, and heard best on inspiration. This respiratory variation is helpful in differentiating pulmonic regurgitation from aortic regurgitation. A mid-diastolic murmur begins after the second sound and peaks in mid-diastole. Common causes are mitral stenosis, and tricuspid stenosis. The murmur of mitral stenosis is a low frequency, crescendo de crescendo rumble, heard at the apex with the bell lightly held. If it radiates, it does so minimally to the axilla. Mitral stenosis normally produces three distinct abnormalities which can be heard: 1) A loud first sound 2) An opening snap, and 3) A mid-diastolic rumble with a late diastolic accentuation. A late diastolic murmur occurs in the latter half of diastole, synchronous with atrial contraction, and extends to the first sound. Although occasionally occurring alone, it is usually a component of the longer diastolic murmur of mitral stenosis or tricuspid stenosis. This murmur is low in frequency, and rumbling in quality. A continuous murmur usually begins during systole and extends through the second sound and throughout the diastolic period. It is usually produced as a result of one of four mechanisms: 1) An abnormal communication between an artery and vein; 2) An abnormal communication between the aorta and the right side of the heart or with the left atrium; 3) An abnormal increase in flow, or constriction in an artery; and 4) Increased or turbulent blood flow through veins. Patent Ductus Arteriosus (PDA) is the classical example of this murmur. This condition is usually corrected in childhood. It is heard best at base left, and is usually easily audible with the bell or diaphragm. Another example of a continuous murmur is the so-called venous hum, but in this instance one hears a constant roaring sound which changes little with the cardiac cycle. A late systolic murmur begins in the latter half of systole, peaks in the later third of systole, and extends to the second sound. It is a modified regurgitant murmur with a backward flow through an incompetent valve, usually the mitral valve. It is commonly heard in mitral valve prolapse, and is usually high in frequency (blowing in quality), and heard best with a diaphragm at the apex. It may radiate to the axilla or left sternal border. A pansystolic or holosystolic murmur is heard continuously throughout systole. It begins with the first heart sound, and ends with the second heart sound. It is commonly heard in mitral regurgitation, tricuspid regurgitation, and ventricular septal defect. This type of murmur is caused by backward blood flow. Since the pressure remains higher throughout systole in the ejecting chamber than in the receiving chamber, the murmur is continuous throughout systole. Diastolic murmurs are sustained noises that are audible between S2 and the next S. Unlike systolic murmurs, diastolic murmurs should usually be considered pathological, and not normal. Typical abnormalities causing diastolic murmurs are aortic regurgitation, pulmonic regurgitation, mitral stenosis, and tricuspid stenosis. The timing of diastolic murmurs is the primary concern of this program. These murmurs can be early, mid, late and pan in nature. In a pericardial friction rub, there are three sounds, one systolic, and two diastolic. The systolic sound may occur anywhere in systole, and the two diastolic sounds occur at the times the ventricles are stretched. This stretching occurs in early diastole, and at the end of diastole. The pericardial friction rub has a scratching, grating, or squeaking leathery quality. It tends to be high in frequency and best heard with a diaphragm. A pericardial friction rub is a sign of pericardial inflammation and may be heard in infective pericarditis, in myocardial infarction, following cardiac surgery, trauma, and in autoimmune problems such as rheumatic fever.

In addition to heart sound analysis, the timing between the onset and offset of particular features of the ECG (referred to as an interval) provides a measure of the state of the heart and can indicate the presence of certain cardiological conditions. An EKG analyzer is provided to interpret EKG/ECG data and generate warnings if needed. The analyzer examines intervals in the ECG waveform such as the QT interval and the PR interval. The QT interval is defined as the time from the start of the QRS complex to the end of the T wave and corresponds to the total duration of electrical activity (both depolarization and repolarization) in the ventricles. Similarly, the PR interval is defined as the time from the start of the P wave to the start of the QRS complex and corresponds to the time from the onset of atrial depolarization to the onset of ventricular depolarization. In one embodiment, hidden Markov and hidden semi-Markov models are used for automatically segmenting an electrocardiogram waveform into its constituent waveform features. An undecimated wavelet transform is used to generate an overcomplete representation of the signal that is more appropriate for subsequent modelling. By examining the ECG signal in detail it is possible to derive a number of informative measurements from the characteristic ECG waveform. These can then be used to assess the medical well-being of the patient. The wavelet methods such as the undecimated wavelet transform, can be used instead of raw time series data to generate an encoding of the ECG which is tuned to the unique spectral characteristics of the ECG waveform features. The segmentation process can use of explicit state duration modelling with hidden semi-Markov models. Using a labelled data set of ECG waveforms, a hidden Markov model is trained in a supervised manner. The model was comprised of the following states: P wave, QRS complex, T wave, U wave, and Baseline. The parameters of the transition matrix aij were computed using the maximum likelihood estimates. The ECG data is encoded with wavelets from the Daubechies, Symlet, Coiflet or Biorthogonal wavelet families, among others. In the frequency domain, a wavelet at a given scale is associated with a bandpass filter of a particular centre frequency. Thus the optimal wavelet basis will correspond to the set of bandpass filters that are tuned to the unique spectral characteristics of the ECG. In another implementation, a hidden semi-Markov model (HSMM) is used. HSMM differs from a standard HMM in that each of the self-transition coefficients aii are set to zero, and an explicit probability density is specified for the duration of each state. In this way, the individual state duration densities govern the amount of time the model spends in a given state, and the transition matrix governs the probability of the next state once this time has elapsed. Thus the underlying stochastic process is now a "semi-Markov" process. To model the durations of the various waveform features of the ECG, a Gamma density is used since this is a positive distribution which is able to capture the skewness of the ECG state durations. For each state i, maximum likelihood estimates of the shape and scale parameters were computed directly from the set of labelled ECG signals.

In addition to providing beat-to-beat timing information for other sensors to use, the patterns of the constituent waveform features determined by the HMM or neural networks, among other classifiers, can be used for detecting heart attacks or stroke attacks, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

FIG. 16C shows an exemplary process to detect stroke attack. In this embodiment, 3D accelerometer sensing is used. First, the process looks for weakness (hemiparesis) in either the left half or the right half of the body, for example the left/right arms, legs, or face (3000). Next, the system analyzes walking pattern to see if the patient has a loss of balance or coordination (3002). The system then asks the user to move hands/feet in a predetermined pattern (3004) and reads accelerometer output in accordance with predetermined pattern movement (3006). For example, the system can ask the user to point his/her right or left hand to the nose. The accelerometer outputs are tested to check if the correct hand did reach the nose. In another example, the user can be prompted to extend his or her hands on both side and wiggle the hands or to kick the legs. Again, the outputs of the accelerometers are used to confirm that the user is able to follow direction. The accelerometer outputs are provided to a pattern classifier, which can be an HMM, a neural network, a Bayesian network, fuzzy logic, or any suitable classifiers (3008). The system also checks whether patient is experiencing dizziness or sudden, severe headache with no known cause (3010). Next, the system displays a text image and asks the patient to read back the text image, one eye at a time (3012). Using a speech recognizer module, the user speech is converted into text to compare against the text image. The speech recognizer also detects if the user exhibits signs of confusion, trouble speaking or understanding (3014). The system also asks the patient if they feel numbness in the body-arms, legs, face (3016). Next the system asks the patient to squeeze gauge/force sensor to determine force applied during squeeze (3018). If any of the above tests indicate a possible stroke, the system displays a warning to the patient and also connects the patient to the appropriate emergency response authority, family member, or physician.

Figure 16D:
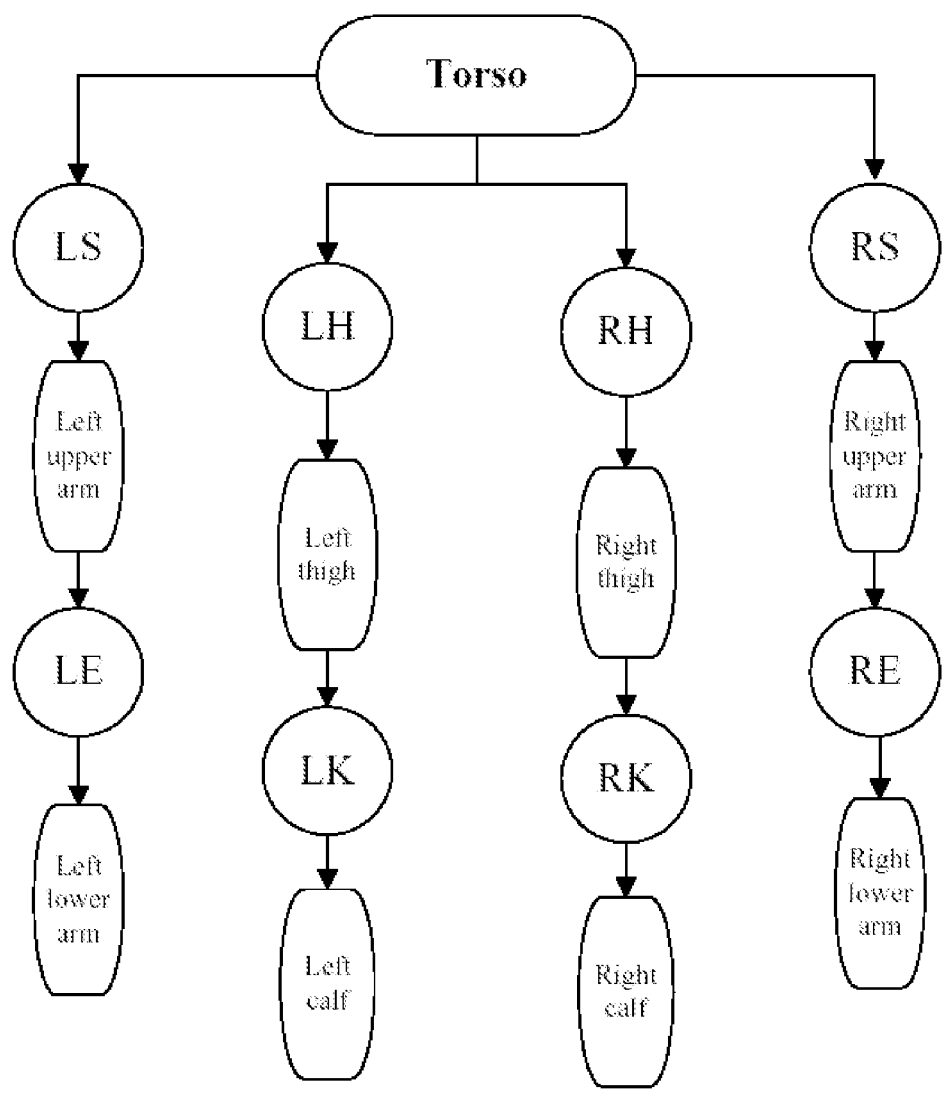

In one implementation, an HMM is used to track patient motor skills or patient movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the patient on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the patient through additional tests to confirm a stroke attack, and if a stroke attack is suspected, the system prompts the user to seek medical attention immediately and preferably within the 3 hour for receiving TPA.

FIG. 16E shows one exemplary process for determining weakness in the left or right half of the body. The process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the patient to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

The system can detect hemiparesis, a very common symptom of stroke, by detecting muscular weakness or partial paralysis to one side of the body. Additionally, the accelerometers can detect ataxia, which is an impaired ability to perform smooth coordinated voluntary movements. Additionally, the system can detect aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by displaying text or playing verbal instructions to the user, followed by measuring the correctness and/or time delay of the response from the user. Exemplary embodiments are also disclosed for detecting expressive aphasia by positing sound made by an animal to the user, prompting the user to identify or name the animal, and measuring the correctness and/or time delay of the response from the user. The system can also detect dysarthria, a disorder of speech articulation (e.g., slurred speech), by prompting the user to say a word or phrase that is recorded for subsequent comparison by voice pattern recognition or evaluation by medical personnel.

In the above manner, the system automatically reminds the user to get help if he feels a sudden numbness or weakness of the face, arm or leg, especially on one side of the body, sudden confusion, trouble speaking or understanding, sudden trouble seeing in one or both eyes, or sudden trouble walking, dizziness, loss of balance or coordination.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a job lifting boxes, among others. In one alternative embodiment, angular position sensors, one on each side of the hip joint, can be used to distinguish lying down, sitting, and standing positions. In another embodiment, the present invention repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

Depending on the severity of the stroke, patients can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Patients with pure motor hemiparesis present with face, arm, and leg weakness. This condition usually affects the extremities equally, but in some cases it affects one extremity more than the other. The most common stroke location in affected patients is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Patients with clumsy-hand dysarthria syndrome experience unilateral hand weakness and dysarthria. The dysarthria is often severe, whereas the hand involvement is more subtle, and patients may describe their hand movements as "awkward." This syndrome is usually caused by an infarct in the pons.

Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction—such as neglect, hemianopsia, aphasia, and gaze preference (opposite the side of weakness)—suggest hemispheric dysfunction with involvement of a superficial territory from an atherothrombotic or embolic occlusion of a mainstem vessel or peripheral branch.

The system can detect a pattern of motor weakness. Ischemia of the cortex supplied by the middle cerebral artery typically causes weakness that (1) is more prominent in the arm than in the leg and (2) involves the distal muscles more than the proximal muscles. Conversely, involvement of an area supplied by the superficial anterior cerebral artery results in weakness that (1) is more prominent in the leg than the arm and (2) involves proximal upper extremity (shoulder) muscles more than distal upper extremity muscles. Flaccid paralysis of both the arm and leg (unilateral) suggests ischemia of the descending motor tracts in the basal ganglia or brainstem. This is often caused by an occlusion of a penetrating artery as a result of small-vessel disease. Once the stroke is detected, intravenous (IV) tissue plasminogen activator (t-PA) needs to be given within 3 hours of symptom onset. An accurate assessment of the timing of the stroke is also crucial. The system keeps track of the timing off the onset of the stroke for this purpose.

One major symptom of a stroke is unexplained weakness or numbness in the muscle. To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the patient is at rest so that EMG data can be accurately captured or to compensate for motion artifacts in the EMG data in accordance with a linear or non-linear compensation table. In yet another embodiment, the EMG data is used to detect muscle fatigue and to generate a warning to the patient to get to a resting place or a notification to a nurse or caregiver to render timely assistance.

The amplitude of the EMG signal is stochastic (random) in nature and can be reasonably represented by a Gausian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

Figure 17A:
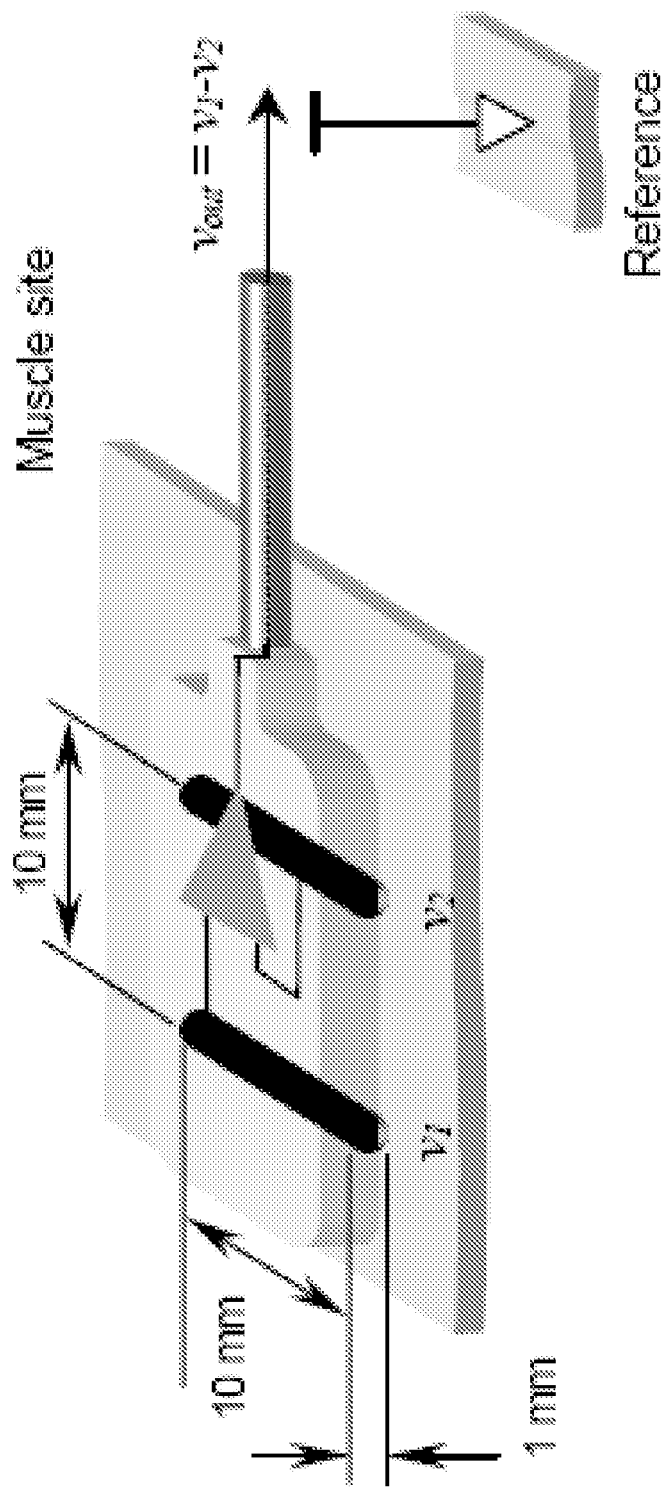
FIG. 17A shows an exemplary EMG sensor.

As shown in FIG. 17A, to eliminate the potentially much greater noise signal from power line sources, a differential instrumentation amplifier is employed. Any signal that originates far away from the detection sites will appear as a common signal, whereas signals in the immediate vicinity of the detection surfaces will be different and consequently will be amplified. Thus, relatively distant power lines noise signals will be removed and relatively local EMG signals will be amplified. The source impedance at the junction of the skin and detection surface may range from several thousand ohms to several megohms for dry skin. In order to prevent attenuation and distortion of the detected signal due to the effects of input loading, the input impedance of the differential amplifier is as large as possible, without causing ancillary complications to the workings of the differential amplifier. The signal to noise ratio is increased by filtering between 20-500 Hz with a roll-off of 12 dB/octave.

In one embodiment, direct EMG pre-amplification at the skin surface provides the best myoelectric signal quality for accurate, reliable EMG signal detection and eliminates cable motion artifact. The double-differential instrumentation pre-amplifier design attenuates unwanted common-mode bio-electric signals to reduce cross-talk from adjacent muscle groups. Internal RFI and ESD protection prevents radio frequency interference and static damage. The constant low-impedance output of the pre-amplifier completely eliminates cable noise and cable motion artifacts without requiring any additional signal processing within the pre-amplifier. An integral ground reference plane provides immunity to electromagnetic environmental noise. All signal and power conductors in the pre-amplifier cable are enclosed inside an independent, isolated shield to eliminate interference from AC power-lines and other sources. The contacts are corrosion-free, medical grade stainless steel for maximal signal flow. The system uses biocompatible housing and sensor materials to prevent allergic reactions.

In one implementation, MA-311 EMG pre-amplifiers from Motion Lab Systems, Inc., Baton Rouge, La., can be used. The pre-amplifiers incorporate both radio frequency interference (RFI) filters and electrostatic discharge (ESD) protection circuitry resulting in an extraordinarily reliable EMG pre-amplifier that can be used in almost any environment. Featuring a double-differential input, the unique design of the Motion Lab Systems EMG pre-amplifiers enables researchers to produce high-quality, low-noise EMG data from subjects under the most adverse conditions (e.g. on treadmills, using mobile phones etc.) without any skin preparation or subsequent signal processing.

In another implementation, a micro-powered EMG embodiment includes an instrumentation amplifier and an AC coupling that maintains a high CMRR with a gain of about 1000. The electronic circuits are mounted on a flexible circuit board (FPC) with slidable electrode settings that allows differential recording at various distances between the electrodes. The high gain amplifier is placed next to the recording electrodes to achieve high SNR. Battery power provides isolation and low noise at various frequencies that would likely not be fully attenuated by the PSRR and causing alias errors.

The system can detect dominant symptoms of stroke can include weakness or paralysis of the arms and/or legs, incoordination (ataxia), numbness in the arms/legs using accelerometers or EMG sensors. The EMG sensors can detect muscle fatigue and can warn the patient to get to a resting area if necessary to prevent a fall. The system can detect partial/ total loss of vision by asking the patient to read a predetermined phrase and detect slur using speech recognizer. The system can detect loss of consciousness/coma by detecting lack of movement. Voice/speech disturbances are not initially the dominant symptoms in stroke, and the disturbances can be detected by a speech recognizer. In one implementation, the system uses PNL (probabilistic networks library) to detect unusual patient movement/ambulatory activities that will lead to a more extensive check for stroke occurrence. PNL supports dynamic Bayes nets, and factor graphs; influence diagrams. For inference, PNL supports exact inference using the junction tree algorithm, and approximate inference using loopy belief propagation or Gibbs sampling. Learning can be divided along many axes: parameter or structure, directed or undirected, fully observed or partially observed, batch or online, discriminative or maximum likelihood, among others. First, the system performs data normalization and filtering for the accelerometers and EMG sensors that detect patient movements and muscle strength. The data can include in-door positioning information, 3D acceleration information, or EMG/EKG/EEG data, for example. The data can be processed using wavelet as discussed above or using any suitable normalization/filtering techniques. Next, the system performs parameterization and discretization. The Bayesian network is adapted in accordance with a predefined network topology. The system also defines conditional probability distributions. The system then generates the probability of event P(y), under various scenarios. Training data is acquired and a training method is built for the Bayesian network engine. Next, the system tunes model parameters and performs testing on the thus formed Bayesian network.

In one embodiment, a housing (such as a strap, a wristband, or a patch) provides a plurality of sensor contacts for EKG and/or EMG. The same contacts can be used for detecting EKG or EMG and can be placed as two parallel contacts (linear or spot shape) on opposite sides of the band, two adjacent parallel contacts on the inner surface of the band, two parallel adjacent contacts on the back of the wrist-watch, or alternatively one contact on the back of the watch and one contact on the wrist-band. The outputs of the differential contacts are filtered to remove motion artifacts. The differential signal is captured, and suitably filtered using high pass/low pass filters to remove noise, and digitized for signal processing. In one embodiment, separate amplifiers are used to detect EKG (between 50 mHz and 200 Hz) and for EMG (between 10 Hz and 500 Hz). In another embodiment, one common amp is used for both EKG/EMG, and software filter is applied to the digitized signal to extract EKG and EMG signals, respectively. The unit can apply Wavelet processing to convert the signal into the frequency domain and apply recognizers such as Bayesian, NN or HMM to pull the EMG or EKG signals from noise. The system uses a plurality of wireless nodes to transmit position and to triangulate with the mobile node to determine position. 3D accelerometer outputs can be integrated to provide movement vectors and positioning information. Both radio triangulation and accelerometer data can confirm the position of the patient. The RF signature of a plurality of nodes with known position can be used to detect proximity to a particular node with a known position and the patient's position can be extrapolated therefrom.

In one embodiment, Analog Device's AD627, a micropower instrumentation amplifier, is used for differential recordings while consuming low power. In dual supply mode, the power rails Vs can be as low as ±1.1 Volt, which is ideal for battery-powered applications. With a maximum quiescent current of 85 µA (60 µA typical), the unit can operate continuously for several hundred hours before requiring battery replacement. The batteries are lithium cells providing 3.0V to be capable of recording signals up to +1 mV to provide sufficient margin to deal with various artifacts such as offsets and temperature drifts. The amplifier's reference is connected to the analog ground to avoid additional power consumption and provide a low impedance connection to maintain the high CMRR. To generate virtual ground while providing low impedance at the amplifier's reference, an additional amplifier can be used. In one implementation, the high-pass filtering does not require additional components since it is achieved by the limits of the gain versus frequency characteristics of the instrumentation amplifier. The amplifier has been selected such that with a gain of 60 dB, a flat response could be observed up to a maximum of 100 Hz with gain attenuation above 100 Hz in one implementation. In another implementation, a high pass filter is used so that the cut-off frequency becomes dependent upon the gain value of the unit. The bootstrap AC-coupling maintains a much higher CMRR so critical in differential measurements. Assuming that the skin-electrode impedance may vary between 5 K- and 10 K-ohms, 1 M-ohm input impedance is used to maintain loading errors below acceptable thresholds between 0.5% and 1%.

When an electrode is placed on the skin, the detection surfaces come in contact with the electrolytes in the skin. A chemical reaction takes place which requires some time to stabilize, typically in the order of a few seconds. The chemical reaction should remain stable during the recording session and should not change significantly if the electrical characteristics of the skin change from sweating or humidity changes. The active electrodes do not require any abrasive skin preparation and removal of hair. The electrode geometry can be circular or can be elongated such as bars. The bar configuration intersects more fibers. The inter detection-surface distance affects the bandwidth and amplitude of the EMG signal; a smaller distance shifts the bandwidth to higher frequencies and lowers the amplitude of the signal. An inter detection-surface of 1.0 cm provides one configuration that detects representative electrical activity of the muscle during a contraction. The electrode can be placed between a motor point and the tendon insertion or between two motor points, and along the longitudinal midline of the muscle. The longitudinal axis of the electrode (which passes through both detection surfaces) should be aligned parallel to the length of the muscle fibers. The electrode location is positioned between the motor point (or innervation zone) and the tendinous insertion, with the detection surfaces arranged so that they intersect as many muscle fibers as possible.

In one embodiment, a multi-functional bio-data acquisition provides programmable multiplexing of the same differential amplifiers for extracting EEG (electroencephalogram), ECG (electrocardiogram), or EMG (electromyogram) waves. The system includes an AC-coupled chopped instrumentation amplifier, a spike filtering stage, a constant gain stage, and a continuous-time variable gain stage, whose gain is defined by the ratio of the capacitors. The system consumes microamps from 3V. The gain of the channel can be digitally set to 400, 800, 1600 or 2600. Additionally, the bandwidth of the circuit can be adjusted via the bandwidth select switches for different biopotentials. The high cut-off frequency of the circuit can be digitally selected for different applications of EEG acquisition.

In another embodiment, a high-resolution, rectangular, surface array electrode-amplifier and associated signal conditioning circuitry captures electromyogram (EMG) signals. The embodiment has a rectangular array electrode-amplifier followed by a signal conditioning circuit. The signal conditioning circuit is generic, i.e., capable of receiving inputs from a number of different/interchangeable EMG/EKG/EEG electrode-amplifier sources (including from both monopolar and bipolar electrode configurations). The electrode-amplifier is cascaded with a separate signal conditioner minimizes noise and motion artifact by buffering the EMG signal near the source (the amplifier presents a very high impedance input to the EMG source, and a very low output impedance); minimizes noise by amplifying the EMG signal early in the processing chain (assuming the electrode-amplifier includes signal gain) and minimizes the physical size of this embodiment by only including a first amplification stage near the body. The signals are digitized and transmitted over a wireless network such as WiFI, Zigbee, or Bluetooth transceivers and processed by the base station that is remote from the patient. For either high-resolution monopolar arrays or classical bipolar surface electrode-amplifiers, the output of the electrode-amplifier is a single-ended signal (referenced to the isolated reference). The electrode-amplifier transduces and buffers the EMG signal, providing high gain without causing saturation due to either offset potentials or motion artifact. The signal conditioning circuit provides selectable gain (to magnify the signal up to the range of the data recording/monitoring instrumentation, high-pass filtering (to attenuate motion artifact and any offset potentials), electrical isolation (to prevent injurious current from entering the subject) and low-pass filtering (for anti-aliasing and to attenuate noise out of the physiologic frequency range).

FIGS. 17B and 17C shows exemplary sEMG outputs from a differential amplifier to detect muscle strength. FIG. 17B shows the left and right body EMG signals for the patient in a normal state, while FIG. 17C illustrates a patient with degraded muscle capability. In general, muscle fire in a smooth fashion in normal individuals, with little irritability or fasciculation. Muscles fire symmetrically in healthy state when comparing left and right sides in motion. In general, healthy patients show a greater consistency in muscle patterns than injured patients, with the injured showing a greater increase in variability. Such variations are detected by EMG analyzers.

The EMG signal can be rectified, integrated a specified interval of and subsequently forming a time series of the integrated values. The system can calculate the root-mean-squared (rms) and the average rectified (avr) value of the EMG signal. The system can also determine muscle fatigue through the analysis of the frequency spectrum of the signal. The system can also assess neurological diseases which affect the fiber typing or the fiber cross-sectional area of the muscle. Various mathematical techniques and Artificial Intelligence (AI) analyzer can be applied. Mathematical models include wavelet transform, time-frequency approaches, Fourier transform, Wigner-Ville Distribution (WVD), statistical measures, and higher-order statistics. AI approaches towards signal recognition include Artificial Neural Networks (ANN), dynamic recurrent neural networks (DRNN), fuzzy logic system, Genetic Algorithm (GA), and Hidden Markov Model (HMM).

A single-threshold method or alternatively a double threshold method can be used which compares the EMG signal with one or more fixed thresholds. The embodiment is based on the comparison of the rectified raw signals and one or more amplitude thresholds whose value depends on the mean power of the background noise. Alternatively, the system can perform spectrum matching instead of waveform matching techniques when the interference is induced by low frequency baseline drift or by high frequency noise.

EMG signals are the superposition of activities of multiple motor units. The EMG signal can be decomposed to reveal the mechanisms pertaining to muscle and nerve control. Decomposition of EMG signal can be done by wavelet spectrum matching and principle component analysis of wavelet coefficients where the signal is de-noised and then EMG spikes are detected, classified and separated. In another embodiment, principle components analysis (PAC) for wavelet coefficients is used with the following stages: segmentation, wavelet transform, PCA, and clustering. EMG signal decomposition can also be done using non-linear least mean square (LMS) optimization of higher-order cumulants.

Time and frequency domain approaches can be used. The wavelet transform (WT) is an efficient mathematical tool for local analysis of non-stationary and fast transient signals. One of the main properties of WT is that it can be implemented by means of a discrete time filter bank. The Fourier transforms of the wavelets are referred as WT filters. The WT represents a very suitable method for the classification of EMG signals. The system can also apply Cohen class transformation, Wigner-Ville distribution (WVD), and Choi-Williams distribution or other time-frequency approaches for EMG signal processing.

In Cohen class transformation, the class time-frequency representation is particularly suitable to analyze surface myoelectric signals recorded during dynamic contractions, which can be modeled as realizations of nonstationary stochastic process. The WVD is a time-frequency that can display the frequency as a function of time, thus utilizing all available information contained in the EMG signal. Although the EMG signal can often be considered as quasi-stationary there is still important information that is transited and may be distinguished by WVD. Implementing the WVD with digital computer requires a discrete form. This allows the use of fast Fourier transform (FFT), which produces a discrete-time, discrete-frequency representation. The common type of time frequency distribution is the Short-time Fourier Transform (STFT). The Choi-Williams method is a reduced interference distribution. The STFT can be used to show the compression of the spectrum as the muscle fatigue. The WVD has cross-terms and therefore is not a precise representation of the changing of the frequency components with fatigue. When walls appear in the Choi-William distribution, there is a spike in the original signal. It will decide if the walls contain any significant information for the study of muscle fatigue. In another embodiment, the autoregressive (AR) time series model can be used to study EMG signal. In one embodiment, neural networks can process EMG signal where EMG features are first extracted through Fourier analysis and clustered using fuzzy c-means algorithm. Fuzzy c-means (FCM) is a method of clustering which allows data to belong to two or more clusters. The neural network output represents a degree of desired muscle stimulation over a synergic, but enervated muscle. Error-back propagation method is used as a learning procedure for multilayered, feedforward neural network. In one implementation, the network topology can be the feedforward variety with one input layer containing 256 input neurodes, one hidden layer with two neurodes and one output neurode. Fuzzy logic systems are advantageous in biomedical signal processing and classification. Biomedical signals such as EMG signals are not always strictly repeatable and may sometimes even be contradictory. The experience of medical experts can be incorporated. It is possible to integrate this incomplete but valuable knowledge into the fuzzy logic system, due to the system's reasoning style, which is similar to that of a human being. The kernel of a fuzzy system is the fuzzy inference engine. The knowledge of an expert or well-classified examples are expressed as or transferred to a set of "fuzzy production rules" in the form of IF-THEN, leading to algorithms describing what action or selection should be taken based on the currently observed information. In one embodiment, higher-order statistics (HOS) is used for analyzing and interpreting the characteristics and nature of a random process. The subject of HOS is based on the theory of expectation (probability theory).

In addition to stroke detection, EMG can be used to sense isometric muscular activity (type of muscular activity that does not translate into movement). This feature makes it possible to define a class of subtle motionless gestures to control interface without being noticed and without disrupting the surrounding environment. Using EMG, the user can react to the cues in a subtle way, without disrupting their environment and without using their hands on the interface. The EMG controller does not occupy the user's hands, and does not require them to operate it; hence it is "hands free". The system can be used in interactive computer gaming which would have access to heart rate, galvanic skin response, and eye movement signals, so the game could respond to a player's emotional state or guess his or her level of situation awareness by monitoring eye movements. EMG/EEG signal can be used for man-machine interfaces by directly connecting a person to a computer via the human electrical nervous system. Based on EMG and EEG signals, the system applies pattern recognition system to interpret these signals as computer control commands. The system can also be used for Mime Speech Recognition which recognizes speech by observing the muscle associated with speech and is not based on voice signals but EMG. The MSR realizes unvoiced communication and because voice signals are not used, MSR can be applied in noisy environments; it can support people without vocal cords and aphasics. In another embodiment, EMG and/or electroencephalogram (EEG) features are used for predicting behavioral alertness levels. EMG and EEG features were derived from temporal, frequency spectral, and statistical analyses. Behavioral alertness levels were quantified by correct rates of performance on an auditory and a visual vigilance task, separately. A subset of three EEG features, the relative spectral amplitudes in the alpha (alpha %, 8-13 Hz) and theta (theta %, 4-8 Hz) bands, and the mean frequency of the EEG spectrum (MF) can be used for predicting the auditory alertness level.

In yet a further embodiment for performing motor motion analysis, an HMM is used to determine the physical activities of a patient, to monitor overall activity levels and assess compliance with a prescribed exercise regimen and/or efficacy of a treatment program. The HMM may also measure the quality of movement of the monitored activities. For example, the system may be calibrated or trained in the manner previously described, to recognize movements of a prescribed exercise program. Motor function information associated with the recognized movements may be sent to the server for subsequent review. A physician, clinician, or physical therapist with access to patient data may remotely monitor compliance with the prescribed program or a standardized test on motor skill. For example, patients can take the Wolf Motor Function test and acceleration data is captured on the following tasks:

placing the forearm on a table from the side
    moving the forearm from the table to a box on the table from the side
    extending the elbow to the side
    extending the elbow to the side against a light weight
    placing the hand on a table from the front
    moving the hand from table to box
    flexing the elbow to retrieve a light weight
    lifting a can of water
    lifting a pencil, lifting a paper clip
    stacking checkers, flipping cards
    turning a key in a lock
    folding a towel
    lifting a basket from the table to a shelf above the table.

In one embodiment, the patient information is used for diagnosis and for prescription filling. The patient information can be secured using suitable encryption or other security mechanism such as going through a virtual private network (VPN). In one embodiment, the information is secured to conform to the requirements of Health Insurance Portability and Accountability Act (HIPAA). Also, the system can file electronic claims using the HIPAA standards for medical claims with subtypes for Professional, Institutional, and Dental varieties. The system can automatically provide eligibility inquiry and claim status inquiry, among others.

Next, the system sends the secured patient medical information from the patient computer to a remote computer. A professional such as a doctor or physician assistant or nurse can then remotely examine the patient and review the patient medical information during the examination. During such remotely examination, the professional can listen to the patient's organ with a digital stethoscope, scan a video of the patient, run a diagnostic test on the patient such as blood pressure or sugar level check, for example. The professional can also verbally communicate with the patient over the Internet. Typical examination procedures may include a review of the patient's temperature, examination of the ears, eyes, throat, skin tone, chest cavity and abdominal cavity.

The system can run a plurality of medical rules to assist the professional in arriving at a diagnosis or to confirm the diagnosis. Typically, the majority of medical problems fall into several general categories, such as ear infections, respiratory problems that might include asthma, headaches, sore throats, skeletal injuries, and superficial cuts and abrasions. For common illnesses, the diagnosis and treatment are routine and well known. Certain tests or procedures during the examination are routine, relating to certain criteria. Typically, most patients exhibit similar characteristics and share many common physical conditions. For example, a positive strep test would result in general medications being administered, with patient's having allergic reactions to penicillin being given alternative treatment medications. In another example, the expert system recommends treatments based on the frequency or reoccurrence of similar conditions/treatment in a population. For example, strep may be determined where a sibling has strep, and the same conditions are manifested in the patient being examined, thus leading to the diagnosis of strep without having a test performed to corroborate the diagnosis. A person having been diagnosed with a sinus infection would typically be prescribed a strong antibiotic. Using an expert system to assist in diagnosing and prescribing treatment, the system can identify and propose the treatment of generic or standard problems in a streamlined manner and allowing professionals to focus on complex problems.

In one embodiment, the expert system prompts the patient or the professional to describe the symptoms and chief complaints into generalized groups that can include Accidents—poisonings, Fever, Headache-Throat pain, Chest pain, Abdominal pain, Lumbar pain, Dizziness-Nausea-Vomit, Hemorrhages, Skin modifications, Palpitations, Obstetrics—gynecology, for example. Next, the system associates each chief complaint with a set of signs/symptoms in order to establish the medical case significance and the prioritization of each patient session. On the professional's screen is displayed the set of possible signs/symptoms associated to the chief complaint and by using key questions, the professional selects the signs/symptoms best fitted with what the patient declares.

The system provides guidelines of practice standard that can be presented to a professional who might be faced with a particular condition in a patient. The system provides guidelines and practice standards for various general categories of cardiovascular, endocrinology, general, gastrointestinal, hematology, infectious diseases, neurology, pharmacology, pulmonary, renal, surgery, toxicology, trauma, for example. A relational database stores a plurality of decision support algorithms and prompts treating professionals such as doctors to provide care to patients based upon the any of the decision support algorithms. The system includes algorithms for treating Acalculous Cholecystitis, Acute Pancreatitis Algorithms, Acute Renal Failure—Diagnosis, Acute Renal Failure—Management & Treatment, Adrenal Insufficiency. Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patent Infections, Hypercalcemia Diagnosis and Treatment, Hypercalcemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardiodefibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrythmia, Warfarin, Warfarin Dosin, and Wound Healing Strategies, among others. More details on the exemplary expert system are disclosed in U.S. Pat. No. 6,804,656, the content of which is incorporated by reference.

The expert system can recommend medication prescriptions based on a dosage related to age or weight. For example, a patient that has been diagnosed as having a sore throat that has existed for a certain period of time might be prescribed as receiving antibiotic A, which would be a common antibiotic that would be given in a great majority of similar cases. If medical history showed recent use of antibiotic A, then antibiotic B might be the prevalent choice, and be automatically prescribed. Likewise, a patient that has been diagnosed as having a sore throat with a confirmed presence of strep would receive medication C, or a non penicillin derivative medication D if the patient was allergic to penicillin. Following diagnosis, determination is made as to whether or not medications are prescribed based on drug interaction or drug pharmaco-genetic information, and if medications are so prescribed, then this information is stored in the database and transmitted to a remote pharmacy, which prepares the prescription medication.

In one embodiment, the expert system applies a predetermined fee for each type of diagnoses and treatments based on the frequency or reoccurrence of similar conditions/treatment in a population. For example, a diagnosis of strep would necessarily have included in it the costs of laboratory tests that would be necessary in a certain percentage of the patients. Whether or not the test is performed may be irrelevant, since it is included in the set fee in relation to the frequency used to establish the average cost for the diagnosis. Where pneumonia has been detected, as part of the patient diagnosis, a standardized fixed cost would include the typical x-ray costs that would normally be incurred by a certain percentage of patients that receive such a diagnosis. In such a pricing method, the incentive to order expensive tests without sufficient reason is removed, since the typical tests that are to be performed is automatically factored in to the costs for each patient with a similar diagnosis. The patient's fees and costs are directly routed to the database.

While this invention has been particularly shown and described with references to preferred embodiments thereof, it will be understood by those skilled in the art that various changes in form and details may be made therein without departing from the spirit and scope of the invention as defined by the appended claims.

What is claimed is:
1. A system, comprising:
one or more sensors mounted on a patient;
a wireless transceiver to communicate with a remote station connected to a telephone communication network; and
a processor coupled to the sensor and the wireless transceiver to request assistance if the processor detects a fall by the patient using body signature sequences and automatically requests assistance for the patient using a telephone, and wherein the processor also accepts a physical patient actuation with a button to request assistance, and wherein sequences of human motions are classified into groups of similar postures represented by model-states with a posture model depicting inter-relationships among model-states.

2. The system of claim 1, wherein the processor distinguishes between a fall and normal body movement.

3. The system of claim 1, wherein the processor automatically notifies a third party for assistance upon detecting the fall without a user pressing a button to call for help.

4. The system of claim 1, wherein the processor captures movement activities and comparing the movement activities to fall patterns.

5. The system of claim 1, wherein the processor determines an in-door position of the patient using signals between the wireless transceiver and the remote station.

6. The system of claim 1, wherein the processor determines a fall based on detected motions including one or more changes in height or one or more accelerations associated with movements by the patient.

7. The system of claim 1, wherein the processor waits for a predetermined period to detect if the patient can recover from the fall and automatically requests assistance if the patient is unable to recover from the fall.

8. The system of claim 1, comprising a call center coupled to the processor to provide a human response.

9. The system of claim 1, wherein the processor off-loads processing of accelerometer outputs to the remote computer to conserve battery power.

10. The system of claim 1, wherein the processor includes code to generate an acceleration signature based on sensed acceleration; code to match the acceleration signature with at least one of a plurality of stored acceleration signatures, wherein each stored acceleration signatures corresponds with a type of motion; and code to identify the type of motion based on the matching of the acceleration signature with the stored acceleration signature.

11. A method to monitor a person, comprising:
capturing motions from the person using a wearable device worn by the person;
processing sensor outputs on a processor to determine body signature sequences;
determining a body pattern associated with a dangerous condition from the sensor outputs; and
requesting assistance through a telephone call if a dangerous condition is detected, and wherein sequences of human motions are classified into groups of similar postures represented by model-states with a posture model depicting inter-relationships among model-states.

12. The method of claim 11, wherein the person's motions form a sequence of elemental motions, comprising:
identifying each elemental motion of a sequence of elemental motions of the accelerometer; and
identifying the activity of the patient, comprising matching the sequence of identified elemental motions with a library of stored sequences of elemental motions, wherein each stored sequence of elemental motions corresponds with an activity.

13. The method of claim 11, comprising identifying each elemental motion by:
generating an acceleration signature based on sensed acceleration of the device;
matching the acceleration signature with at least one of a plurality of stored acceleration signatures, wherein each stored acceleration signatures corresponds with a type of motion;
identifying the type of motion of the device based on the matching of the acceleration signature with the stored acceleration signature.

14. The method of claim 11, further comprising refining identification of the activity, comprising analyzing one of: timing of the identified activity, at least one identified location of the identified activity, a rate of change of a location of the patient, or patterns of a plurality of identified activities.

15. A method of automatically requesting assistance for a mobile patient, comprising:
attaching a mobile device with one or more accelerometers on the patient to detect patient motion;
processing accelerometer outputs on a processor;
determining a fall based on detected patient motion; and
automatically requesting assistance from the mobile device on behalf of the patient with a telephone call if help is needed and allowing the patient to manually push a button to request help, and wherein sequences of human motions are classified into groups of similar postures represented by model-states with a posture model depicting inter-relationships among model-states.

16. The method of claim 15, comprising detecting if the patient has fallen based on a plurality of accelerometer signals and indicating the fall if the accelerometer signals indicate that the patient is unable to get up.

17. The method of claim 15, comprising notifying an emergency service for assistance automatically without a user pressing a button to call for help.

18. The method of claim 15, comprising detecting the fall by analyzing changes in height and accelerations associated with the changes in height.

19. The method of claim 15, further comprising:
determining if the patient has fallen based on a plurality of sensor signals indicating changes in height or accelerations associated with the changes in height;
waiting for a predetermined period to detect if the patient can independently recover from the fall; and
requesting assistance if the sensor signals indicate that the patient is unable to independently recover from the fall.

20. A method to provide personal emergency response for a patient, comprising:
wearing a mobile device with a help button and at least one or more accelerometers on the patient to detect patient motion;
determining a fall based on detected motions including one or more changes in height and one or more accelerations associated with movements by the patient;
waiting for a predetermined period to detect if the patient can recover from the fall and automatically requesting assistance with a telephone call if the patient is unable to recover from the fall; and
requesting assistance if the patient pushes the help button, and wherein sequences of human motions are classified into groups of similar postures represented by model-states with a posture model depicting inter-relationships among model-states.

21. The method of claim 20, comprising calling the patient to determine if the patient needs assistance and requesting help if the patient fails to respond to the call.

22. The method of claim 20, further comprising determining a severity of the fall based on the predetermined period or based on one or more accelerometers' output magnitudes.

23. The method of claim 21, comprising off-loading processing of accelerometer outputs to a remote computer.

* * * * *